US009422559B2

(12) United States Patent
Lin et al.

(10) Patent No.: US 9,422,559 B2
(45) Date of Patent: Aug. 23, 2016

(54) PRODUCTION AND UTILIZATION OF A NOVEL ANTI-CANCER DRUG IN THERAPY

(71) Applicants: Shi-Lung Lin, Arcadia, CA (US); David T S Wu, Taipei (TW)

(72) Inventors: Shi-Lung Lin, Arcadia, CA (US); David T S Wu, Taipei (TW)

(*) Notice: Subject to any disclaimer, the term of this patent is extended or adjusted under 35 U.S.C. 154(b) by 0 days.

(21) Appl. No.: 13/964,705

(22) Filed: Aug. 12, 2013

(65) Prior Publication Data

US 2013/0324590 A1 Dec. 5, 2013

Related U.S. Application Data

(63) Continuation-in-part of application No. 12/792,413, filed on Jun. 2, 2010, and a continuation-in-part of application No. 13/572,263, filed on Aug. 10, 2012, now abandoned.

(60) Provisional application No. 61/746,786, filed on Dec. 28, 2012, provisional application No. 61/761,890, filed on Feb. 7, 2013.

(51) Int. Cl.
| | |
|---|---|
| *C12N 15/11* | (2006.01) |
| *C12N 15/00* | (2006.01) |
| *C07H 21/02* | (2006.01) |
| *C12N 15/113* | (2010.01) |

(52) U.S. Cl.
CPC .......... *C12N 15/1137* (2013.01); *C12N 15/111* (2013.01); *C12N 15/113* (2013.01); *C12N 2310/141* (2013.01); *C12N 2330/50* (2013.01); *C12N 2330/51* (2013.01)

(58) Field of Classification Search
None
See application file for complete search history.

(56) References Cited

U.S. PATENT DOCUMENTS

| | | |
|---|---|---|
| 6,251,599 B1 | 6/2001 | Chen et al. |
| 2008/0293143 A1* | 11/2008 | Lin et al. ............. 435/456 |
| 2010/0240126 A1 | 9/2010 | Lin et al. |

FOREIGN PATENT DOCUMENTS

| | | | |
|---|---|---|---|
| WO | WO 2005/056797 | * | 6/2005 |
| WO | WO 2011/025566 A1 | | 3/2011 |

OTHER PUBLICATIONS

Morille et al. Biomaterials 2008, 29:3477-3496.*
Lensch et al., Nat. Biotech. 2007; 25(11)1211-1212.*
(Continued)

*Primary Examiner* — Doug Schultz
(74) *Attorney, Agent, or Firm* — Birch, Stewart, Kolasch & Birch, LLP

(57) ABSTRACT

This invention generally relates to a design and method for developing novel anti-tumor and/or anti-cancer drugs, vaccines and therapies, using microRNA and/or its shRNA homologs/mimics/derivatives. More specifically, the present invention relates to an use of a prokaryote-produced miRNA precursor (pro-miRNA) composition capable of being delivered into human cells and processed by the cells into mature miRNA effectors to elicit specific silencing effects on mir-302-targeted genes, subsequently leading to a beneficial result of tumor suppression and cancer therapy. The prokaryotic cells do not naturally express or process eukaryotic miRNA precursors (pre-miRNA); meanwhile, the present invention also teaches an inducible method for expressing pre-miRNAs, particularly mir-302 precursors by using the prokaryotic transcription system. Since mir-302 is a known tumor suppressor in human, this novel finding advances the design and method for developing new anti-cancer drugs, vaccines and/or therapies directed against multiple kinds of human tumors and cancers.

9 Claims, 38 Drawing Sheets
(18 of 38 Drawing Sheet(s) Filed in Color)

(56) References Cited

OTHER PUBLICATIONS

International Search Report and Written Opinion of the International Searching Authority, dated Mar. 4, 2014 for International Application No. PCT/US2013/054530 (Forms PCT/ISA/220, PCT/ISA/210 and PCT/ISA/237).

Kota et al., "Therapeutic microRNA Delivery Suppresses Tumorigenesis in a Murine Liver Cancer Model," Cell, vol. 137, Jun. 12, 2009, pp. 1005-1017.

Sibley et al., "Novel RNA-based Strategies for Therapeutic Gene Silencing," The American Society of Gene and Cell Therapy, vol. 18, No. 3, Mar. 2010 (Published Online: Jan. 19, 2010), pp. 466-476.

Gao et al, "Aminated Linear and Star-Shape Poly(glycerol methacrylate)s: Synthesis and Self-Assembling Properties", Biomacromolecules, vol. 11 (2010) pp. 889-895.

International Search Report issued in International Application No. PCT/US2014/050114 on Nov. 17, 2014.

Written Opinion issued in International Application No. PCT/US2014/050114 on Nov. 17, 2014.

\* cited by examiner

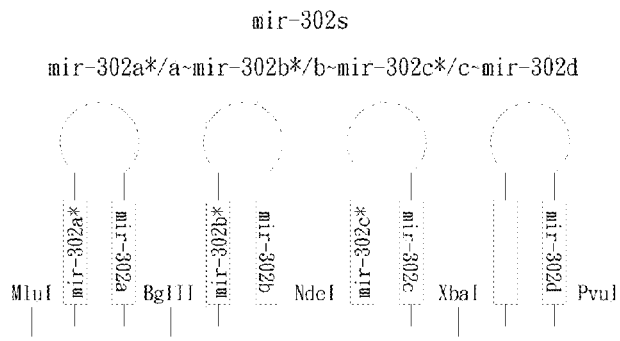

pre-mir-302a: 5'-CCACCACUUAAACGUGGAUGUACUUGCUUU
GAAACUAAA GAAGUAAGUGCUUCCAUGUUUUGGUGAUGG-3' (SEQ.ID.NO.49)
*mir-302a* pre-mir-302b: 5'-GCUCCCUUCAACUUUAACAUGGAAGUGCUUUCU
GUGACUUUGAA AGUAAGUGCUUCCAUGUUUUAGUAGGAGU-3' (SEQ.ID.NO.50)
*mir-302b* pre-mir-302c: 5'-CCUUUGCUUUAACAUGGAGGUACCUGCUGUG
UGAAA CAGAAGUAAGUGCUUCCAUGUUUCAGUGGAGG-3' (SEQ.ID.NO.51)
*mir-302c* pre-mir-302d: 5'-UAACACUCAAACAUGGAAGCACUUAGCUAAGCCAG
GCUAAGUGCUUCCAUGUUUGAGUGUUC-3' (SEQ.ID.NO.52)
*mir-302d*

FIG. 1B

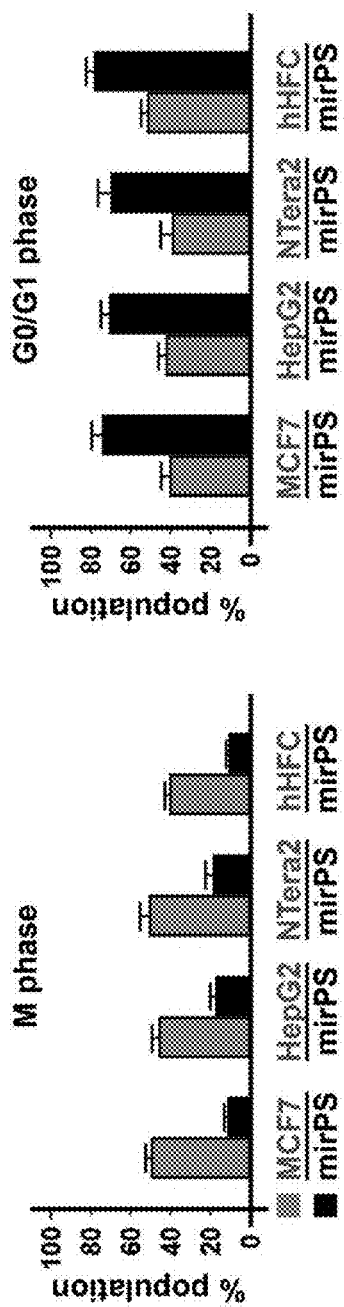
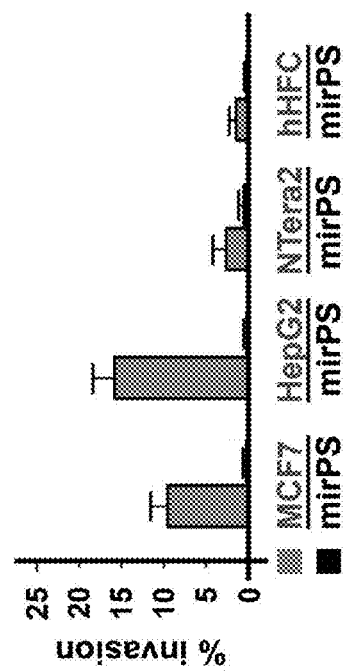
FIG. 6C
FIG. 6D

*Relative Luciferase Activity (RLA) = $\dfrac{\text{level of luciferase activity in Dox-on cells}}{\text{level of luciferase activity in Dox-off cells}}$

PRODUCTION AND UTILIZATION OF A NOVEL ANTI-CANCER DRUG IN THERAPY

CLAIM OF THE PRIORITY

The present application claims priority to the U.S. Provisional Application Ser. No. 61/746,786 filed on Dec. 28, 2012 and No. 61/761,890 filed on Feb. 7, 2013, entitled "Development of Universal Cancer Drugs and Vaccines". The present application also claims priority to the U.S. patent application Ser. No. 12/792,413 filed on Jun. 2, 2010, entitled "Development of Universal Cancer Drugs and Vaccines". The present application further claims priority to the U.S. patent application Ser. No. 13/572,263 filed on Aug. 10, 2012, entitled "An Inducible Gene Expression Composition for Using Eukaryotic Pol-2 Promoter-Driven Transcription in Prokaryotes and The Applications Thereof". The present application is a continuation-in-part application of the U.S. patent application Ser. No. 12/792,413 filed on Jun. 2, 2010, entitled "Development of Universal Cancer Drugs and Vaccines", and the U.S. patent application Ser. No. 13/572,263 filed on Aug. 10, 2012, entitled "An Inducible Gene Expression Composition for Using Eukaryotic Pol-2 Promoter-Driven Transcription in Prokaryotes and The Applications Thereof", which are hereby incorporated by reference as if fully set forth herein.

FIELD OF THE INVENTION

This invention generally relates to a production design and the related utilization of novel DNA/RNA-based therapeutical drugs and/or vaccines for cancer therapy. More particularly, the present invention relates to the design and method of using a novel nucleic acid composition capable of being processed into small RNA-based gene silencing effectors upon delivery into human cells and then inducing specific gene silencing effects on mir-302-targeted cell cycle regulators and/or oncogenes, resulting in a tumor suppression and/or cancer prevention effect on tumor/cancer cell growth, invasion and metastasis. Preferably, the small RNA-based gene silencing effectors include tumor suppressor microRNA (TS-miRNA) such as mir-302a, mir-302b, mir-302c, mir-302d, mir-302e, mir-302f, and their precursors (pre-miRNA) as well as their manually re-designed and/or modified small hairpin RNA (shRNA)/siRNA homologues/derivatives, and a combination thereof. The human cells of interest include somatic normal or tumor/cancer cells ex vivo and/or in vivo.

BACKGROUND OF THE INVENTION

Stem cells are like a treasure box containing numerous effective ingredients useful for stimulating stem cell growth/regeneration, repairing and/or rejuvenating damaged/aged tissues, treating degenerative diseases, and preventing tumor/cancer formation. Hence, it is conceivable that we can use these stem cells as a tool for novel drug identification and production. As a result, the drugs so obtained are useful for developing pharmaceutical and/or therapeutic applications, such as a biomedical utilization, device and/or apparatus for diagnosis, stem cell generation, stem cell research and/or therapy, tissue/organ repair and/or rejuvenation, wound healing treatment, tumor suppression, cancer therapy and/or prevention, disease treatment, drug production, and a combination thereof.

MicroRNA (miRNA) mir-302 is the most predominant RNA found in human embryonic stem (hES) and induced pluripotent stem (iPS) cells, yet its function is largely unclear. Previous studies have shown that ectopic overexpression of mir-302 beyond the level found in hES cells is able to reprogram both human normal and cancerous cells to normal hES-like pluripotent stem cells with a slow cell cycle rate (20-24 hour/cycle) and dormant-cell-like morphology (Lin et al., 2008 and 2011; U.S. Ser. No. 12/792,413; EP2198025). Relative quiescence is a defined characteristic of these mir-302-induced pluripotent stem (mirPS) cells, whereas hES and other previously reported three/four-factor-induced (by Oct4-Sox2-Klf4-c-Myc or by Oct4-Sox2-Nanog-Lin28) iPS cells have all shown highly proliferative ability (12-15 hour/cycle) and inexorable tumorigenetic tendency (Takahashi et al., 2006; Yu et al., 2007; Wernig et al., 2007). Despite the unknown mechanism underlying this anti-proliferative characteristic of mirPS cells, we have identified the possible involvement of two mir-302-targeted G1-checkpoint regulators, cyclin-dependent kinase 2 (CDK2) and cyclin D (Lin et al., 2010; U.S. Ser. No. 12/792,413). Progression in the eukaryotic cell cycle is driven by activities of cyclin-dependent kinases (CDKs), which forms functional complexes with positive regulatory subunits, cyclins, as well as by negative regulators, CDK inhibitors (CKIs, such as p14/p19Arf, p15Ink4b, p16Ink4a, p18Ink4c, p21Cip1/Waf1, and p27Kip1). In mammalian cells, different cyclin-CDK complexes are involved in regulating different cell cycle transitions, such as cyclin-D-CDK4/6 for G1 progression, cyclin-E-CDK2 for G1-S transition, cyclin-A-CDK2 for S-phase progression, and cyclinA/B-CDC2 (cyclin-A/B-CDK1) for entry into M-phase. Hence, it is conceivable that the anti-proliferative function of mir-302 likely results from such co-suppression of CDK2 and cyclin D during G1-S transition.

However, studies of the mir-291/294/295 family, an analog to human mir-302 in mouse, revealed a totally different function from the role of mir-302 in human cells. In mouse embryonic stem (mES) cells, ectopic expression of mir-291/294/295 promoted fast cell proliferation and G1-S transition through direct silencing of p21Cip1 (also named CDKN1A) and serine/threonine-protein kinase Lats2 (Wang et al., 2008), leading to high tumorigenecity of the transfected cells. It has been known that transgenic mice lacking p21Cip1/Waf1 were shown to display normal development with a defect in the G1 checkpoint control (Deng et al., 1995). Yet, the role of Lats2 remains to be determined because of its function in recruitment of gamma-tubulin and spindle formation at the onset of mitosis. Loss of Lats2 in mouse embryos was found to cause severe mitotic defects and lethality, indicating that silencing of Lats2 may hinder rather than facilitate cell division (Yabuta et al., 2007). Taken together, silencing of p21Cip1 seems to be the key mechanism underlying such mir-291/294/295-induced tumorigenecity. Nevertheless, our efforts to screen the mir-302 target site in human p21Cip1 gene all resulted in negative. The same negative result has also been shown by two of the most renowned online miRNA-target prediction programs TARGETSCAN (http://www.targetscan.org/) and PICTAR-VERT (http://pictar.mdc-berlin.de/). Therefore, although mir-302 and mir-291/294/295 are homologous analogs, their functions in regulating cell tumorigenecity are actually opposite to each other, indicating that homologous microRNAs may not possess the same function! This finding also suggests that current studies using siRNA mimics to replace natural microRNAs may not deliver the same result as well!

The genomic sequence encoding mir-302 is located in the 4q25 locus of human chromosome 4, a conserved region frequently associated with longevity. More precisely, mir-302 is encoded in the intron region of the La ribonucleoprotein domain family member 7 (LARP7) gene and expressed via an intronic microRNA biogenesis pathway (Barroso-delJesus, 2008; Ying and Lin, 2004; FIG. 13). Native mir-302 consists of four familial homologues sense (mir-302b, c, a and d) and three distinct antisense members (mir-302b*, c* and a*), all of which are transcribed together as a polycistronic RNA cluster along with another miRNA, mir-367 (Suh et al., 2004). In our priority invention U.S. Ser. No. 12/792,413, we have observed that mir-302 can stimulate the expression of other miRNAs, such as mir-92, mir-93, mir-367, mir-371, mir-372, mir-373, mir-374, and the whole mir-520 familial members. Analyses using the online "TARGETSCAN" and "PICTAR-VERT" programs in the Sanger miRBase::Sequences website (http://microrna.sanger.ac.uk/), further revealed that mir-302 shares over 400 target genes with these stimulated miRNAs, suggesting that they may also play a similar role like mir-302. These shared target genes include, but not limited, members of RAB/RAS-related oncogenes, ECT-related oncogenes, pleiomorphic adenoma genes, E2F transcription factors, cyclin D binding Myb-like transcription factors, HMG-box transcription factors, Sp3 transcription factors, transcription factor CP2-like proteins, NFkB activating protein genes, cyclin-dependent kinases (CDKs), MAPK/JNK-related kinases, SNF-related kinases, myosin light chain kinases, TNF-alpha-induce protein genes, DAZ-associated protein genes, LIM-associated homeobox genes, DEAD/H box protein genes, forkhead box protein genes, BMP regulators, Rho/Rac guanine nucleotide exchange factors, IGF receptors (IGFR), endothelin receptors, left-right determination factors (Lefty), cyclins, p53 inducible nuclear protein genes, RB-like 1, RB binding protein genes, Max-binding protein genes, c-MIR cellular modulator of immune recognition, Bcl2-like apoptosis facilitator, protocadherins, integrin $\beta4/\beta8$, inhibin, ankyrins, SENP1, NUFIP2, FGF9/19, SMAD2, CXCR4, EIF2C, PCAF, MECP2, histone acetyltransferase MYST3, nuclear RNP H3, and many nuclear receptors and factors. The majority of these target genes are highly involved in embryonic development and cancer tumorigenecity. Thus, it is conceivable that miR-302 can further stimulate its homologous microRNAs, such as miR-92, miR-93, miR-367, miR-371, miR-372, miR-373, miR-374, and miR-520, to enhance and/or maintain its function.

MicroRNA (miRNA) is a cytoplasmic gene inhibitor and often functions to suppress the translation of it targeted gene transcripts (mRNAs) via binding to a specific target site with high complementarity and then forming a RNA-induced silencing complex (RISC) to block or degrade the mRNAs. Hence, the binding stringency between miRNA and its target genes determines the real function of a miRNA. To this, our previous studies (Lin et al., 2010; U.S. Ser. No. 12/792,413) have provided significant insights into the mechanism underlying mir-302-mediated tumor suppression. In humans, mir-302 targets multiple cell cycle regulators CDK2, cyclins D1/D2 and BMI-1 genes for silencing, but interestingly, not p21Cip1. As aforementioned, simultaneous silencing of CDK2 and cyclin D blocks the cell cycle transition from the G1 to S phase, leading to a slow cell proliferation rate. In addition, silencing of BMI-1 stimulates the elevation of two major tumor suppressors p16Ink4a and p14ARF expression, which may further attenuate cell proliferation and inhibit tumor formation. Since p16Ink4a/p14ARF are elevated while p21Cip1 may not be affected in human cells, the anti-tumorigenecity function of mir-302 likely results from both p16Ink4a-Rb and/or p14/19ARF-p53 pathways in addition to the co-suppression of cyclin-E-CDK2 and cyclin-D-CDK4/6 pathways.

Based on the above anti-tumorigenecity feature of mir-302, we may use mir-302 as a drug to treat human tumors and cancers. However, there are four major problems in this attempt: (1) As a gene silencing effector, mir-302 must function through its precursor form, a hairpin-like 73-75-nucleotide RNA that still can not be made by any currently available RNA synthesis technology. To ensue its sequence fidelity, the maximal length of a synthesized RNA is around 45-55-nucleotide, which is not sufficient to form a mir-302 precursor (pre-mir-302). (2) We also need a high concentration of mir-302 beyond the level found in hES cells in order to induce its anti-tumor/cancer effects (Lin et al., 2010). Yet, there is currently no method capable of generating such a high amount of pre-mir-302 for affordable drug production. Isolating pre-mir-302 from hES or iPS cells is very costly, whereas bacterial competent cells are not able to produce the high secondary structure of a pre-mir-302. (3) Synthetic siRNA mimics have never succeeded in animal trials. Due to the short life (3-5 days) and high toxicity of the siRNA mimics, siRNA can not be used to replace the natural mir-302 under an in vivo condition. Also, the use of siRNA mimics has been reported to over-saturate cellular microRNA pathways and cause cytotoxicity (Grimm et al., 2006). (4) The full mir-302 functionality requires both sense mir-302 and its reverse mir-302* strands in the precursor, whereas current siRNA designs fail to provide the function of mir-302* (such as mir-302a*, mir-302b* and mir-302c*). As a result, an affordable and reliable method for producing and/or isolating pre-mir-302 is the key element required for developing mir-302-mediated anti-tumor/cancer therapy and its related drugs.

In sum, there remains a need for effective and safe methods of producing, isolating and utilizing mir-302 and its precursors as well as the related homologues/derivatives in drug/vaccine development and cancer therapy.

SUMMARY OF THE INVENTION

The present invention is a design and method for utilizing microRNA precursors (pre-miRNAs) as therapeutical drugs and/or vaccines for cancer therapy. More particularly, the present invention relates to the design and method of using a nucleic acid composition capable of being processed into small RNA-based gene silencing effectors upon delivery into human cells and then inducing specific gene silencing effects on mir-302-targeted cell cycle regulators and/or oncogenes, resulting in a tumor suppression and/or cancer prevention effect useful for inhibiting tumor/cancer cell growth, proliferation, invasion, and metastasis. Preferably, these small RNA-based gene silencing effectors include tumor suppressor microRNA (TS-miRNA) such as mir-302a, mir-302b, mir-302c, mir-302d, mir-302e, mir-302f, and their precursors (pre-miRNAs) as well as their manually re-designed small hairpin-like RNA (shRNA) homologues/derivatives, and a combination thereof. The designs of shRNA homologues/derivatives include mismatched and perfectly matched nucleic acid compositions of the shRNA and its homologous small interfering RNA (siRNA) in a single separate unit or a multiple unit cluster, all of which may improve the target specificity and reduce the copy number of mir-302 required for delivery and therapy. The human cells of interest include normal and/or tumor/cancerous cells in vitro, ex vivo and/or in vivo.

Native microRNA (miRNA) is sized approximately 18-27 nucleotides (nt) in length and capable of either directly degrading its targeted messenger RNA (mRNA) or suppressing the translation of its targeted mRNA, depending on their mutual complementarity between miRNA and the targets. The mir-302 family (mir-302s) is a group of highly homologous miRNAs conserved in many mammals. Mir-302s consists of four major members which are transcribed together as a non-coding RNA cluster containing mir-302b, mir-302c mir-302a, mir-302d and mir-367 in a 5' to 3' direction (Suh et al., 2004). Recently, the fifth and sixth mir-302 members were also found outside the familial cluster, namely mir-302e and mir-302f. Although mir-367 and mir-302s are co-expressed together in nature, their functions are very different. In the present invention, we prefer to express only mir-302s due to its anti-tumorigenecity function. In some other embodiments, we may further use manually re-designed hairpin loops, such as 5'-GCTAAGCCAG GC-3' (SEQ.ID.NO.1) and 5'-GCCTGGCTTA GC-3' (SEQ.ID.NO.2), to replace the original hairpin loop of a mir-302 precursor (pre-mir-302) for easy intracellular delivery and expression. Normally, mir-302 is only abundantly expressed in human embryonic stem (hES) and induced pluripotent stem (iPS) cells, but not other differentiated somatic cells (Tang et al., 2007; Suh et al., 2004). Since mir-302s is a group of homologous small inhibitory RNAs capable of silencing their target genes with high complementarity, mir-302 may be responsible for preventing errant and premature oncogene activation in hES and iPS cells, which may be also useful for developing anti-tumor/cancer drugs. In fact, hES cells before the morula stage (32-64 cell stage) often present a relatively slow cell cycle rate similar to that of mir-302-induced pluripotent stem (mirPS) cells (Lin et al., 2010), suggesting that mir-302 plays a dual role in regulating normal stem cell growth while preventing tumor/cancer formation.

All mir-302 members share a totally identical sequence in their first 5'-seventeen (17) nucleotides, including the entire seed motif 5'-UAAGUGCUUC CAUGUUU-3' (SEQ.ID.NO.3), and contain over 85% homology in their complete 23-nucleotide mature miRNA sequences. Based on the predicted results of on-line computing programs TARGETSCAN (http://www.targetscan.org/) and PICTAR-VERT (http://pictar.mdc-berlin.de/), these members currently and concurrently target against almost the same cellular genes, including over 607 human genes. In addition, mir-302 also shares many overlapping target genes with mir-92, mir-93, mir-200c, mir-367, mir-371, mir-372, mir-373, mir-374, and mir-520 familial members, which may provide certain similarity in functionality. Most of these target genes are developmental signals and transcriptional factors involved in initiation and/or establishment of certain lineage-specific cell differentiation during early embryogenesis (Lin et al., 2008). Many of these target genes are also known oncogenes. As many of these targeted developmental signals and differentiation-related transcription factors are oncogenes, mir-302s likely functions as a tumor suppressor to prevent the deviation of normal hES cell growth into tumor/cancer formation.

In one preferred embodiment, the present invention is a non-vector-based pre-mir-302 production and delivery method for treating human tumors/Cancers. As aforementioned, pre-mir-302 is sized about 73 to 75-nucleotide in length which can not be synthesized by current RNA synthesis technology due to its length limit within 45 to 55-nucleotide. Hence, we need to adopt a new method for not only generating but also amplifying the amount of pre-mir-302 for affordable drug production. To this, the present invention utilizes the prokaryote-producing microRNA precursor (pro-miRNA) technology learning from our priority invention U.S. Ser. No. 13/572,263 for preparing pre-mir-302 mimics. Pro-miRNA is a novel kind of hairpin-like pre-miRNA mimics produced by prokaryotic competent cells, such as competent E. coli DH5alpha strain cells. As any one of ordinary skill in the art has known very well that prokaryotic and eukaryotic transcription machineries are very different and are not compatible to each other, we need to modify a prokaryotic transcription system for transcribing eukaryotic genes and pre-miRNAs. Our priority U.S. Ser. No. 13/572,263 has taught that prokaryotes can adopt eukaryotic pol-2 and pol-2-like (i.e. CMV) promoters to transcribe abundant pre-mir-302-like hairpin RNAs (pro-mir-302) via certain chemical induction. Such a transcription inducer not only makes a prokaryotic transcription system compatible to eukaryotic gene expression but also stabilize the secondary structures of the eukaryotic gene transcripts in prokaryotes. The advantages of this pro-miRNA technology are: first, cost-effective production of a specific pre-miRNA or a group of desired pre-miRNAs due to the fast and easy growth nature of bacterial competent cells; second, industrial bulk production at a multi-gram to kilogram level; third, easy and inexpensive handling because of no need for culturing dedicate hybridomas or mammalian cells; fourth, high sequence fidelity due to the pol-2 promoter-like transcription induced by the chemical reagents; and last, high purity of the resulting pre-miRNA product due to lack of Dicer and other microRNA expression in prokaryotic cells. The desired pro-miRNA so obtained can be easily isolated (Example 20) and further purified (Example 21) from the bacterial extracts and/or lysates, which are useful for developing many pharmaceutical and therapeutical applications.

We have produced abundant pre-mir-302-like pro-miRNA, pro-mir-302, (Examples 18-21) and used it for enhancing wound healing (Example 22). For treatments, the isolated pro-mir-302 was formulated with a pre-prepared ointment base containing cocoa butter, cottonseed oil, olive oil, sodium pyruvate, and white petrolatum. The concentration of pro-mir-302 in the prepared ointment is 10 µg/mL. Skin open wounds were generated by scalpel dissection. Ointments with or without pro-mir-302 were directly applied on the wounds, respectively, and covered the whole wounded area. Then, the treated area was further sealed by liquid bandage. As show in FIG. 14, within two weeks, the results clearly showed that the wound area with pro-mir-302 treatments significantly enhanced the healing speed over two-fold faster than all other control groups. Moreover, the healed area with pro-mir-302-treatments showed normal hair regrowth and left no scar (as indicated by black arrow), while other treatments resulted in minor scars with no hair growth. Clearly, this result indicates that pro-mir-302 has a functional role in stimulating normal tissue repairing and regeneration.

We also have purified and formulated the above pro-mir-302 into a soluble drug for injection and tested it for liver cancer therapy in vivo (Example 23). As shown in FIG. 15, after three injection treatments, the pro-mir-302 drug successfully reduced approximately 90% volume of the engrafted human liver cancers in vivo, shirking the average cancer size to only 10% compared to the untreated cancers. Moreover, further histological examination with hematoxylin & eosin (H&E) staining demonstrated that such a significant cancer therapy effect is resulted from not only the reported anti-tumorigenecity property of mir-302 (Lin et al., 2010) but also another novel reprogramming function that has not yet been observed before. For instance, FIG. 16 clearly shows that mir-302 can reprogram high-grade malignant human liver cancer grafts in vivo to a more benign state similar to that of normal liver tissues! These treated cancer grafts can even form normal liver structures, such as classical liver lobules, central veins (CV) and portal triads (PT). As a result, it suggests that mir-302 is able to not only inhibit tumor/cancer growth but also help to repair and/or regenerate normal tissues in vivo, leading to a very beneficial effect in cancer therapy.

In another preferred embodiment, the present invention also provides a vector-based mir-302 expression for treating tumors/cancers. As shown in our priority invention U.S. Ser. No. 12/792,413, we have designed and developed an inducible pTet-On-tTS-miR302s expression vector (FIG. 1A) in conjunction with either viral infection, electroporation or liposomal/polysomal transfection methods for delivering mir-302 into normal and/or cancerous human cells. The redesigned mir-302 construct is consisting of four small non-coding RNA members: mir-302a, b, c and d in one cluster (mir-302s; FIG. 1B). The expression of this mir-302s construct is driven by a tetracycline-responsive-element (TRE)-controlled cytomegaloviral (CMV) promoter in response to doxycycline (Dox) stimulation. After infection/transfection, the expression of mir-302 followed the natural miRNA biogenesis pathway, in which the mir-302s construct is co-transcribed with a reporter gene such as red-shifted fluorescent protein (RGFP), and then further processed into individual mir-302 members by spliceosomal components and/or cytoplasmic RNaseIII Dicers (FIG. 2A) (Lin et al., 2003). As a result of this strategy, miRNA microarray analysis (Example 3) shows that all sense mir-302 members were efficiently expressed in transfected cells after Dox stimulation (FIG. 1C). The procedure for transducing the mir-302 expression vector into human cells is summarized in FIG. 2B.

By mimicking the natural intronic miRNA biogenesis pathway (FIG. 2A), the inventors have devised an intronic miRNA expression system to transcribe a recombinant RGFP gene, namely SpRNAi-RGFP, which contains a man-made/artificial splicing-competent intron (SpRNAi) capable of producing intronic miRNA and/or shRNA-like gene silencing effectors (Lin et al., 2003; Lin et al., (2006) *Methods Mol Biol.* 342: 295-312). The SpRNAi is co-transcribed within the pre-mRNA of the SpRNAi-RGFP gene by Pol-II RNA polymerases and cleaved out by RNA splicing components. Subsequently, the spliced SpRNAi is further processed into mature gene silencing effectors, such as native miRNAs and man-made shRNAs, so as to trigger specific RNA interference (RNAi) effects on target genes. Meanwhile, after intron splicing, the exons of the SpRNAi-RGFP gene transcript are linked together to form a mature mRNA for translation of a RGFP reporter protein useful for identifying the miRNA/shRNA expression. For quantification measurement, one fold RGFP concentration equaled to four folds the mir-302 concentration. Alternatively, some functional protein exons may be used in place of RGFP to provide additional gene functions, such as hES gene markers for somatic cell reprogramming. Given that there are currently over 1000 native miRNA species found in vertebrates without clear function and many more new miRNAs continue to be identified, our intronic miRNA expression system may also serve as a powerful tool for testing these miRNA functions in vitro and in vivo.

The SpRNAi intron contains several consensus nucleotide components, consisting of a 5'-splice site, a branch-point (BrP) motif, a poly-pyrimidine tract, and a 3'-splice site. In addition, a hairpin miRNA or shRNA precursor is inserted in between the 5'-splice site and the BrP motif. This portion of intron usually forms a lariat structure during RNA splicing and processing. Moreover, the 3'-end of SpRNAi contains a multiple translational stop codon region (T codon) to increase the accuracy of intronic RNA splicing and processing. When presented in a cytoplasmic mRNA, this T codon signals the activation of intracellular nonsense-mediated decay (NMD) system to degrade any unstructured RNA accumulated in the cell for preventing cytotoxicity. However, the highly structured shRNA and precursor miRNA (pre-miRNA) will be preserved for further Dicer cleavage to form mature siRNA and miRNA, respectively. For intronic miRNA/shRNA expression, we manually incorporate the SpRNAi in the DraII restriction site of a RGFP gene (Lin et al., 2006 and 2008). This forms a recombinant SpRNAi-RGFP gene. The cleavage of RGFP with DraII generates an AG-GN nucleotide break with three recessing nucleotides in each end, which will form 5'- and 3'-splice sites, respectively, after SpRNAi insertion. Because this intronic insertion disrupts the integrity of RGFP protein, which can be recovered by intron splicing, we are able to determine the expression of mature miRNA/shRNA through the appearance of red RGFP in the transfected cells. The RGFP gene also contains multiple exonic splicing enhancers (ESEs) to increase RNA splicing accuracy and efficiency.

In details, the SpRNAi intron contains a 5'-splice site homologous to either 5'-GTAAGAGK-3' (SEQ.ID.NO.4) or GU(A/G)AGU (SEQ.ID.NO.35) motifs (i.e. 5'-GTAAGAG-GAT-3' (SEQ.ID.NO.36), 5'-GTAAGAGT-3' (SEQ.ID.NO.37), 5'-GTAGAGT-3' (SEQ.ID.NO.38) and 5'-GTAAGT-3' (SEQ.ID.NO.39)), while its 3'-end is a 3'-splice site that is homologous to either GWKSCYRCAG (SEQ.ID.NO.5) or CT(A/G)A(C/T)NG (SEQ.ID.NO.40) motifs (i.e. 5'-GATATCCTGC AG-3' (SEQ.ID.NO.41), 5'-GGCTGCAG-3' (SEQ.ID.NO.42) and 5'-CCACAG-3' (SEQ.ID.NO.43)). Moreover, a branch point sequence is located between the 5'- and 3'-splice sites, containing high homology to 5'-TACTWAY-3' (SEQ.ID.NO.6) motifs, such as 5'-TACTAAC-3' (SEQ.ID.NO.44) and 5'-TACTTAT-3' (SEQ.ID.NO.45). The adenosine "A" nucleotide of the branch-point sequence can form a part of (2'-5')-linked lariat intron RNA by cellular (2'-5')-oligoadenylate synthetases and spliceosomes in almost all spliceosomal introns. Furthermore, a poly-pyrimidine tract is closely located between the branch-point and 3'-splice site, containing a high T or C content sequence homologous to either 5'-(TY)m(C/-)(T)nS(C/-)-3' (SEQ.ID.NO.7) or 5'-(TC)nNCTAG(G/-)-3' (SEQ.ID.NO.8) motifs. The symbols of "m" and "n" indicate multiple repeats ≥1; most preferably, the m number is equal to 1 to 3 and the n number is equal to 7 to 12. The symbol "–" refers a nucleotide that can be skipped in the sequence. There are also some linker nucleotide sequences for the connection of all these synthetic intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U)."

In one other possible embodiment, the present invention is a direct (exonic) mir-302 miRNA/shRNA expression system, which can be used for generating mir-302-like gene silencing effectors directly from the expression system without going through intracellular RNA splicing and/or NMD mechanisms. However, the drawback of this method is that the expression of mir-302-like gene silencing effectors is not regulated by any intracellular surveillance system, such as NMD, and may therefore over-saturate the natural miRNA biogenesis pathway to cause cytotoxicity (Grimm et al., 2006). The expression system used for this method can be a linear or circular nucleic acid composition selected from the group of plasmid, viral vector, lentiviral vector, transposon, retrotransposon, jumping gene, protein-coding gene, non-coding gene, artificially recombinant transgene, and a combination thereof. The mir-302-like gene silencing effectors, including miRNA, shRNA, siRNA and their precursors as well as homologues/derivatives, are expressed under the control of a tissue-specific or non-specific RNA promoter selected from the group consisting of type-II RNA polymerase (Pol-II), viral polymerase, type-III RNA polymerase (Pol-III), type-I RNA polymerase (Pol-I), and tetracycline responsive element-controlled RNA polymerase (TRE) promoters. The viral promoters are Pol-II-like RNA promoters isolated but not limited from cytomegalovirus (CMV), retrovirus long-terminal region (LTR), hepatitis B virus (HBV), adenovirus (AMID), and adeno-associated virus (AAV). For example, a lentiviral LTR promoter is sufficient to produce up to $5 \times 10^5$ copies of pre-mRNA transcripts per cell. It is also feasible to insert a drug-sensitive repressor (i.e. tS) in front of the RNA polymerase promoter in order to control the transcription rate of the gene silencing effectors. The repressor can be inhibited by a chemical drug or antibiotics selected from the group of G418, neomycin, tetracycline, doxycycline, ampicillin, kanamycin, puromycin, and their derivatives, etc.

In one aspect, multiple transgenes and/or vectors expressing various intronic gene silencing effectors may be used to achieve gene silencing on the mir-302-targeted genes. Alternatively, multiple gene silencing effectors may be generated from one intronic insert. For example, it has been reported that the ectopic expression of one anti-EGFP pre-miRNA-containing intron in zebrafish generates two different size miRNAs, namely miR-EGFP(282/300) and miR-EGFP(280-302), indicating that one insert of the SpRNAi may generate multiple gene-silencing effectors (Lin et al. (2005) *Gene* 356: 32-38). In certain cases, intronic gene-silencing effectors can hybridize with a target gene transcript (i.e. mRNA) to form double-stranded siRNAs for triggering secondary RNA interference (RNAi) effects. Because these gene-silencing effectors are constantly produced from the transgene vector, it will alleviate the concerns of fast RNA degradation in vivo. The advantage of this strategy is in its stable delivery through the vector-based transgene transfection or viral infection, providing a reliable long-term gene silencing efficacy.

Because the stem-loop structures of some native pre-miRNAs are too large and/or complicated to fit in a miRNA expression system/vector, the inventors often use a manually re-designed tRNA$^{met}$ loop (i.e. 5'-(A/U)UCCAAGGGGG-3' (SEQ.ID.NO.46)), to replace the native pre-miRNA loops. The tRNA$^{met}$ loop has been shown to efficiently facilitate the export of manually re-designed miRNAs from nucleus to cytoplasm through the same Ran-GTP and Exportin-5 transporting mechanisms as native miRNAs do (Lin et al., 2005). Advantageously, the present invention now uses a pair of manually improved pre-mir-302 loops, including 5'-GCTAAGCCAG GC-3' (SEQ.ID.NO.1) and 5'-GCCTG-GCTTA GC-3' (SEQ.ID.NO.2), which provide the same nuclear export efficiency as the native pre-miRNAs but not interfere with the tRNA exportation. Also, this improvement enhances the formation of mir-302a-mir-302a* and mir-302c-mir-302c* duplexes, which may increase the overall function and stability of mir-302s. The design of these new pre-miRNA loops is modified by the combination of the tRNA$^{met}$ loop and the short stem-loops of mir-302b/mir-302a, which are highly expressed in human ES cells but not in other differentiated tissue cells. Thus, the use of these recombinant/man-made/artificial hairpin loops in the structure of mir-302 will not interfere with the native miRNA pathway in human body, resulting in a much less cytotoxicity and more safety.

The cluster of familial mir-302 pre-miRNAs is formed by hybridization and linkage/ligation of synthetic mir-302 homologues, consists of four parts: mir-302a, mir-302b, mir-302c and mir-302d pre-miRNAs in a 5' to 3' direction (FIG. 1B). All of these manually re-designed mir-302 miRNA/shRNA molecules possess an identical 5'-end in their first 17 nucleotides [e.g. 5'-UAAGUGCUUC CAUGUUU-3' (SEQ.ID.NO.3)]. Synthetic oligonucleotides used for DNA recombination of the mir-302 pre-miRNA cluster are listed: including mir-302a-sense, 5'-GTCACGCGTT CCCAC-CACTT AAACGTGGAT GTACTTGCTT TGAAACTAAA GAAGTAAGTG CTTCCATGTT TTGGTGATGG ATA-GATCTCT C-3' (SEQ.ID.NO.9); mir-302a-antisense, 5'-GAGAGATCTA TCCATCACCA AAACATGGAA GCACTTACTT CTTTAGTTTC AAAGCAAGTA CATC-CACGTT TAAGTGGTGG GAACGCGTGA C-3' (SEQ.ID.NO.10); mir-302b-sense, 5'-ATAGATCTCT CGCTC-CCTTC AACTTTAACA TGGAAGTGCT TTCTGTGACT TTGAAAGTAA GTGCTTCCAT GTTTTAGTAG GAGTCGCTCA TATGA-3' (SEQ.ID.NO.11); mir-302b-antisense, 5'-TCATATGAGC GACTCCTACT AAAA-CATGGA AGCACTTACT TTCAAAGTCA CAGAAAG-CAC TTCCATGTTA AAGTTGAAGG GAGCGAGAGA TCTAT-3' (SEQ.ID.NO.12); mir-302c-sense, 5'-CCATATG-GCT ACCTTTGCTT TAACATGGAG GTACCTGCTG TGTGAAACAG AAGTAAGTGC TTCCATGTTT CAGTGGAGGC GTCTAGACAT-3' (SEQ.ID.NO.13); mir-302c-antisense, 5'-ATGTCTAGAC GCCTCCACTG AAA-CATGGAA GCACTTACTT CTGTTTCACA CAGCAGG-TAC CTCCATGTTA AAGCAAAGGT AGCCATATGG-3' (SEQ.ID.NO.14); mir-302d-sense, 5'-CGTCTAGACA TAA-CACTCAA ACATGGAAGC ACTTAGCTAA GCCAG-GCTAA GTGCTTCCAT GTTTGAGTGT TCGCGATCGC AT-3' (SEQ.ID.NO.15); and mir-302d-antisense, 5'-ATGC-GATCGC GAACACTCAA ACATGGAAGC ACTTAGC-CTG GCTTAGCTAA GTGCTTCCAT GTTTGAGTGT TATGTCTAGA CG-3' (SEQ.ID.NO.16). Alternatively, we may use the manually re-designed shRNA formed by the hybrid of synthetic miR-302s-sense, 5'-GCAGATCTCG AGGTACCGAC GCGTCCTCTT TACTTTAACA TGGAAATTAA GTGCTTCCAT GTTTGAGTGG TGTG-GCGCGA TCGATATCTC TAGAGGATCC ACATC-3' (SEQ.ID.NO.17) and mir-302s-antisense, 5'-GATGTGGATC CTCTAGAGAT ATCGATCGCG CCACACCACT CAAA-CATGGA AGCACTTAAT TTCCATGTTA AAGTAAA-GAG GACGCGTCGG TACCTCGAGA TCTGC-3' (SEQ.ID.NO.18), in place of the mir-302 pre-miRNA cluster for easy intronic insertion. The mir-302 shRNA shares over 85% homology to all native mir-302 members and targets the same cellular genes in human. In design of mir-302 homologues, thymine (T) can be used in place of uracil (U) or vice versa.

For intronic insertion of the mir-302 pre-miRNA/shRNA, given that the insertion site of the recombinant SpRNAi-RGFP transgene is flanked with a PvuI and an MluI restriction/cloning site at its 5'- and 3'-ends, respectively, the primary insert can be easily removed and replaced by various pre-miRNA/shRNA inserts (e.g. mir-302 pre-miRNA/shRNA), which possess matched cohesive ends to the PvuI and an MluI restriction sites. By changing the intronic inserts directed against various gene transcripts, the present invention of the intronic mir-302s expression system can be used as a powerful tool for inducing targeted gene silencing in vitro, ex vivo and in vivo. After intronic insertion, the mir-302-inserted SpRNAi-RGFP transgene is further inserted into the restriction/cloning site (i.e. a XhoI-HindIII site) of a Dox-inducible pSingle-tTS-shRNA vector to form a pTet-On-tTS-mir302s expression vector for intracellular expression (FIG. 1A).

Delivery of the pre-mir-302-like (pro-mir-302) or mir-302-expressing nucleic acid composition into human cells can be accomplished using either a non-transgenic or a transgenic method selected from the group of liposomal/polysomal/chemical transfection, DNA recombination, electroporation, gene gun penetration, transposon/retrotransposon insertion, jumping gene integration, micro-injection, viral infection, retroviral/lentiviral infection, and a combination thereof. To prevent the risks of random transgene insertion and cell mutation, the present invention preferably uses either liposomal or polysomal transfection to deliver the mir-302 expression vector and/or the mir-302-like gene silencing effectors (such as pre-mir-302 and/or pro-mir-302) into the targeted human cells (i.e. tumor/cancer cells). The transduced mir-302 level may depend on the concentration of mir-302-like gene silencing effectors or the expression rate of the TRE-regulated CMV promoter on the pTet-On-tTS-mir302s vector, in the presence of various Dox concentrations. Therefore, the present invention provides a controllable mechanism by using a defined drug (i.e. Dox) or the pre-/pro-mir-302 concentration to regulate the mir-302 level in vitro, ex vivo and in vivo. As a result, we can prevent any possible cytotoxicity effect resulted from RNA accumulation or over-saturation in the treated cells. Alternatively, the mir-302 expression may be regulated by a CMV promoter, which is often silenced after about one-month activation in human cells due to DNA methylation. Such a one-month activation mechanism is also beneficial for cancer therapy to prevent long-term RNA accumulation or over-saturation in the treated cells.

In sum, the present invention has adopted a novel design and strategy for using either vector-based or non-vector-based mir-302-like gene silencing effectors as therapeutical drugs for tumor suppression and cancer therapy. The mir-302-like gene silencing effectors include mir-302a, mir-302b, mir-302c, mir-302d, and their hairpin-like microRNA precursors (pre-miRNAs and/or pro-miRNAs) as well as manually re-designed small hairpin RNA (shRNA) homologues/derivatives, and a combination thereof. In one preferred embodiment, the present invention provides a design and method for treating human tumors and cancers using a recombinant nucleic acid composition capable of being delivered and processed into a sufficient amount of mir-302-like gene silencing effectors that can inhibit the cellular mir-302-targeted cell cycle regulators and oncogenes in the treated tumor/cancer cells, resulting in a beneficial effect in tumor/cancer therapy. The recombinant nucleic acid composition may express mir-302-like gene silencing effectors through a constitutive (i.e. CMV) or a drug-inducible (i.e. TRE-CMV) promoter-driven transcription in the treated cells. Alternatively, the recombinant nucleic acid composition may be used for prokaryote-driven pre-mir-302 (pro-mir-302) production and then used the pro-mir-302 as mir-302-like gene silencing effectors for treating human tumors/cancers. Preferably, the mir-302-like gene silencing effector is transcribed from either a recombinant mir-302 family cluster (mir-302s; hybrid of SEQ.ID.NOs.9-16) or a manually re-designed mir-302 shRNA homologue (i.e. hybrid of SEQ.ID.NOs.17 and 18). The treated cells may express the mir-302 targeted cellular genes either in vitro, ex vivo or in vivo. By silencing the mir-302-targeted cellular genes, the present invention is able to not only suppress tumor/cancer cell tumorigenecity but also reprogram high-grade malignant cancer cells to a more benign low-grade state, a phenomenon called cancer regression.

Using the present invention, we have evidenced the success of a mir-302-mediated anti-tumor/cancer therapy. First, it is safe to normal human cells. As shown in FIGS. 1E-F and FIGS. 3A-B, transfection of mir-302 into normal human cells (mirPS-hHFC) causes minor cell cycle attenuation but not apoptosis or cell death. Second, transfection of mir-302 into human cells is able to reprogram the cells into a stem cell-like state, which is beneficial for healing damaged tissues (FIGS. 4A-B and FIGS. 5A-D). Third, transfection of mir-302 into human tumor/cancer cells (such as prostate cancer PC3, skin cancer Colo, breast cancer MCF7, liver cancer HepG2, and neoplastic teratocarcinoma NTera-2) all showed a strong inhibitory effect on tumor/cancer cell growth and caused >98% cell death or apoptosis (FIGS. 6A-D and FIGS. 12A-C). Fourth, mir-302 can inhibit tumorigenecity not only through co-suppression of multiple cell cycle regulators, such as CDK2, cyclin D1/D2 and BMI-1, but also via activation of tumor suppressors, such as p16INK4a and p14/p19Arf (FIGS. 7B-D). Last, In vivo delivery of mir-302 into tumors/cancers can inhibit >90% tumor/cancer cell growth (FIGS. 8A-C and FIG. 15). In addition, mir-302 does not cause cell senescence through telomere shortening (FIGS. 9A-C). Notably, we have successfully formulated and delivered both of the mir-302-like gene silencing effector and its expression vector into targeted tumors/cancers in vivo, preventing the risks of retroviral infection and transgenic mutation (FIGS. 8A-C and FIG. 15). These findings provide strong evidence for using mir-302-like gene silencing effectors as a therapeutic drug and/or vaccine for anti-tumor/cancer therapy. Given that mir-302 may also function to repair and regenerate damaged human tissues (Lin et al., 2008 and 2010), the present invention may provide further beneficial applications in not only anti-tumor/cancer therapy but also tissue recovery and/or organ regeneration.

BRIEF DESCRIPTION OF THE DRAWINGS

The patent or application file contains at least one color drawing. Copies of this patent or patent application publication with color drawing will be provided by the USPTO upon request and payment of the necessary fee.

Referring particularly to the drawings for the purpose of illustration only and not limitation, there is illustrated:

FIGS. 1A-F show inducible mir-302 expression and its effect on normal human hair follicle cell (hHFC) proliferation. (A) Construct of the Dox-inducible pTet-On-tTS-miR302s vector. (B) Structure of the mir-302 familial cluster (mir-302s). (C) MiRNA microarray analysis of induced mir-302 expression at 6 hours after 10 μM Dox treatment (n=3, p<0.01). (D) Northern and western blot analyses of the dose-dependent mir-302 effect on the expression patterns of core reprogramming factors Oct3/4-Sox2-Nanog and melanocytic marker genes TRP1 and cytokeratin 16 (n=5, p<0.01). (E) Bar charts of flow cytometry analyses showing the dose-dependent mir-302 effect on the changes of mitotic (M phase) and dormant (G0/G1 phase) mirPS-hHFC populations. (F) Mir-302-induced apoptotic DNA laddering effects after treatment of 10 μM Dox in various mirPS cell lines.

FIGS. 6A-E show in vitro tumorigenecity assays of various tumor/cancer-derived mirPS cells in response to mir-302 expression induced by 10 μM Dox. (A) and (B) Changes of cell morphology and cell cycle rate before and after Dox-induced mir-302 expression. Each cell DNA content respective to cell cycle stages was shown by a chart of flow cytometry analysis above the cell morphology (n=3, $p<0.01$). (C) Bar charts of flow cytometry analyses showing the dose-dependent mir-302 effect on the changes of mitotic (M phase) and dormant (G0/G1 phase) cell populations of various tumor/cancer-derived mirPS cells. (D) Functional analysis of mir-302-suppressed tumor invasion in Matrigel chambers (n=4, $p<0.05$). (E) Comparison of cell adhesion to the hBMEC monolayer before and after Dox-induced mir-302 expression (n=4, $p<0.05$).

DETAILED DESCRIPTION OF THE INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention provides a novel nucleic acid composition and method for inhibiting the proliferation and tumorigenecity of human tumor/cancer cells, using recombinant mir-302-like gene silencing effectors. Unlike previous shRNA designs, the presently invented shRNAs may contain a mismatched stem-arm similar to the precursors of native mir-302 (pre-mir-302). Further, the presently invented shRNAs may also contain an improved pre-mir-302 stem-loop, such as 5'-GCTAAGCCAG GC-3' (SEQ.ID.NO.1) and 5'-GCCTGGCTTA GC-3' (SEQ.ID.NO.2), which can provide the same nuclear export efficiency as native pre-miRNAs but not interfere with the tRNA exportation. Without being bound by any particular theory, such an anti-proliferative and anti-tumorigenetic effect of the present invention is directed to a newly discovered mir-302-mediated gene silencing mechanism, triggered by transfection of a recombinant nucleic acid composition capable of expressing either a mir- 302 family cluster (mir-302s) or a mir-302-homologous shRNA. All of the manually re-designed mir-302 miRNA/shRNA molecules possess an identical 5'-end in their first 17 nucleotides, 5'-UAAGUGCUUC CAUGUUU-3' (SEQ.ID.NO.3). The protocols for constructing the mir-302-like gene silencing effectors and the nucleic acid composition expressing mir-302 are described in Examples 2 and 3. In design of sequences homologous to mir-302, thymine (T) can be used in place of uracil (U).

Figure 1A:
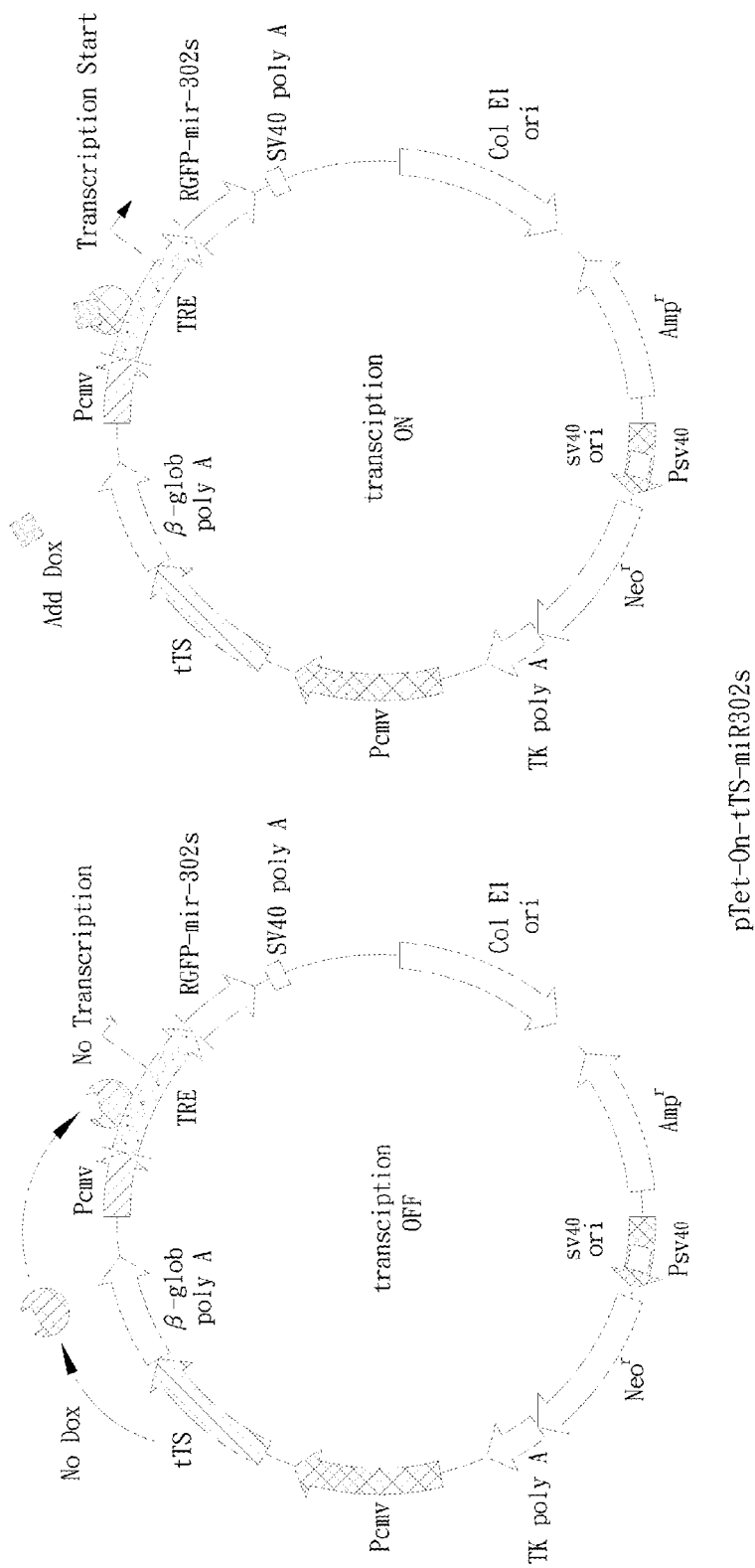
Figure 1C:
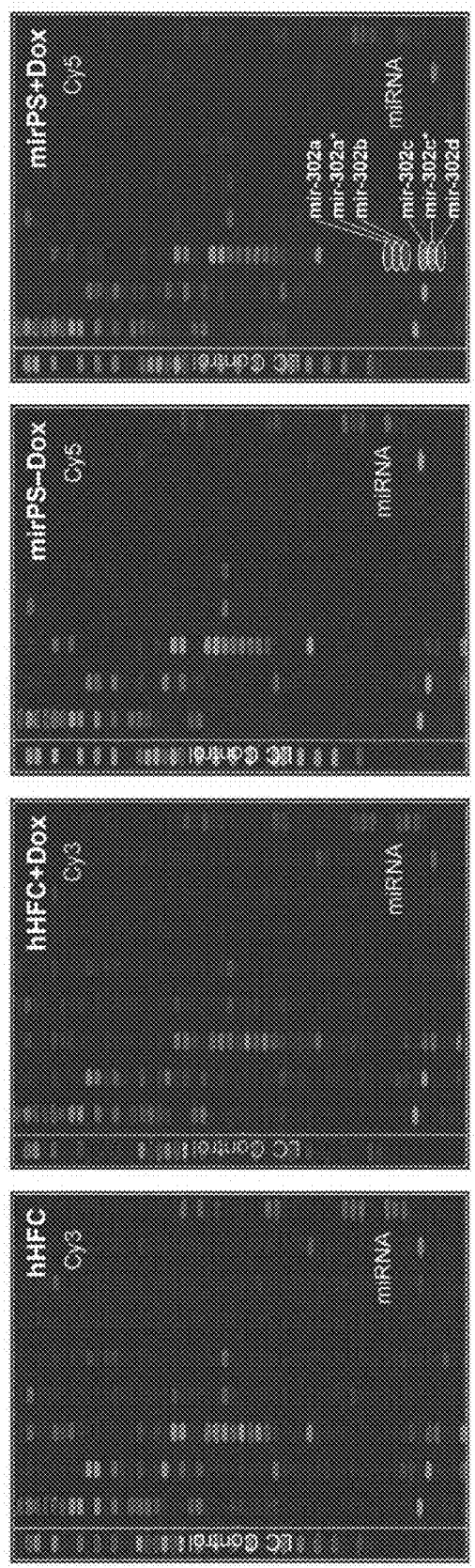
Figure 2A:
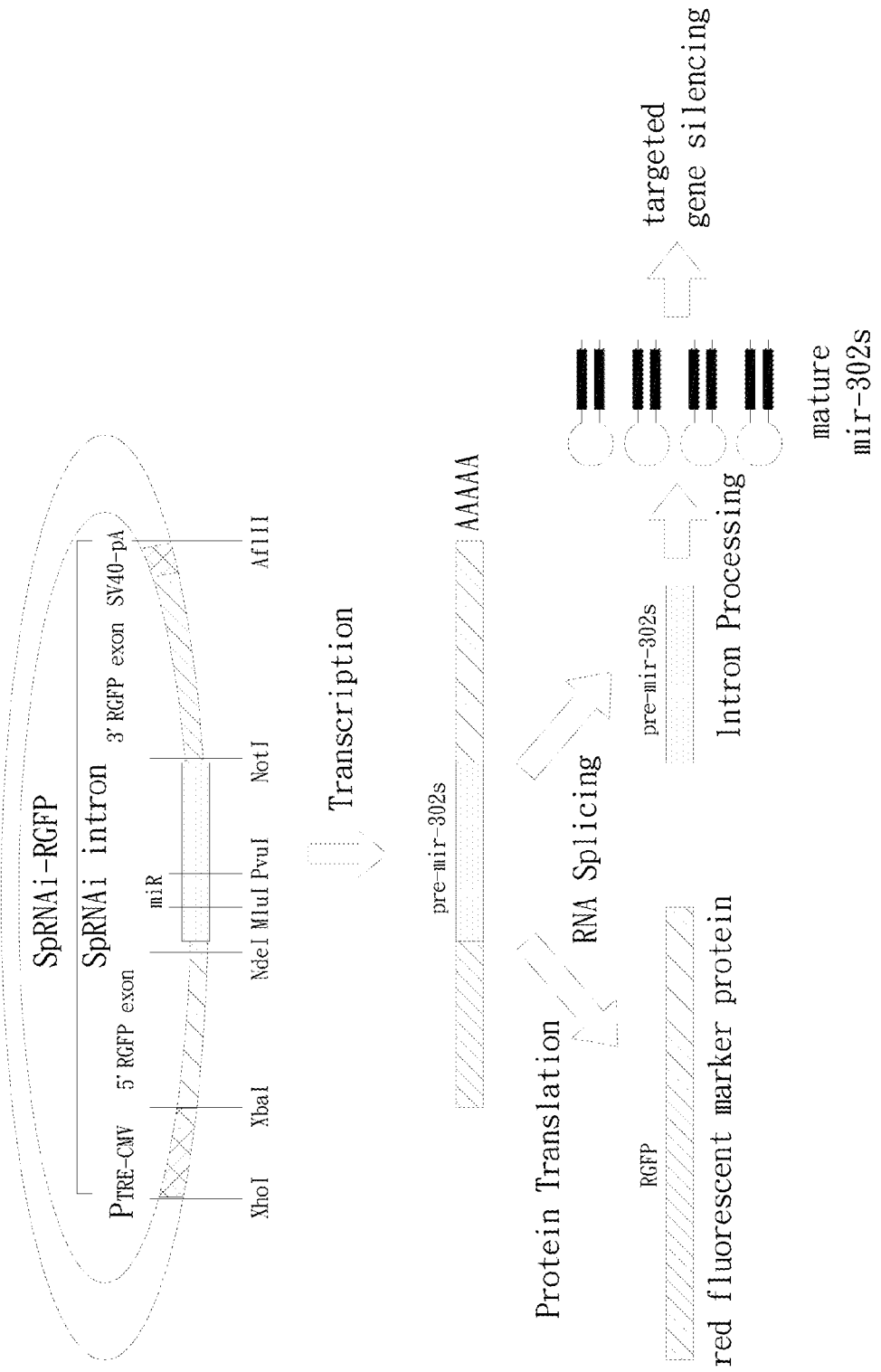
FIGS. 2A-C depict the biogenesis of mir-302s and generation of mirPS cells. (A) Mechanism of intronic mir-302 biogenesis. The mir-302 familial cluster was transcribed with a gene encoded for red fluorescent protein (RGFP) and then further spliced into individual mir-302 members by spliceosomal components and cytoplasmic RNaseIII Dicers, while the RGFP served as a indicator for mir-302 production. One fold RGFP concentration equaled to four folds the mir-302 concentration. (B) and (C) Schematic procedure for mir-302 transfection with liposome/polysome/electroporation. The inducible mir-302-expressing pTet-On-tTS-miR302s vector (FIG. 1A) was transduced into adult hHFC by electroporation at 300-400 volts for 150 μsec in a hypo-osmolar PH buffer (200 μl; Eppendorf). In each test, 10 μg of the pTet-On-tTS-miR302s vector was used to transfect 200,000 cultured hHFC derived from as few as two human hair follicles (dermal papillae). After doxycycline (Dox)-induced expression, the biogenesis of mir-302 relied on the natural intronic miRNA pathway.
Figure 2B:
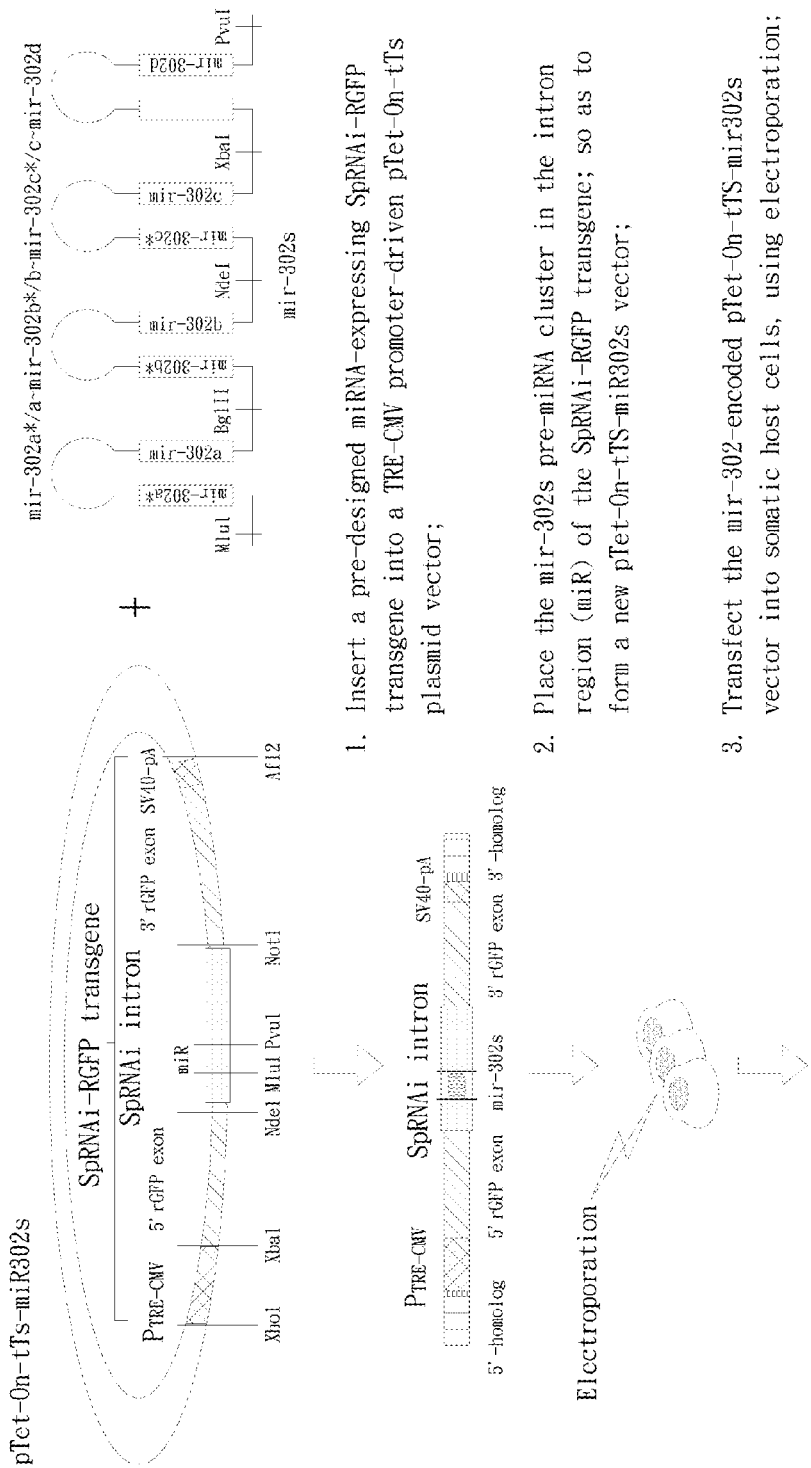
Figure 2C:
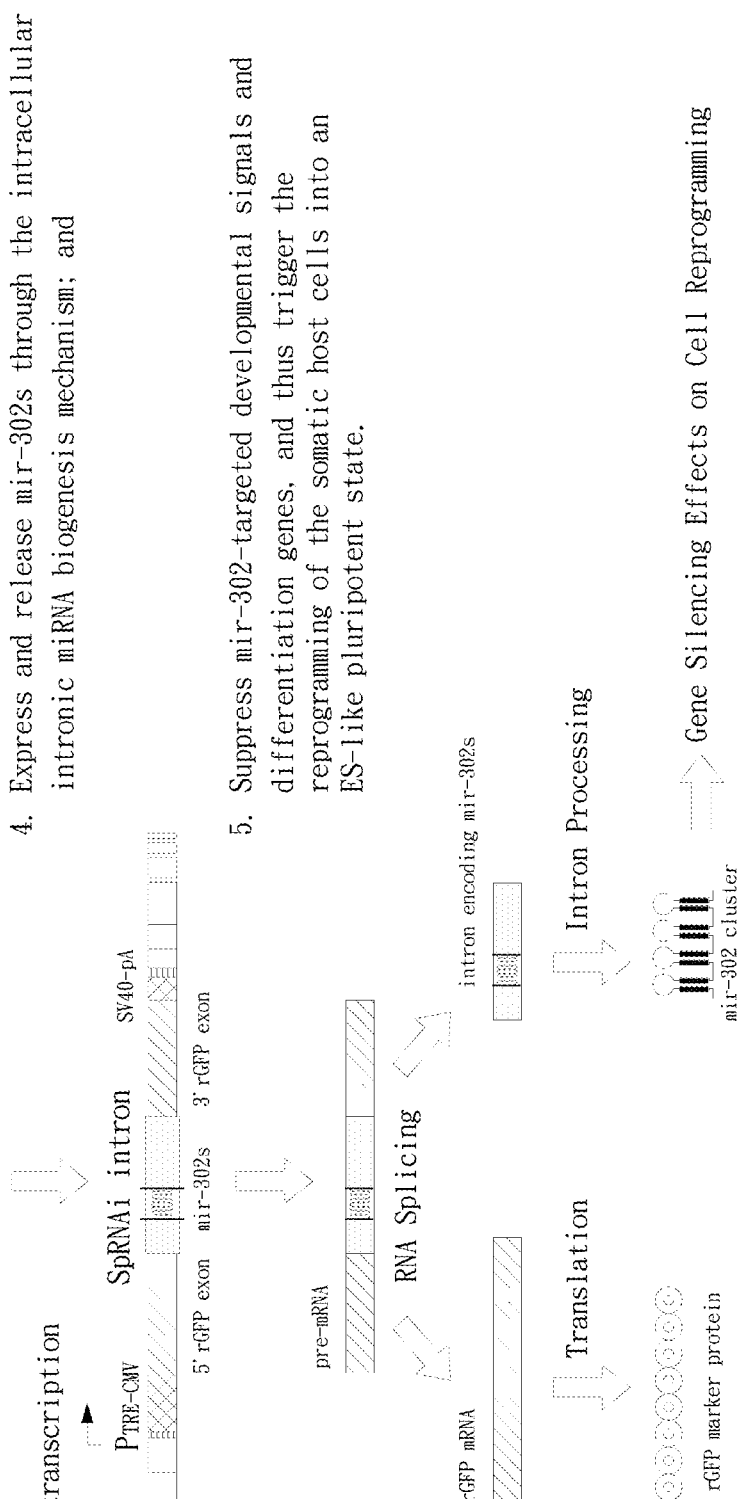

To address the mechanistic role of mir-302 in human cell cycle, we designed an inducible pTet-On-tTS-miR302s expression vector (FIG. 1A; Example 2) to transfect normal and cancerous human cells. Mir-302 is a hES-specific microRNA (miRNA) family that consists of four small non-coding RNA members, mir-302b, c, a, and d, in one cluster (mir-302s; FIG. 1B) (Suh et al., 2004). In our design, the expression of mir-302s was driven by a tetracycline-response-element (TRE)-controlled cytomegaloviral (CMV) promoter in response to doxycycline (Dox) stimulation. After transfection, the biogenesis of mir-302 followed the natural intronic miRNA pathway, in which mir-302s was transcribed with a reporter gene encoded for red fluorescent protein (RGFP) and then further spliced into individual mir-302 members by spliceosomal components and cytoplasmic RNaseIII Dicers (FIG. 2A) (Lin et al., 2008). For quantification measurement, one fold RGFP concentration equaled to four folds the mir-302 concentration. MiRNA microarray analysis confirmed that all mir-302 members except mir-302b* were efficiently expressed in transfected cells after Dox stimulation (FIG. 1C; Example 3). The procedure for transfecting cells with the pTet-On-tTS-miR302s expression vector is summarized in FIGS. 2B-2C.

Moreover, the mir-302-expressing nucleic acid composition, such as pTet-On-tTS-miR302s, may contain a Kozak consensus translation initiation site to increase translation efficiency in eukaryotic cells, multiple SV40 polyadenylation signals downstream of the mir-302-expressing construct, a pUC origin of replication for propagation in prokaryotic cells, at least two restriction sites for incorporation of the mir-302-expressing construct (i.e. SpRNAi-RGFP) into the nucleic acid composition, an optional SV40 origin for replication in mammalian cells that express the SV40 T antigen, and an optional SV40 early promoter for expressing an antibiotic resistance gene in replication-competent prokaryotic cells. The expression of antibiotic resistance genes is used to serve as a selective marker for isolating positive clones with the transgene expression. The antibiotics are selected from the group consisted of G418, neomycin, puromycin, penicillin G, ampicillin, kanamycin, streptomycin, erythromycin, spectromycin, phophomycin, tetracycline, doxycycline, rifapicin, amphotericin B, gentamycin, chloramphenicol, cephalothin, tylosin, and a combination thereof.

Mir-302 Attenuates the Normal Cell Cycle Rate without Causing Apoptosis

Figures 1D, 1E:
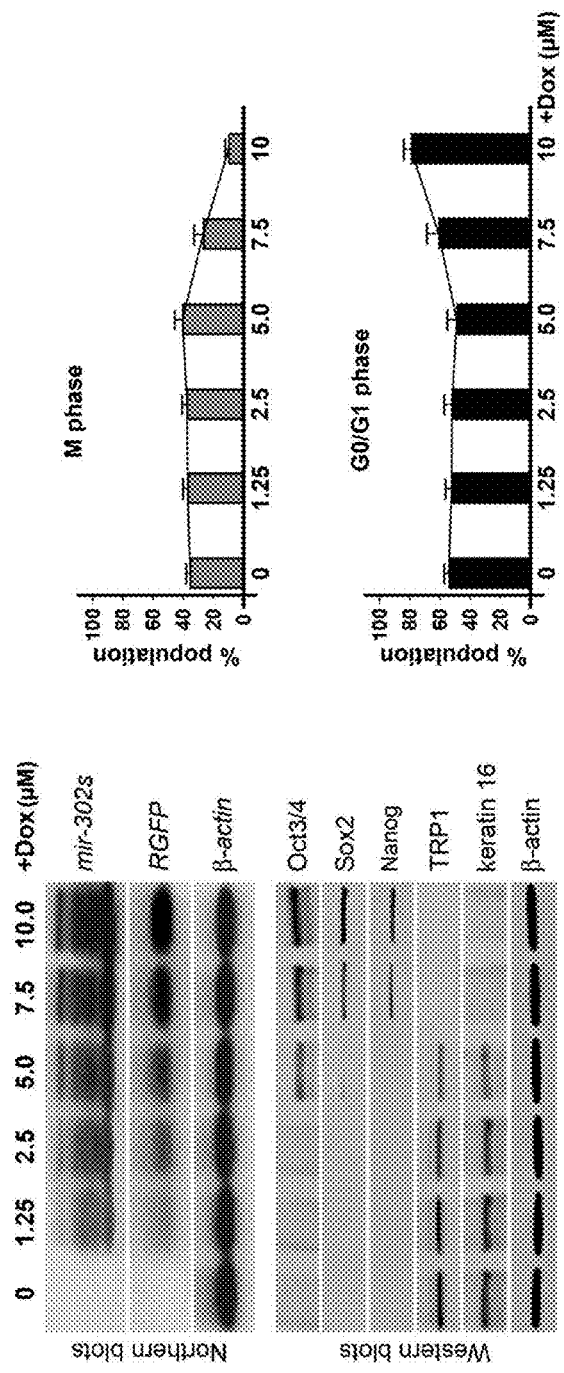
Figure 1F:
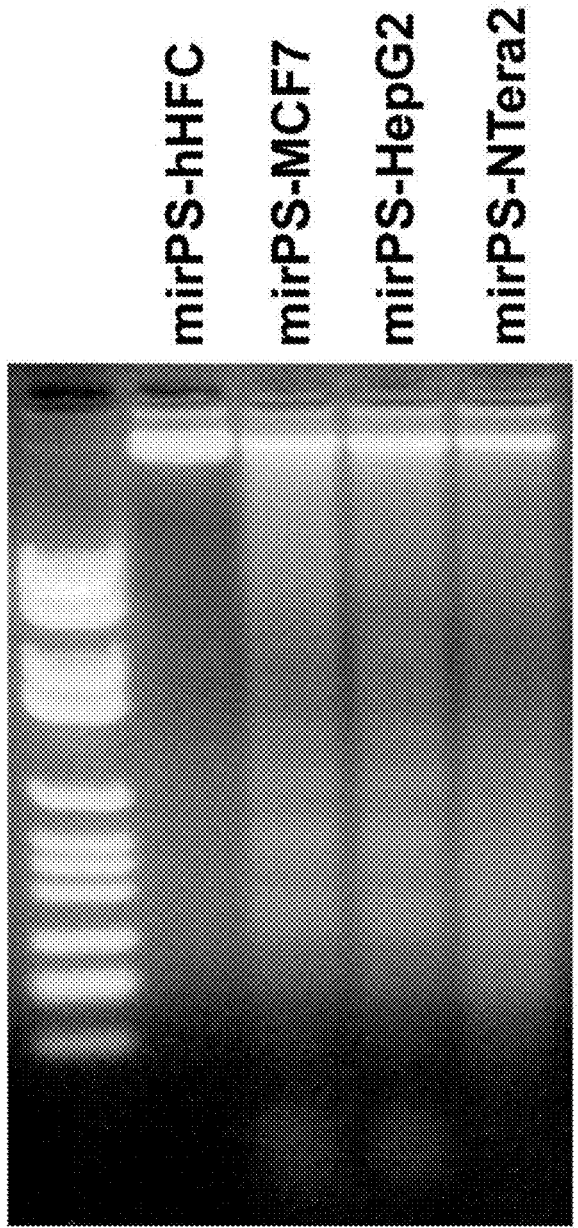

Our previous studies have shown that increasing mir-302 expression in human melanoma Colo-829 and prostate cancer PC3 cells reprogrammed these malignant cancer cells into a hES-like pluripotent state (Lin et al., 2008). During this somatic cell reprogramming (SCR) process, mir-302 caused apoptosis in >98% of the cancer cell population and greatly reduced the proliferation rate of the remaining (<2%) reprogrammed cells. Although this feature may benefit cancer therapy, it is uncertain how mir-302 functions in normal human cells. To evaluate this effect, we introduced the inducible pTet-On-tTS-miR302s expression vector into normal human hair follicle cells (hHFCs). hHFCs were chosen due to their abundance, accessibility and fast growth. Following an increase of Dox concentration up to 10 μM, we observed that the core reprogramming factors Oct4-Sox2-Nanog were concurrently stimulated by a threshold of Dox>7.5 μM (FIG. 1D; Example 5) and meanwhile the proliferative cell population was reduced by 70% from 37%±2% to 11%±2% (FIG. 1E, M phase; Example 7). Accordingly, the dormant cell population was increased by 41% from 56%±3% to 79%±15% (FIG. 1E, G0/G1 phase; Example 7), reflecting a strong anti-proliferative effect similar to our previous observation in mir-302-reprogrammed pluripotent stem cells (mirPS cells; Lin et al., 2008). However, the mir-302-reprogrammed hHFC cells (mirPS-hHFC) did not display any detectable sign of apoptotic DNA laddering or cell death (FIG. 1F; Example 6), indicating that normal cells are more tolerable than tumor/cancer cells to the anti-proliferative effect of mir-302. It is conceivable that tumor/cancer cells are very difficult to survive in such a dormant state due to their high metabolism and rapid growth expansion.

Figure 3A:
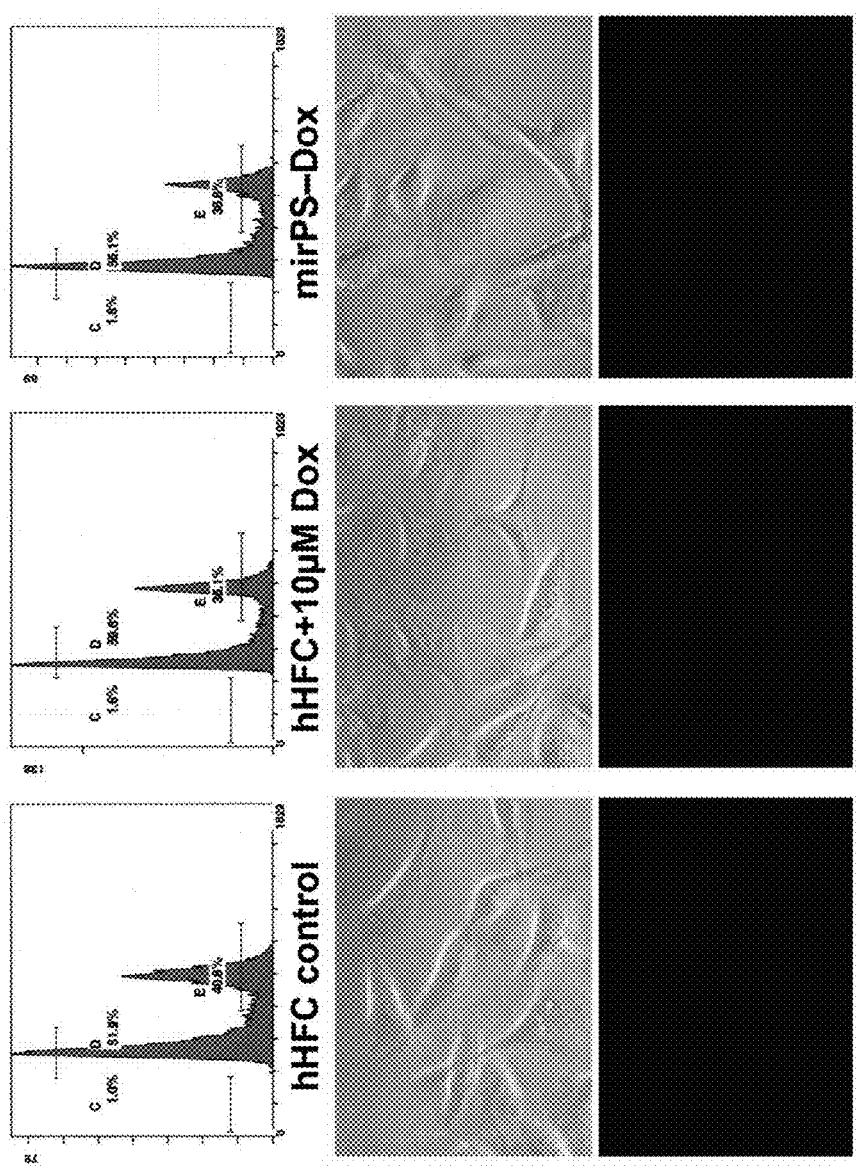
FIGS. 3A-C show the changes of mirPS-hHFC cell properties by Dox-induced mir-302 expression (Dox=5 or 10 μM). (A) and (B) Changes of cell morphology and cell cycle rate before and after Dox-induced reprogramming. Each cell DNA content respective to cell cycle stages was shown by a chart of flow cytometry analysis above the cell morphology (n=3, $p<0.01$). The first (left) and second (right) peaks of the charts represented the ratios of resting G0/G1 and mitotic M phase cells in the entire tested cell population, respectively. Scale bars=100 μm. (C) Time-course formation of embryoid body (EB) from a single mirPS-hHFC cell after limiting dilution. The cell cycle was estimated to be approximately 20-24 hours at start but gradually accelerated after 72 hours. Scale bars=100 μm.
Figure 3B:
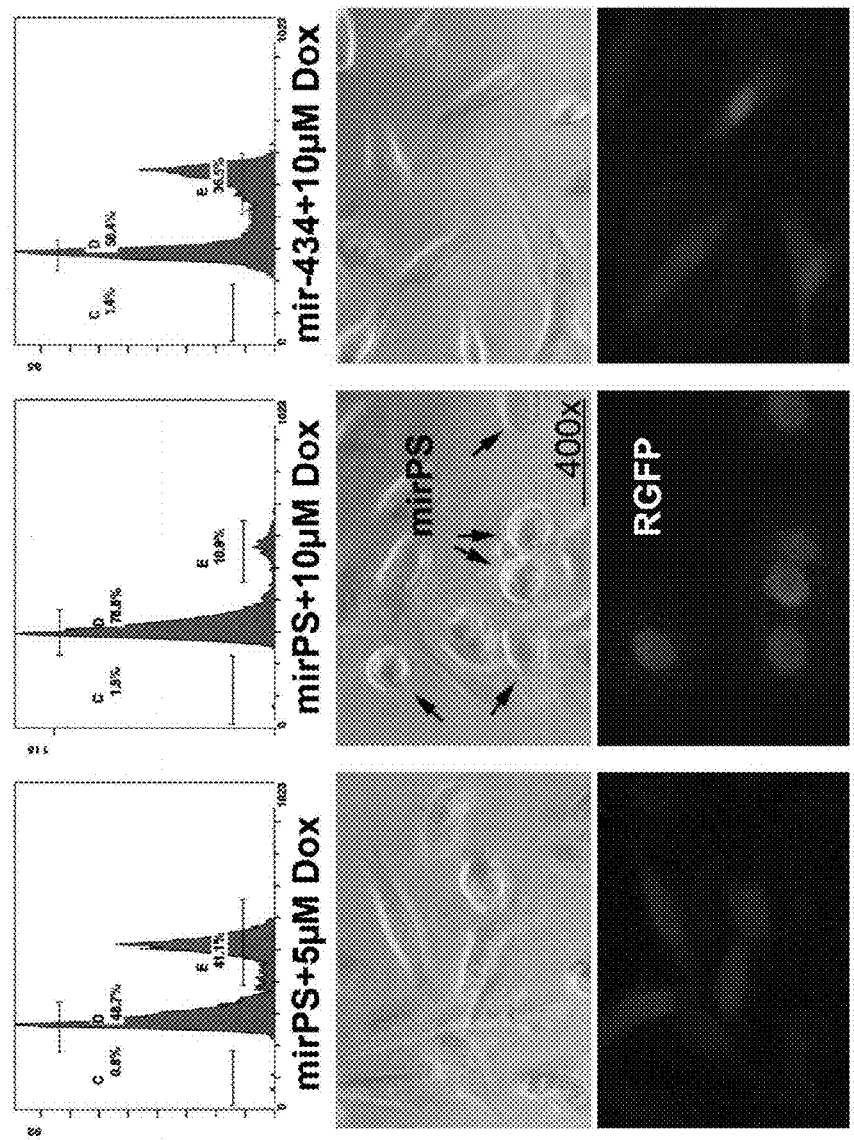
Figure 3C:
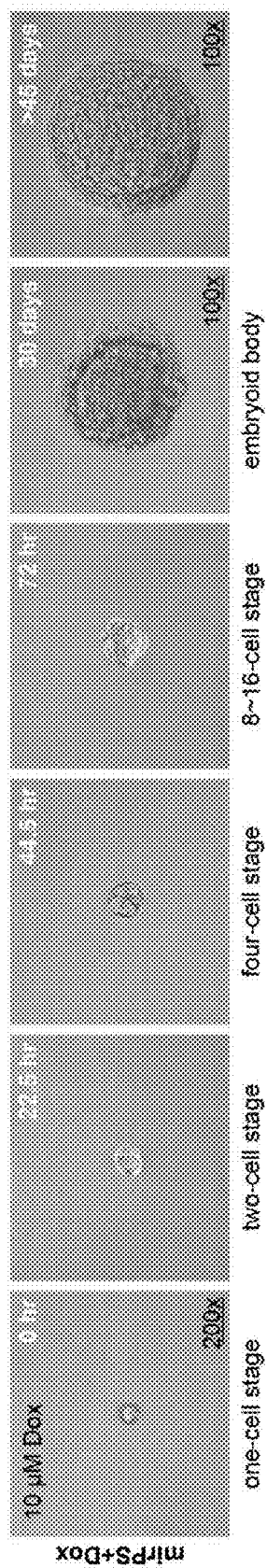
Figure 4A:
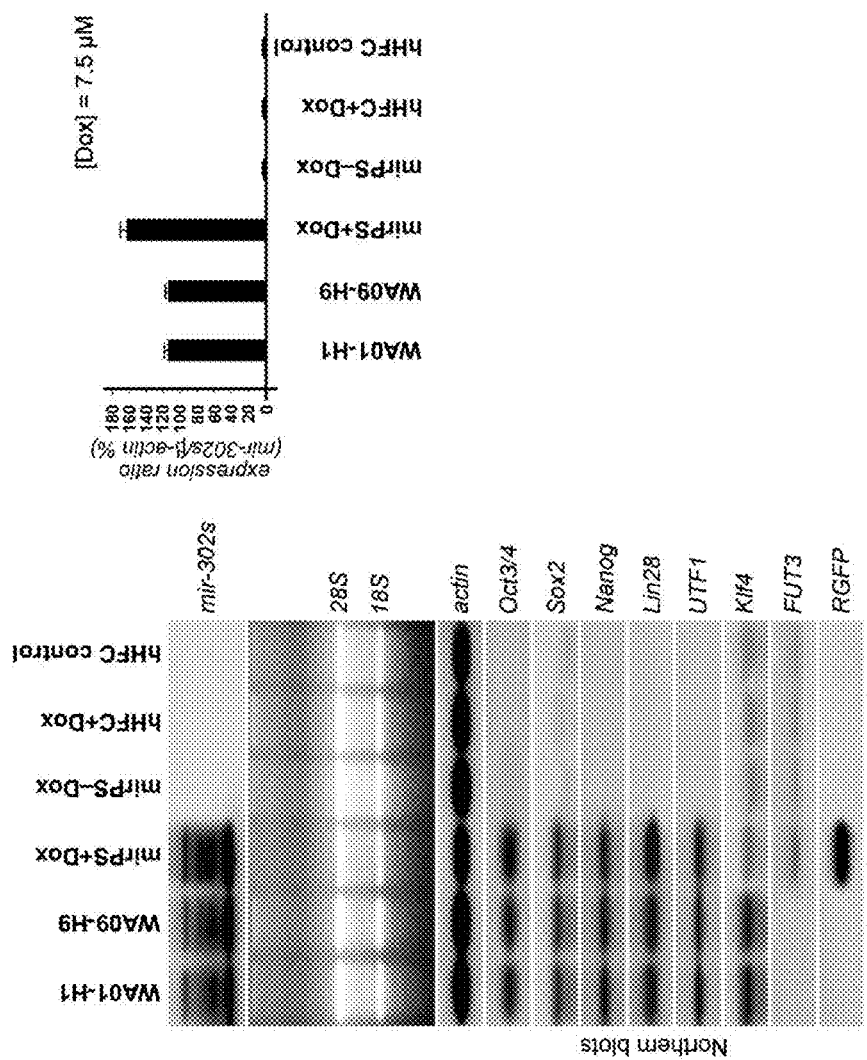
FIGS. 4A-B show analysis of pluripotent marker expression and in vivo pluripotent differentiation/assimilation. (A) Northern blot analysis of hES marker gene expression patterns induced by a high mir-302 concentration in mirPS cells compared to those in hES WA01-H1 (H1) and WA09-H9 (H9) cells (n=5, $p<0.01$). After treatment of 7.5 μM Dox, mir-302 concentration was raised to over 30% higher than that of H1 and H9 cells (>30 fold higher than untreated hHFCs) and began inducing co-expression of the major pluripotent markers Oct3/4, Sox2, Nanog, Lin28 and undifferentiated embryonic cell transcription factor 1 (UTF1). (B) Assimilation of mirPS cell-differentiated tissues into the surrounding tissues around the injection sites of immunocompromised SCID-beige mice one week after the implantation. White arrows indicated the direction of injection. Intercalated disks were marked by yellow triangles. The mirPS-hHFC-derived tissue cysts were not grown in mouse organs/tissues other than uterus and peritoneal cavity. In view of this, we further dissected and examined the surrounding tissue formation around the injection sites one week after the implantation. One day prior to dissection, the mice were treated with 10 μg Dox by tail vein injection. We observed that the RGFP-positive mirPS cells differentiated into the same cell types as the surrounding tissues in the implanted sites, including gut epithelium after intraperitoneal injection, cardiac muscle after heart puncture, and skeleton muscle by dorsal flank injection. Not only that, the assimilated mirPS cells also expressed the same tissue-specific makers as the surrounding tissues, such as MUC2 for gut epithelium, troponin T type 2 (cTnT) for cardiac muscle, and myosin heavy chain (MHC) for skeleton muscle.
Figure 4B:
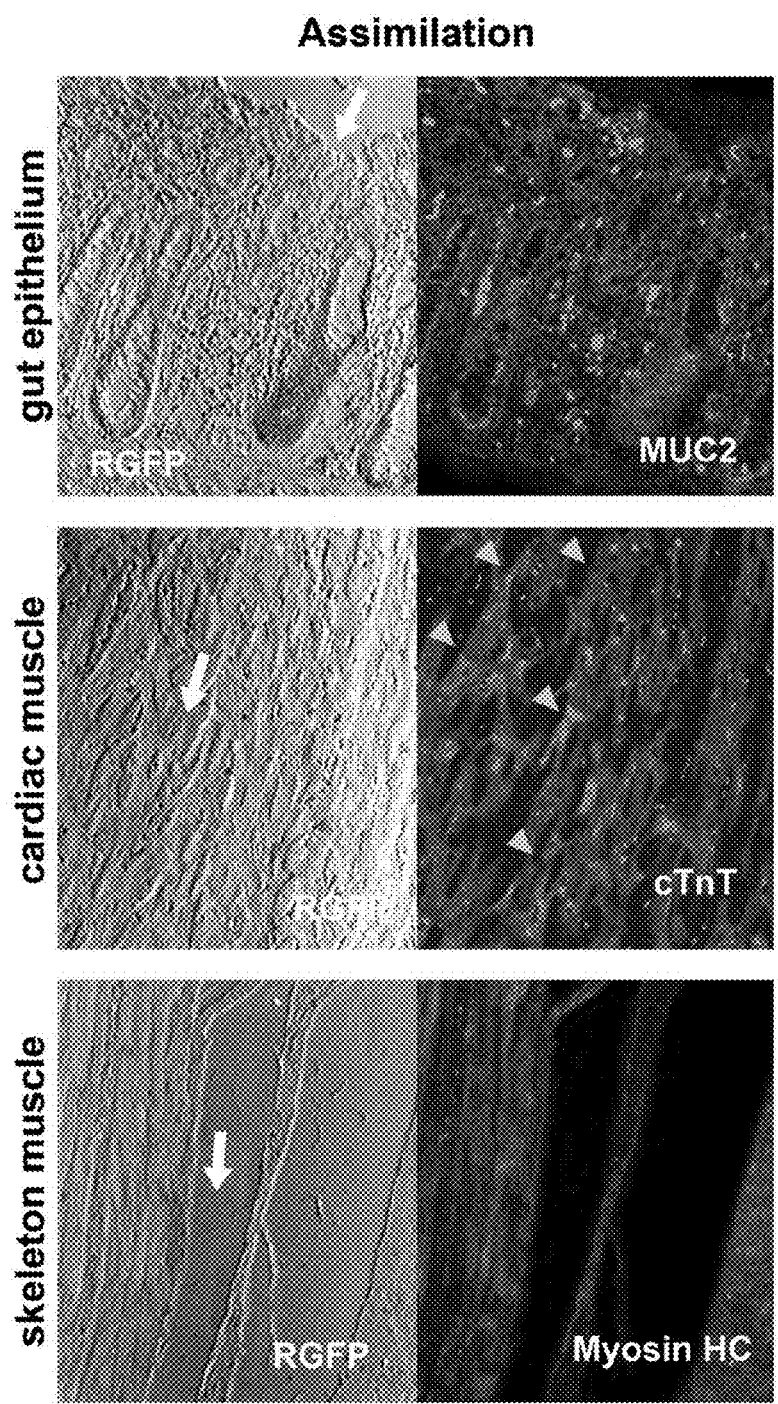
Figure 5A:
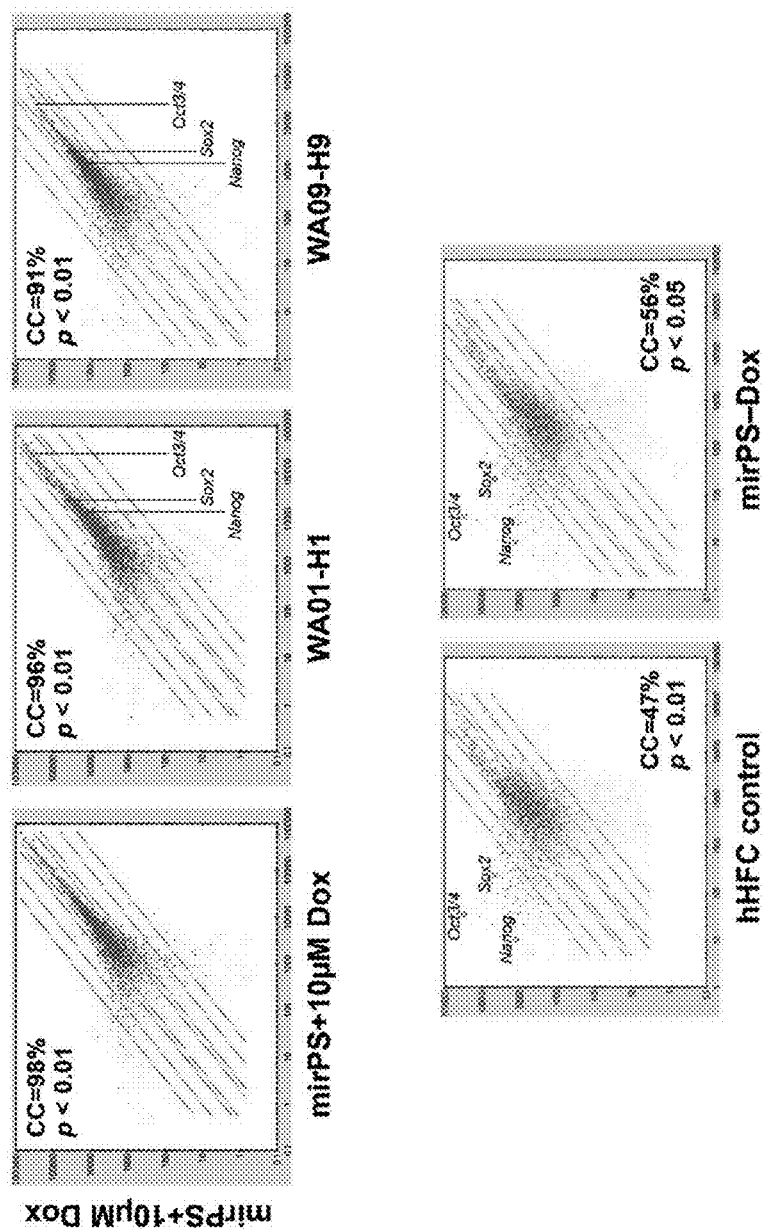
FIGS. 5A-D show gain of hES-like properties in Dox-induced mirPS-hHFCs (Dox=10 μM). (A) Analysis of global gene expression patterns before and after mir-302-induced somatic cell reprogramming (SCR), using human genome GeneChip U133 plus 2.0 arrays (Affymetrix; n=3, $p<0.01$-0.05). (B) HpaII cleavage showing the vast loss of global CpG methylation, identified by increased presence of smaller DNA fragments, at a genome-wide scale in mirPS cells treated with 10 μM but not 5 μM Dox. (C) Bisulfite DNA sequencing in the promoter regions of Oct3/4 and Nanog, showing the detailed methylation maps. Black and white circles indicate the methylated and unmethylated cytosine sites, respectively. (D) Pluripotent differentiation of mirPS-hHFCs into teratoma-like tissue cysts, containing various tissues derived from all three embryonic germ layers.

Most notably, when treated with Dox>7.5 μM, mirPS-hHFC morphology was changed from a spindle to a sphere shape, resembling a dormant cell (FIGS. 3A-3B, red RGFP-positive cells). The cellular mir-302 concentration stimulated by 7.5 μM Dox was approximately 1.3 folds the level in the hES H1 and H9 cells (FIG. 4A; Example 4). At this higher level, mirPS-hHFCs strongly expressed Oct3/4, Sox2, Nanog, and other standard hES cell markers (FIG. 4A). Microarray analysis of global gene expression further showed that approximately half of the transcriptome changed from a somatic hHFC mode to a uniform hES-like expression pattern sharing an average of >93% similarity to that of H1/H9 cells (FIG. 5A; Example 8). Global genomic DNA demethylation, the first sign of SCR initiation, was also clearly detected in these mirPS-hHFCs identical to those demethylation patterns in H1/H9 cells (FIGS. 5B and 5C; Example 9). Moreover, each individual mirPS-hHFC cell could grow into a single embryoid body-like colony and the cell division rate was 20-24 hours per cycle consistent with the anti-proliferative effect of mir-302 (FIG. 3C). We particularly noted that these mirPS-hHFCs were pluripotent but not tumorigenetic because they formed teratoma-like tissue cysts only in the uteruses and peritoneal cavities of pseudopregnant immunocompromised SCID-beige mice. These teratoma-like cysts contained various tissues derived from all three embryonic germ layers, ectoderm, mesoderm and definitive endoderm (FIG. 5D; Example 10). Alternatively when xenografted into normal male mice, these mirPS-hHFCs were assimilated by the surrounding tissues and presented the same tissue makers, demonstrating a possible use for healing damaged tissues (FIG. 4B). Taken together, these findings suggest that mir-302 can reprogram somatic hHFCs to hES-like iPS cells. Given that Oct3/4 and Sox2 are crucial transcription factors for mir-302 expression (Marson et al., 2008; Card et al., 2008), mir-302 may be used in place of Oct3/4-Sox2 for inducing SCR.

Mir-302-induced SCR and cell cycle attenuation are two collateral events, depending on the mir-302 concentration. We noted that both events occur almost simultaneously at a mir-302 concentration over 1.3 folds the level in the hES H1/H9 cells, indicating that this specific concentration is the minimal threshold for initiating both events. Previous studies using a single mir-302 member or at a lower concentration equal to the level in H1/H9 cells failed to elicit these events. Also, we have shown that the mir-302 concentration induced by a lower 5 μM Dox cannot silence either the target sites of the reporter gene or the targeted G1-checkpoint regulators. Compared to the natural development, early embryonic cells before the morula stage (32-64 cell stage) often present a very slow cell cycle rate similar to that of mirPS cells. However, such cell cycle regulation is not found in blastocyst-derived hES cells. It is presumable that a lower mir-302 concentration in hES cytoplasm may fail to silence the targeted G1-checkpoint regulators and oncogenes. This may also explain why blastocyst-derived hES cells have dramatic proliferative ability and tend to form tumors. Thus, the present invention may be applied to reduce the tumorigenecity of hES cells for stem cell therapy.

Figure 6A:
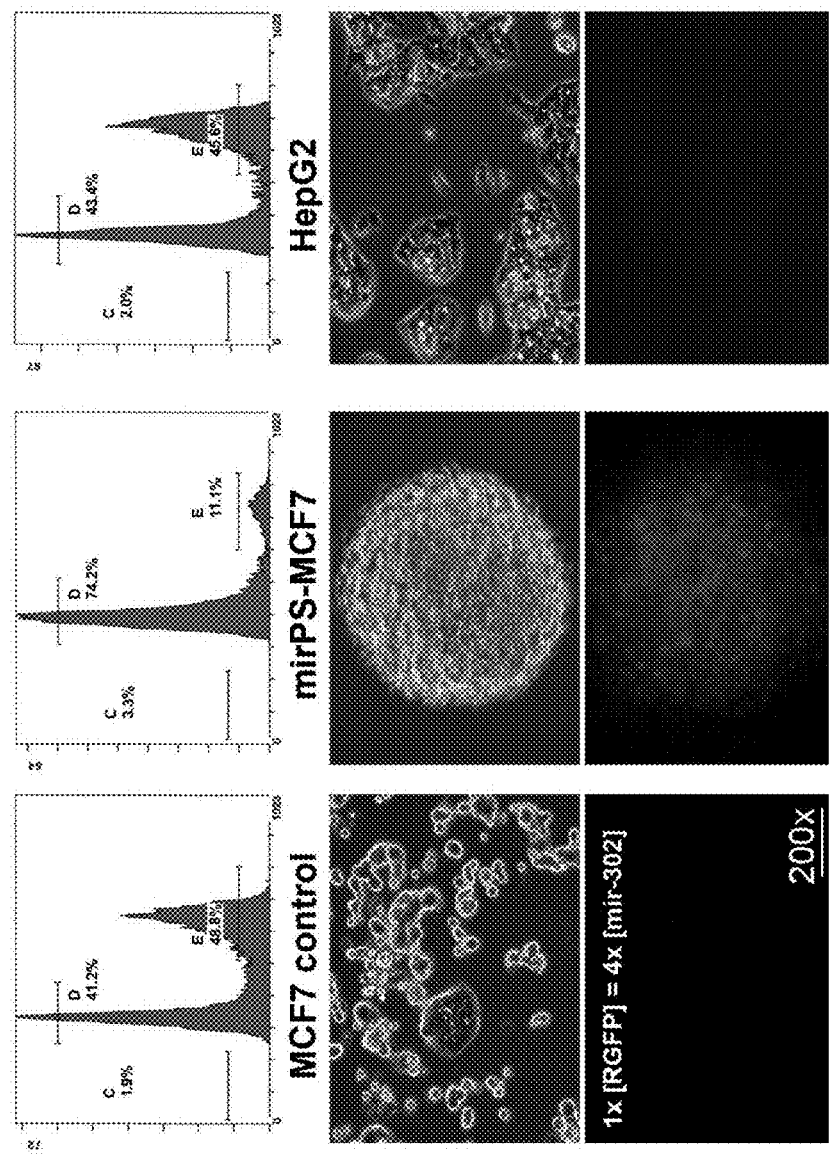
Figure 6B:
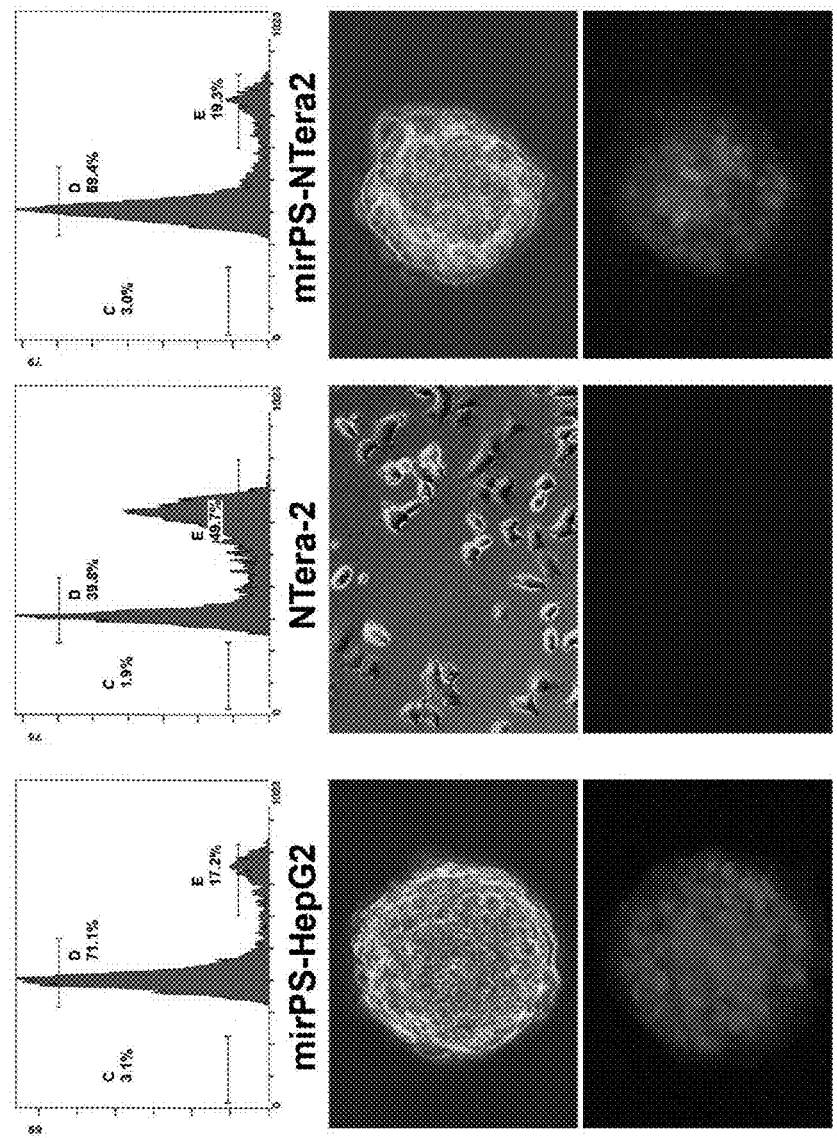

Mir-302 Inhibits Tumorigenecity and Causes Apoptosis in Various Tumor/Cancer Cells In view of mir-302 function in causing cancer cell apoptosis and cell cycle attenuation, we then investigated the possibility of using mir-302 as a universal drug to treat human tumor/cancer cells. As our previous studies have shown the feasibility of this approach in melanoma and prostate cancer cells (Lin et al., 2008), we further tested human breast cancer MCF7, hepatocellular carcinoma Hep G2, and embryonal teratocarcinoma Tera-2 (NTera-2) cells in the present invention. As shown in FIGS. 6A-6B, all three kinds of tumor/cancer cells were reprogrammed to dormant mirPS cells and formed embryoid body-like colonies after transfected with the pTet-On-tTS-miR302s vector stimulated by 10 µM Dox. Mir-302 at this level also induced significant apoptosis (>95%) in all three tumor/cancer cell types (FIG. 1F; Example 6). Flow cytometry analysis comparing DNA content to cell cycle stages, further showed a significant reduction in all of the mirPS mitotic cell populations (FIG. 6C; Example 7). The mitotic cell population (M phase) was decreased by 78% from 49%±3% to 11%±2% in mirPS-MCF7, by 63% from 46%±4% to 17%±2% in mirPS-HepG2, and by 62% from 50%±6% to 19%±4% in mirPS-NTera2 cells, whereas the resting/dormant cell population (G0/G1 phase) was increased by 80% from 41%±4% to 74%±5% in mirPS-MCF7, by 65% from 43%±3% to 71%±4% in mirPS-HepG2, and by 72% from 40%±7% to 69%±8% in mirPS-NTera2 cells, respectively. These results indicate that mir-302 can effectively attenuate the fast cell cycle rates and cause significant apoptosis in these tumor/cancer cells.

Figure 6E:
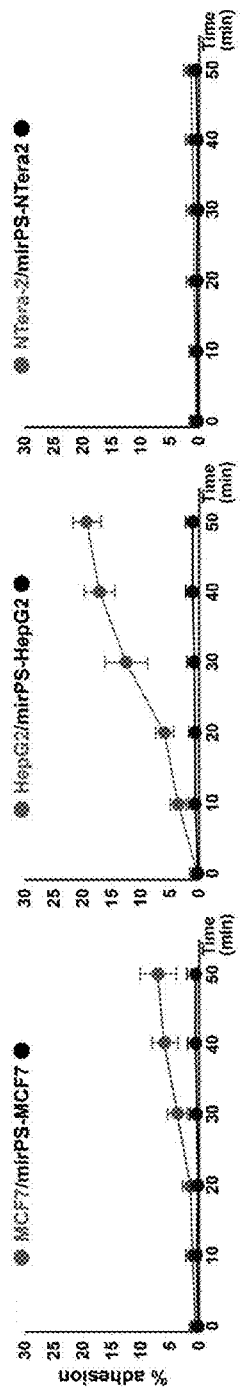

In vitro tumorigenecity assays, using Matrigel chambers (cell invasion assay) and cell adhesion to the human bone marrow endothelial cell (hBMEC) monolayer (cell adhesion assay), revealed two more anti-tumorigenetic effects of mir-302 in addition to its anti-proliferative feature. Cell invasion assay showed that all three dormant mirPS-tumor/cancer cells lost their ability to migrate (reduced to <1%) while the original tumor/cancer cells aggressively invaded into the chambered areas supplemented with higher nutrients, representing over 9%±3% of MCF7, 16%±4% of Hep G2 and 3%±2% of NTera-2 cell populations (FIG. 6D; Example 11). Consistently, cell adhesion assay also showed that none of these mirPS-tumor/cancer cells could adhere to hBMECs whereas a significant population of original MCF7 (7%±3%) and Hep G2 (20%±2%) cells quickly metastasize into the hBMEC monolayer after 50 min incubation (FIG. 6E; Example 12). In sum, all of the findings thus far strongly and repeatedly suggest that mir-302 is a human tumor suppressor capable of attenuating fast cell growth, causing tumor/cancer cell apoptosis, and inhibiting tumor/cancer cell invasion as well as metastasis. Most importantly, this novel mir-302 function may offer a universal treatment against multiple kinds of human cancers/tumors, including but not limited in malignant skin (Colo-829), prostate (PC-3), breast (MCF7) and liver (HepG2) cancers as well as various tumors in view of the variety of different tissue types in teratomas (NTera-2).

Mir-302-Mediated Anti-Proliferation Functions Through Co-Suppression of CDK2, Cyclins-D1/D2 and BMI-1

Figure 7A:
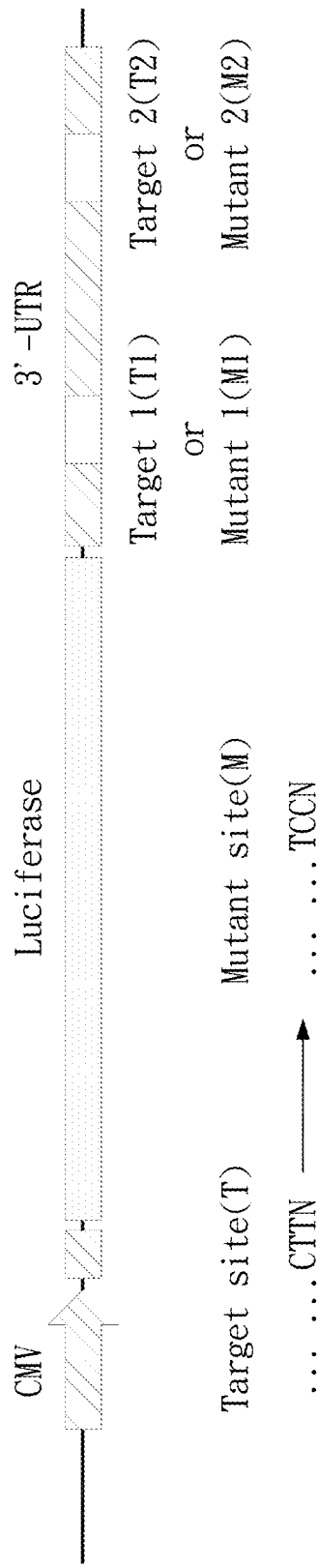
FIGS. 7A-D show luciferase 3'-UTR reporter assays of mir-302-induced gene silencing effects on targeted G1-checkpoint regulators. (A) Constructs of the luciferase 3'-UTR reporter genes, which carry either two normal (T1+T2) or two mutant (M1+M2), or a mixture of both (T1+M2 or M1+T2), mir-302 target sites in the 3'-UTR. The mutant sites contained a mismatched TCC motif in place of the uniform 3'-CTT end of the normal target sites. (B) Effects of Dox-induced mir-302 on the luciferase expression (n=5, $p<0.01$). Dox=5 or 10 μM. CCND1 and CCND2 refer to cyclin D1 and D2, respectively. (C) and (D) Western blot analyses showing the changes of major mir-302-targeted G1-checkpoint regulator induced by high (10 μM Dox) and low (5 μM Dox) mir-302 concentrations in mirPS cells compared to those found in hES H1 and H9 cells (n=4, $p<0.01$).
Figure 7B:
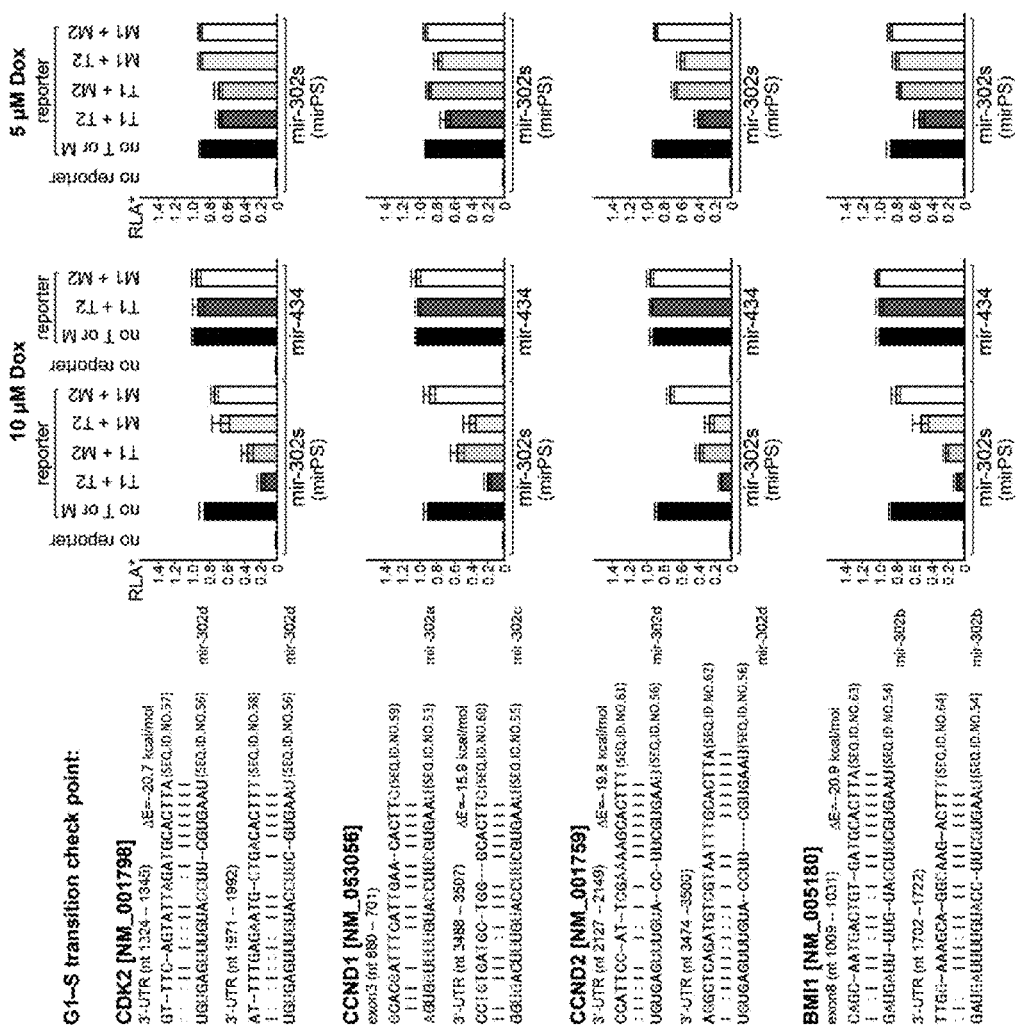
Figure 7D:
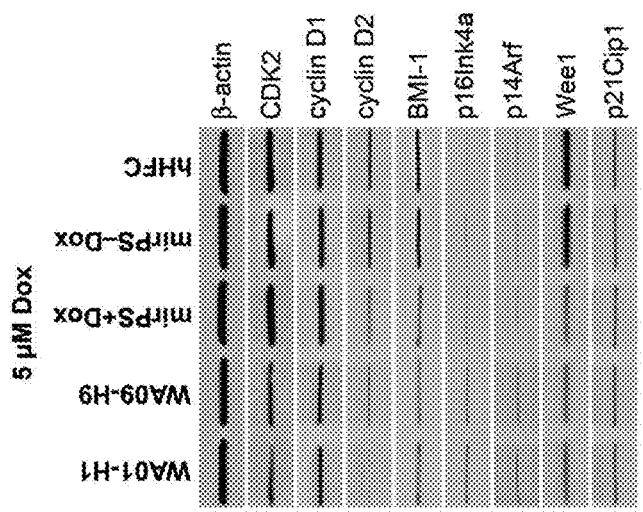

To validate the physical interactions between mir-302 and its targeted G1-checkpoint regulators, we used a luciferase 3'-untranslated region (3'-UTR) reporter assay (FIG. 7A; Example 15), which showed that treatments with various mir-302 concentrations resulted in very different inhibitory effects on the targeted G1-checkpoint regulators, including CDK2, cyclins-D1/D2 and BMI1 polycomb ring finger oncogene (BMI-1). In the presence of 10 µM Dox, mir-302 effectively bound to the target sites of CDK2, cyclins D1/D2 and BMI-1 transcripts and successfully silenced >80% of the reporter luciferase expression in all targets (FIG. 7B; Example 15). Suppression of the real target genes in mirPS cells was also confirmed by western blot analyses consistent with the results of the luciferase 3'-UTR reporter assay (FIG. 7C; Example 5). In contrast, a lower mir-302 expression induced by 5 µM Dox failed to trigger any significant silencing effect on either the target sites of the reporter gene or the targeted G1-checkpoint regulators, except cyclin D2 (FIGS. 7B and 7D), indicating that mir-302 fine-tunes the cell cycle rate in a dose-dependent manner. Given that the G1-S transition of mammalian cell cycle is normally controlled by two compensatory cyclin-CDK complexes, cyclin-D-CDK4/6 and cyclin-E-CDK2 (Berthet et al., 2006), we found that high concentrated mir-302 inactivated both complexes through simultaneous suppression of CDK2 and cyclins D1/D2, thus blocking both G1-S transition pathways and attenuating the cell cycle rate of the reprogrammed mirPS cells. In hHFCs and mirPS cells, cyclin D3 was expressed at a limited level insufficient to compensate the loss of cyclins D1/D2 in the mirPS cells.

Figure 7C:
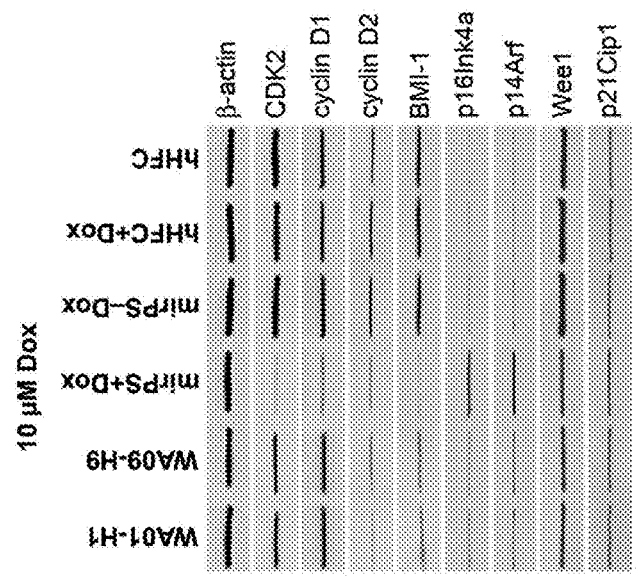

Accompanying BMI-1 silencing, we further detected a mild increase of p16Ink4a and p14Arf expression (gain 63%±17% and 57%±13% of the levels in hHFCs, respectively), whereas no change was found in p21Cip1 expression (FIG. 7C). Deficiency of BMI-1, an oncogenic cancer stem cell marker, has been shown to inhibit G1-S transition through enhancement of p16Ink4a and p14Arf tumor suppressor activities (Jacobs et al., 1999). In this scenario, 16Ink4a directly inhibits cyclin-D-dependent CDK4/6 activity in the phosphorylation of retinoblastoma protein Rb and thus prevents Rb from releasing E2F-dependent transcription required for S phase entry (Parry et al., 1995; Quelle et al., 1995). In addition, p14Arf prevents HDM2 from binding to p53 and permits the p53-dependent transcription responsible for G1 arrest or apoptosis (Kamijo et al., 1997). However, because embryonic stem cells are known to exempt from cyclin-D-dependent CDK regulation (Burdon et al., 2002; Jirmanova et al., 2002; Stead et al., 2002), current understanding of cell cycle regulation in hES cells has implicated CDK2 as the main determinant of the G1-S transition. As a result, the silencing of CDK2 likely contributes most of the G1-arrest efficacy in mirPS cells, while the co-suppression of cyclin-D and BMI-1 as well as co-activation of p16Ink4a and p14Arf may provide additional inhibition against tumorigenetic signal-induced cell proliferation. Furthermore, the loss of cyclin-D and activation of p16Ink4a may also explain the deficiency of cyclin-D-dependent CDK activity in embryonic stem cells.

Therefore, the stringency of miRNA-target gene interaction determines the real function of the miRNA. Depending on the cellular condition, miRNA may present different preferences in gene targeting. To this, the present invention provides insight into these important details and for the first time reveals that mir-302 functions very differently in human and mouse cells. In humans, mir-302 strongly targets CDK2, cyclins D1/D2 and BMI-1, but interestingly, not p21Cip1. Unlike mouse p21Cip1, human p21Cip1 does not contain any target site for mir-302. This different gene targeting leads to a significant schism between respective cell cycle regulations. In mES cells, mir-302 silences p21Cip1 and promotes tumor-like cell proliferation (Wang et al., 2008; Judson, 2009), whereas p21Cip1 expression is preserved in human mirPS cells and may cause slower cell proliferation and lower tumorigenecity. Additionally, mouse BMI-1 is not a target gene for mir-302 either due to lack of a proper target site. We have shown that silencing of human BMI-1 in mirPS cells slightly stimulates p16Ink4a/p14ARF expression to attenuate cell proliferation, whereas mir-302 cannot silence mouse BMI-1 to raise the same effect. Since p16Ink4a/p14ARF were elevated while p21Cip1 was not affected in mirPS cells, the anti-proliferative and anti-tumorigenetic effects of mir-302 in human cells most likely goes through p16Ink4a-Rb and/or p14/19ARF-p53 pathways in addition to the co-suppression of cyclin-E-CDK2 and cyclin-D-CDK4/6 pathways. These distinct targeting preferences of mir-302 to human and mouse genes imply that the mechanisms underlying their cell cycle regulations are fundamentally different.

Treatment of Mir-302 Eliminates >90% of Tumor Cell Growth In Vivo without Changing Stem Cell Pluripotency After identifying the tumor suppressor function of mir-302 and its different effects between normal and tumor/cancer cells, we tested the possible use of mir-302 as a drug for treating NTera2-derived teratomas in eight-week-old male athymic mice (BALB/c nu/nu strain) (Example 13). The neoplastic Tera-2 (NTera-2) cell line is a pluripotent human embryonal teratocarcinoma cell line that can differentiate into a variety of primitive somatic tissues in vivo, in particular primitive glandular and neural tissues (Andrews et al., 1984). Due to its pluripotency, NTera2-derived teratoma may serve as a model for treating various tumor types in vivo. For drug delivery, we adopted in situ injection of polyethylenimine (PEI)-formulated pCMV-miR302s expression vector in close proximity to the tumor site. The pCMV-miR302s vector was formed by changing the TRE-controlled CMV promoter to a regular CMV promoter (Example 2), of which the expression duration was approximately one month in human cells due to DNA methylation. By injecting up to 10 μg of the pCMV-miR302s vector per g mouse weight (the maximal amount of one shot injection in a mouse), we observed no signs of sickness or cachexia in the mice, indicating the safety of this approach. Histological examination also showed no detectable tissue lesions in brain, heart, lung, liver, kidney and spleen.

Figures 8A, 8B:
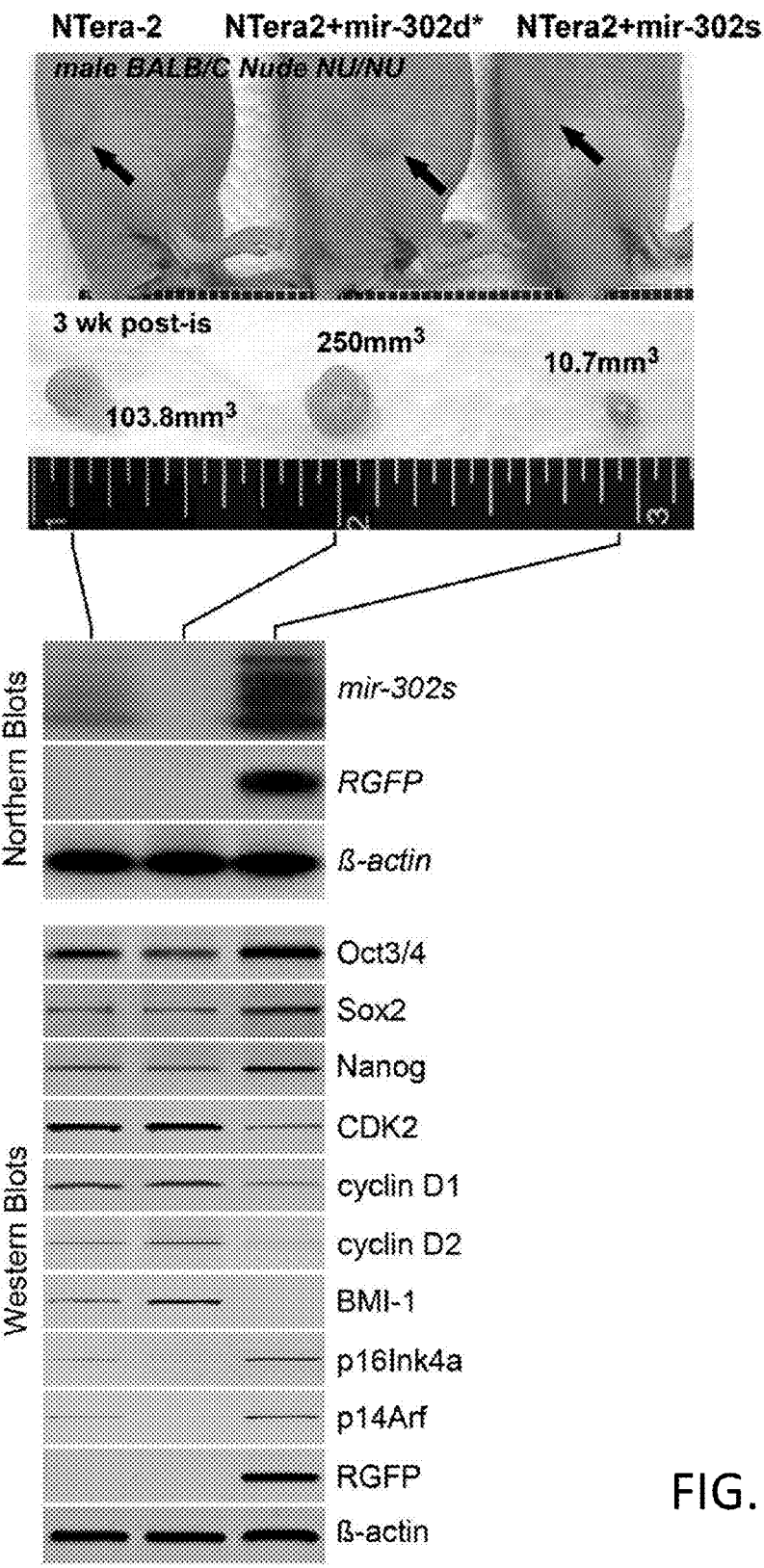
FIGS. 8A-C show in vivo tumorigenecity assays of neoplastic NTera-2 cells in response to either vector-based mir-302s (NTera2+mir-302s) or mir-302d* (NTera2+mir-302d*) expression (n=3, $p<0.05$). Mir-302s and mir-302d* were transcribed from the pCMV-miR302s and pCMV-miR302d* vectors in the transfected neoplastic Tera-2 (NTera-2) cells, respectively. (A) Morphological evaluation of average tumor sizes three weeks after the in-situ injection (post-is). All tumors were localized in the original implant sites (black arrows). No signs of cachexia or tumor metastasis were observed in all tested mice. (B) Northern and western blot analyses and (C) Immunohistochemical staining analyses of the in-vivo mir-302 effects on the expression patterns of core reprogramming factors Oct3/4-Sox2-Nanog and the mir-302-targeted G1-checkpoint regulators CDK2, cyclins D1/D2 and BMI-1 as well as p16Ink4a and p14Arf.
Figure 8C:
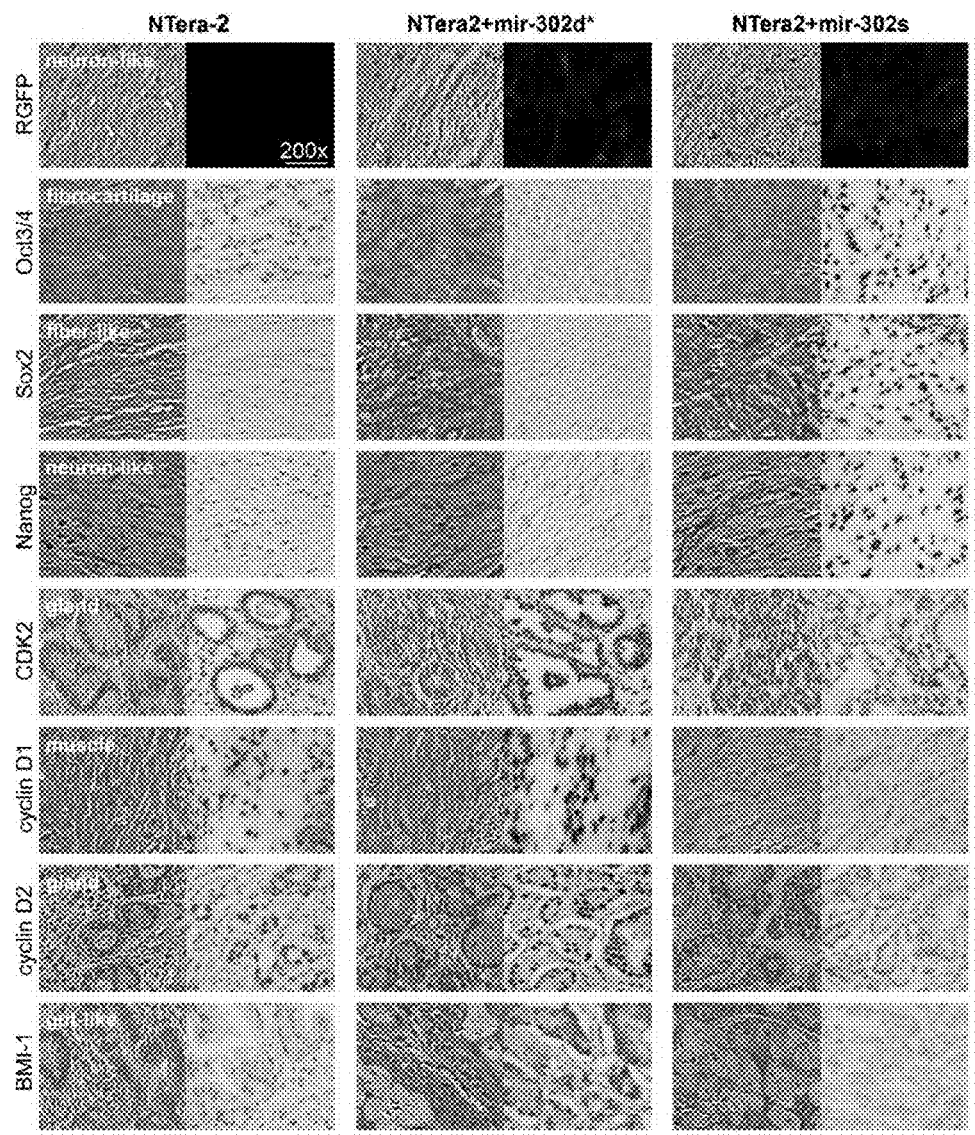

We detected a significant inhibitory effect on teratoma growth after five treatments (three-day intervals for each treatment) of 2 μg pCMV-miR302s vector (total 10 μg) per g mouse weight. As shown in FIG. 8A (Example 13), when treated with the pCMV-miR302s vector, the average size of NTera2-derived teratomas decreased by >89% (11±5 mm$^3$, n=6) compared to that of non-treated ones (104±23 mm$^3$, n=4). In contrast, treating the same amount of PEI-formulated antisense-mir-302d expression vector (pCMV-miR302d*) increased the teratoma sizes by 140% (250±73 mm$^3$, n=3). Based on that, NTera-2 cells were found to express a moderate level of mir-302 (FIG. 8B). Northern blotting also showed that mir-302 expression levels in these differently treated teratoma cells negatively correlated to the tumor sizes (FIG. 8B), suggesting that modulating mir-302 expression can effectively control the teratoma growth in vivo. To validate the previous findings in vitro, we performed western blotting to confirm the co-suppression of G1-checkpoint regulators CDK2-cyclins-D1/D2-BMI-1 and the co-activation of core reprogramming factors Oct3/4-Sox2-Nanog in the mir-302-treated teratomas (FIG. 8B). The same results were also confirmed by immunohistochemical (IHC) staining of these proteins in teratoma tissue sections (FIG. 8C; Example 14). Most noteworthily, we found that mir-302 inhibited teratoma cell growth without affecting its nature in pluripotent differentiation, indicating that high concentrated mir-302 plays a dual role as a tumor suppressor and a reprogramming factor. Based on this dual function of mir-302 and the consistent data in vitro and in vivo, we conclude that the same anti-proliferative mechanism of mir-302 observed in vitro can be applied to inhibit teratoma growth in vivo, which may serve as a potential treatment for a variety of tumors.

Mir-302 Inhibits the Cell Proliferation Rates of Human Primary Epithelial Skin Culture (hpESC), Human Prostatic Carcinoma (PC3), and Human Melanoma Colo-829 (Colo) Cells We have designed and tested a series of mir-302 constructs with either a linked mir-302a-mir-302b-mir-302c-mir-302d pre-miRNA cluster (SEQ.ID.NOs.9-16) or a manually re-designed pre-mir-302 mimic (e.g. a hairpin-like sequence containing 5'-UAAGUGCUUC CAUGUUU-3' (SEQ.ID.NO.3)) for transfectively silencing the mir-302 target genes in tested hpESC, PC3 and Colo cells. In this study, the mature sequences of mir-302a, mir-302b, mir-302c and mir-302d are 5'-UAAGUGCUUC CAUGUUUUGG UGA-3' (SEQ.ID.NO.71), 5'-UAAGUGCUUC CAUGUUUUAG UAG-3' (SEQ.ID.NO.72), 5'-UAAGUGCUUC CAUGUUU-CAG UGG-3' (SEQ.ID.NO.73), and 5'-UAAGUGCUUC CAUGUUUGAG UGU-3' (SEQ.ID.NO.74), respectively. Notably, these mir-302-like gene-silencing effecter homologues share a highly conserved 5'-end region in their first seventeenth nucleotides (100% homology), identical to 5'-UAAGUGCUUC CAUGUUU-3' (SEQ.ID.NO.3). Also, in these mir-302 homologous sequences, thymine (T) can be used in place of uracil (U).

Figures 12A, 12B, 12C:
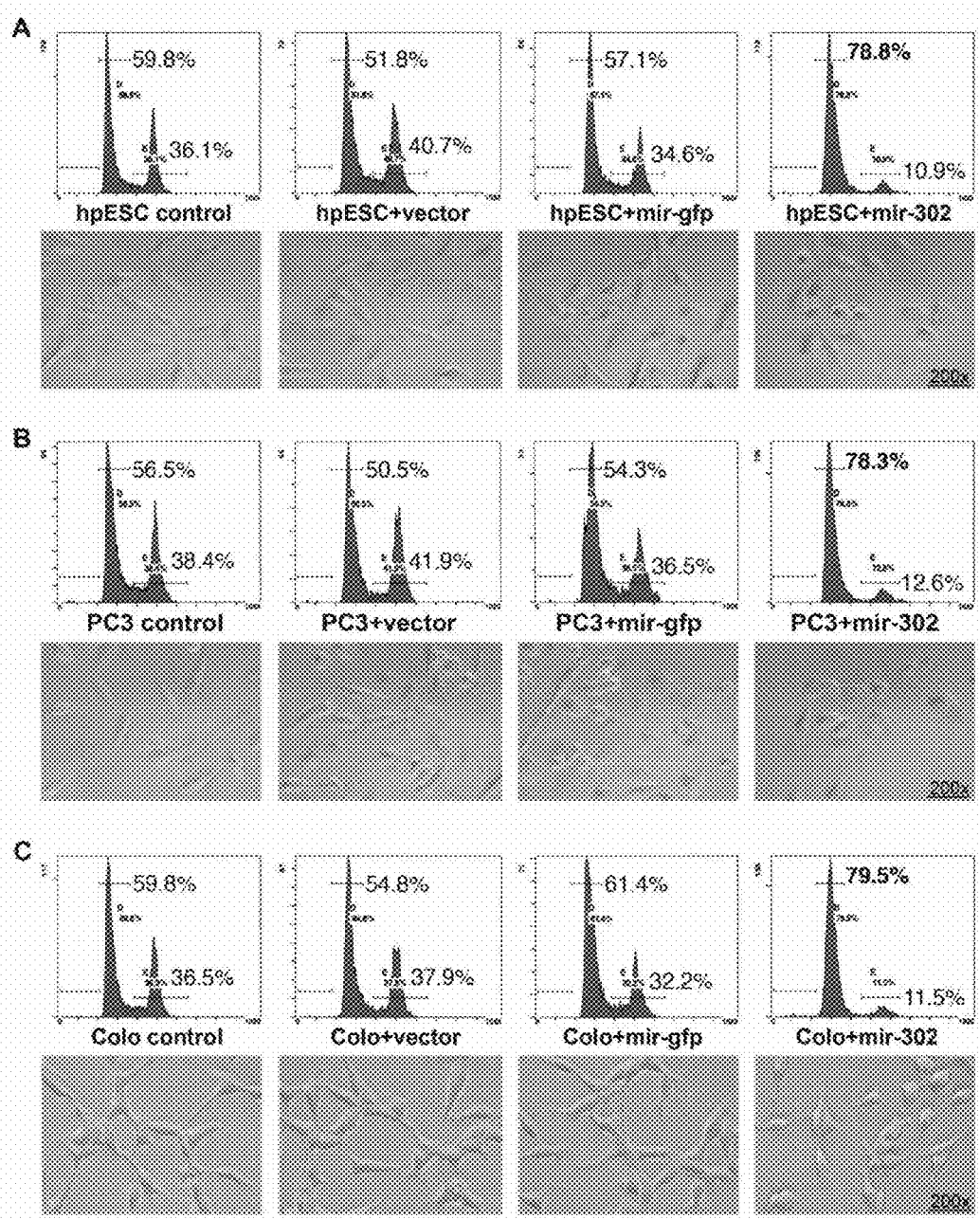
FIGS. 12A-C show the changes of cell morphology and cell proliferation after mir-302-like RNA molecules are transgenically expressed in human primary epithelial skin culture (hpESC), human prostatic carcinoma PC3 (PC3), and human primary melanoma culture Colo (Colo) cells. After the mir-302 transfection, the cells with positive mir-302 expression are named hpESC+mr-302, PC3+mir-302 and Colo+mir-302, respectively.
Figure 13:
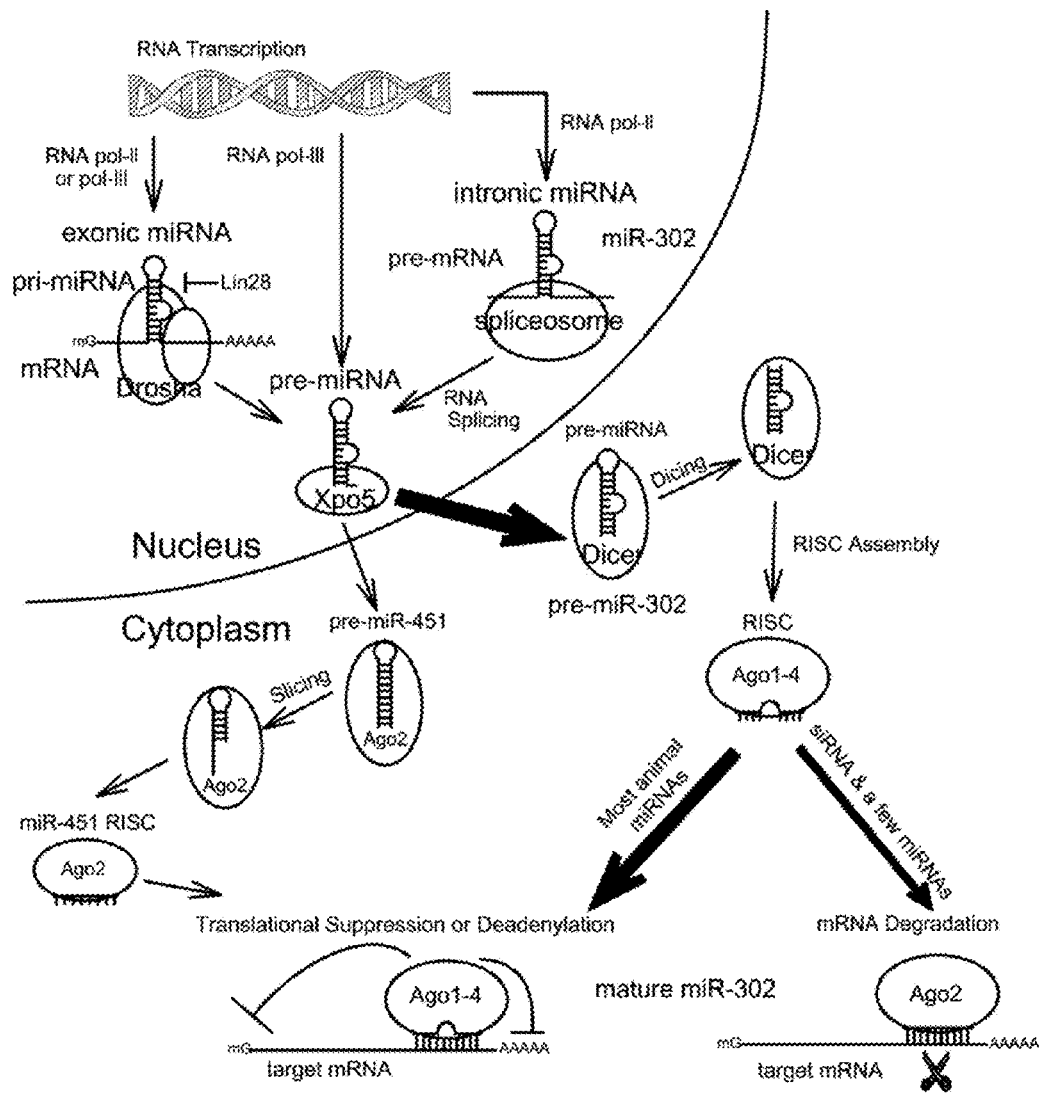
FIG. 13 depicts the natural biogenesis mechanism of the intronic microRNA miR-302. MiR-302 is a natural intronic microRNA (miRNA), encoded in the intronic region of the La ribonucleoprotein domain family member 7 (LARP7 or PIP 78) gene. During miR-302 biogenesis, primary miRNA precursors (pri-miRNA) are first transcribed by type-II RNA polymerases (Pol-II) along with the LARP7 gene transcripts and spliced by cellular spliceosomes to form hairpin-like miRNA precursors (pre-miRNA), which are then exported out of the nucleus by Exportin-5 (Xpo5) and further diced by Dicer-like RNaseIII endoribonucleases in cytoplasm to form mature miRNAs. Consequently, mature miR-302 molecules are assembled into RNA-induced silencing complexes (RISC) with argonaute proteins (Ago1-4) that elicit gene-specific silencing.
Figure 14:
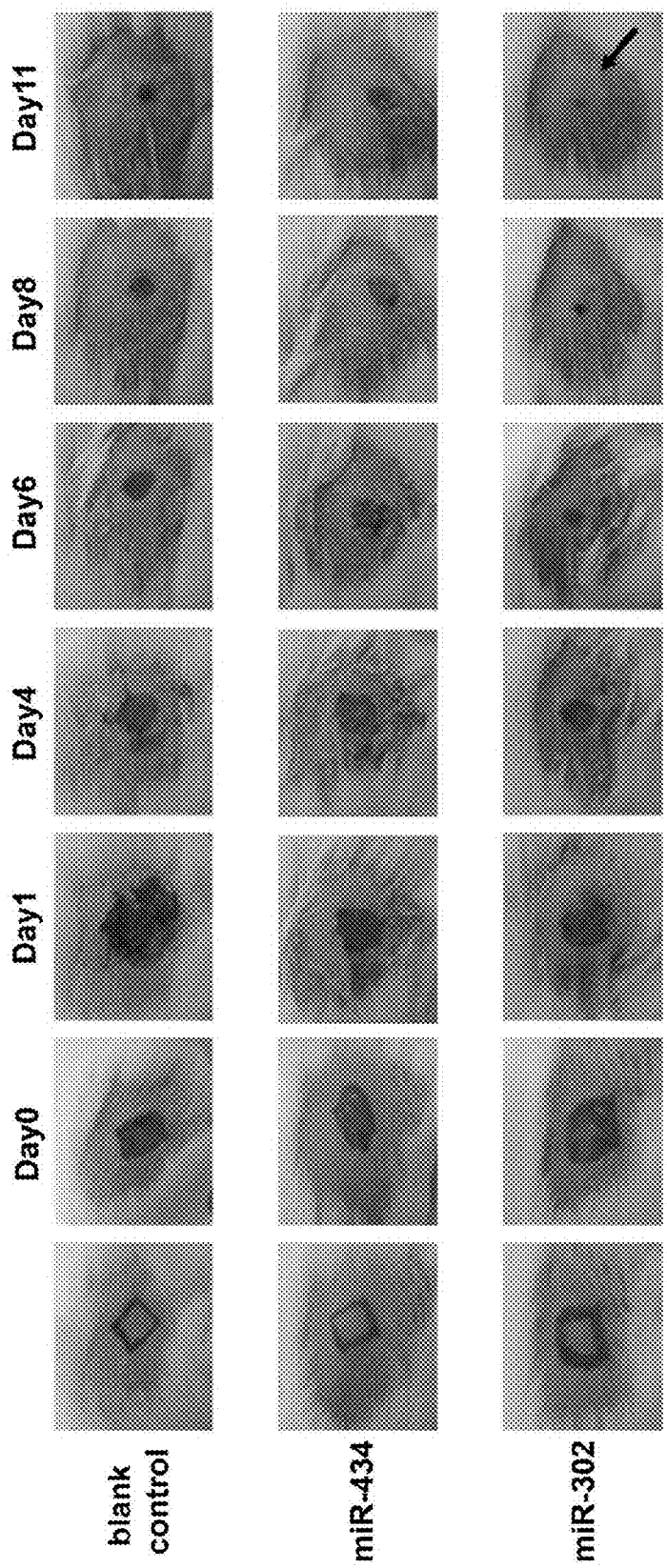
FIG. 14 shows the therapeutic results of an in-vivo pre-investigational new drug (pre-IND) study using pro-mir-302 to treat skin open wounds in mice. Three different treatments were tested: top, blank ointment only; middle, 10 µg/mL of pro-mir-434 in ointment (negative control); and bottom, 10 µg/mL of pro-mir-302 in ointment.

In these experiments, we transfect the mir-302a-mir-302b-mir-302c-mir-302d pre-miRNA cluster into hpESC and PC3 cells, and the re-designed mir-302 homologue (SEQ.ID.NO.75) into Colo cells, respectively. After mir-302 transfection, all these cell lines transform their morphology (lower panels) from spindle or amoeba-like shapes to a more round shape outline, indicating that they may lose ability for cell migration and have a very slow cell replication rate similar to stem cell growth (FIGS. 12A-C). Flow cytometry analyses (upper panels) of their DNA contents (y axis) to different cell cycle stages (x axis) show an over 67% reduction in the mitotic cell population, confirming the slow cell proliferation of these mir-302-transfected cells, while the cell population is indicated by the DNA content measured at each cell cycle stage. The first (left) and second (right) peaks represent the levels of resting G0/G1 and mitotic M phase cell populations in the entire tested cell population, respectively. The mitotic cell population is decreased from 36.1% to 10.9% in hpESC, from 38.4% to 12.6% in PC3, and from 36.5% to 11.5% in Colo cells after mir-302 transfection, whereas there is no significant changes in either cell morphology or cell proliferation after transfection with empty vector or vector containing mir-gfp pre-miRNA insert. The mir-gfp pre-miRNA is designed to target against a firefly EGFP gene, which shares no homology to human and mouse genes. Based on these findings, we show that transgenic expression of mir-302 homologues can transform human primary culture cells and cancerous cells into a more embryonic stem (ES)-like morphology and rate of replication, similar to the changes observed in previously reported iPS cells (Okita et al., (2007) *Nature* 448: 313-317; Wernig et al., (2007) *Nature* 448: 318-324).

Figure 15:
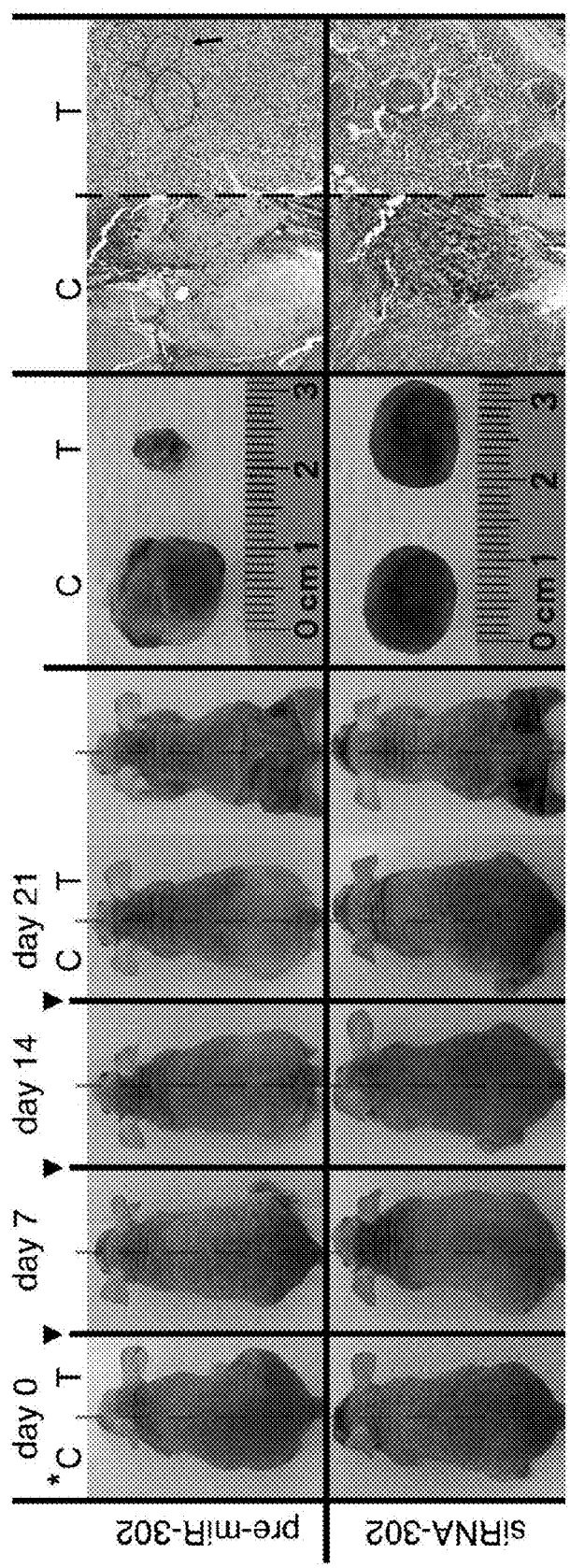
FIG. 15 shows the therapeutic results of an in-vivo pre-investigational new drug (pre-IND) study using pro-mir-302 as an injection drug to treat human liver cancer xenografts in SCID-beige nude mice. Following three treatments (once per week), the pro-lnk-302 drug (pre-miR-302) successfully reduced cancer sizes from 728±328 mm$^3$ (untreated blank control, C) to 75±15 mm$^3$ (pro-mir-302-treated, T), indicating an approximately 90% reduction rate in the average cancer size! No significant therapeutic effect was found in the same protocol with treatments of synthetic siRNA mimics (siRNA-302). Further histological examination (most right) showed that normal liver lobule-like structures (circles pointed by a black arrow) were observed only in pro-mir-302-treated cancer grafts but not other treatments or controls, suggesting that a reprogramming mechanism may occur to rest the malignant cancer cell property back to a relatively normal-like state (Cancer Reversion).

Mir-302 Reprograms High-Grade Human Malignant Liver Cancer Grafts In Vivo to a Low-Grade Benign State The process of cancer progression was thought to be irreversible due to accumulative gene mutations; yet, the present invention discloses a novel microRNA mir-302 precursor (pre-mir-302) function that can reprogram high-grade malignant cancers back to a low-grade benign state, of which the mechanism may be also involved in a rare natural healing process called spontaneous cancer regression. Spontaneous cancer regression occurs very rarely at a rate of approximately 1 in 100,000 cancer patients. The inventors found that treatment of pre-mir-302 is able to increase this rare cancer regression rate to about 90%. As shown in FIG. 15, the therapeutic results of using pre-mir-302 mimics (pro-mir-302) as a drug to treat human liver cancer xenografts in SCID-beige nude mice demonstrated that the pro-mir-302 drug successfully reduced cancer sizes from 728±328 mm$^3$ (untreated blank control, C) to 75±15 mm$^3$ (pro-mir-302-treated, T), indicating an approximately 90% reduction rate in the average cancer size, whereas treatments of other synthetic siRNA mimics (siRNA-302) did not provide any similar therapeutic effect. Further histological examination (most right) showed that normal liver lobule-like structures (circled and pointed by a black arrow) were observed only in pro-mir-302-treated cancer grafts but not other treatments or controls, suggesting that a reprogramming mechanism has occurred to rest the malignant cancer cell property back to a relatively normal-like state (Cancer Reversion). This novel reprogramming mechanism is likely related to the tumor suppressor function of mir-302, which can simultaneously and specifically target multiple human oncogenes for silencing and hence eliminates/prevents the onset of these tumorigenic signal transduction pathways. Nevertheless, this reprogramming mechanism may be also different from the previously reported somatic cell reprogramming function of mir-302 (Lin et al., 2008 and 2011) because no Oct4-positive pluripotent stem cell has been identified yet.

Figure 16:
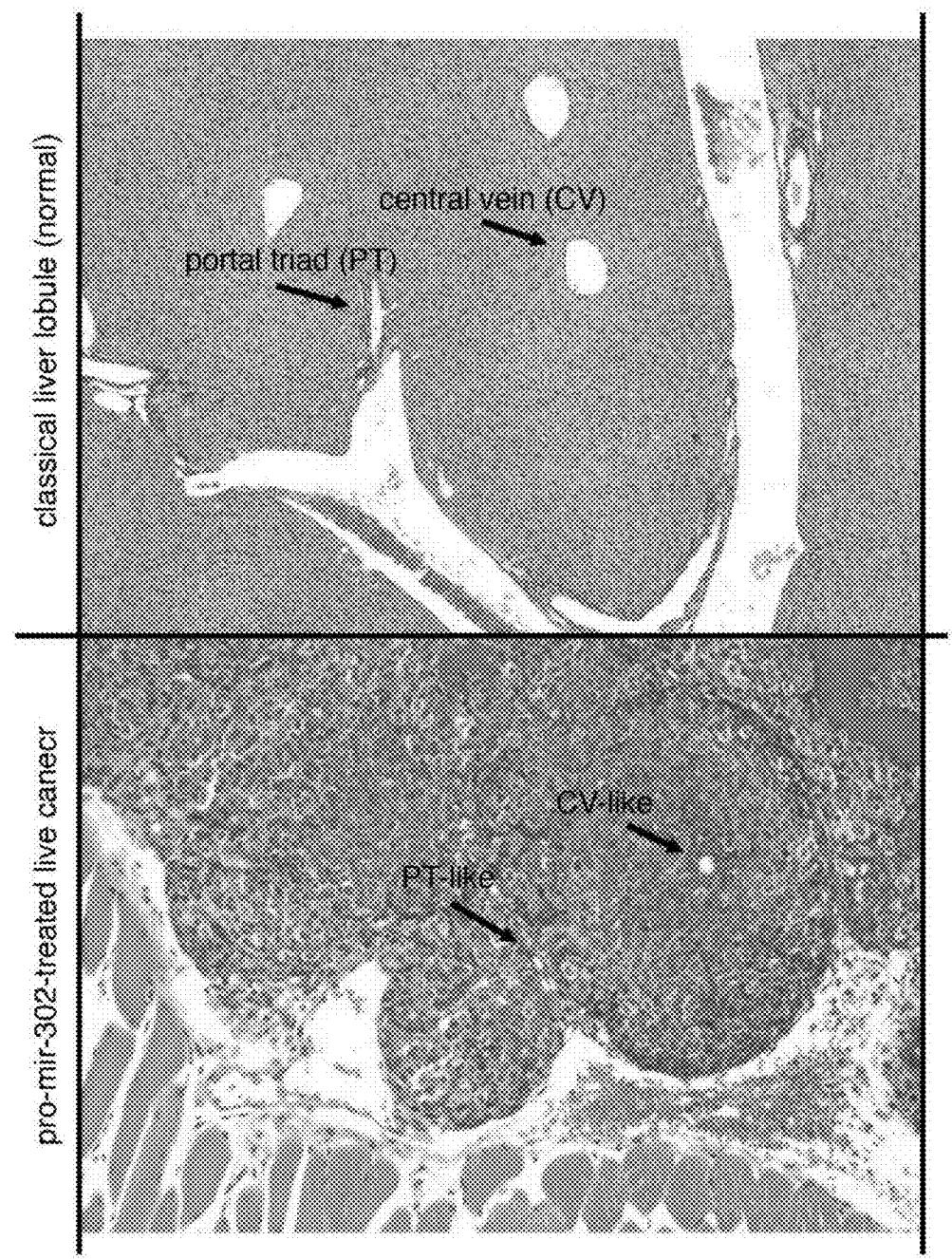
FIG. 16 shows the histological similarity between normal liver tissues and pro-mir-302-treated human liver cancer xenografts in vivo. After three treatments (once per week), the pro-mir-302 drug successfully reprogrammed high-grade (grade IV) human liver cancer grafts to a more benign low-grade (less than grade II) state. Similar to normal liver tissues (top), the treated cancer grafts could form classical liver lobules, containing central vein (CV)-like and portal triad (PT)-like structures (indicated by black arrows). As cancer cells are generally more acidic than normal liver cells, the result of hematoxylin & eosin (H&E) staining shows more purple in cancer cells whereas more red in normal liver cells.
Figure 17:
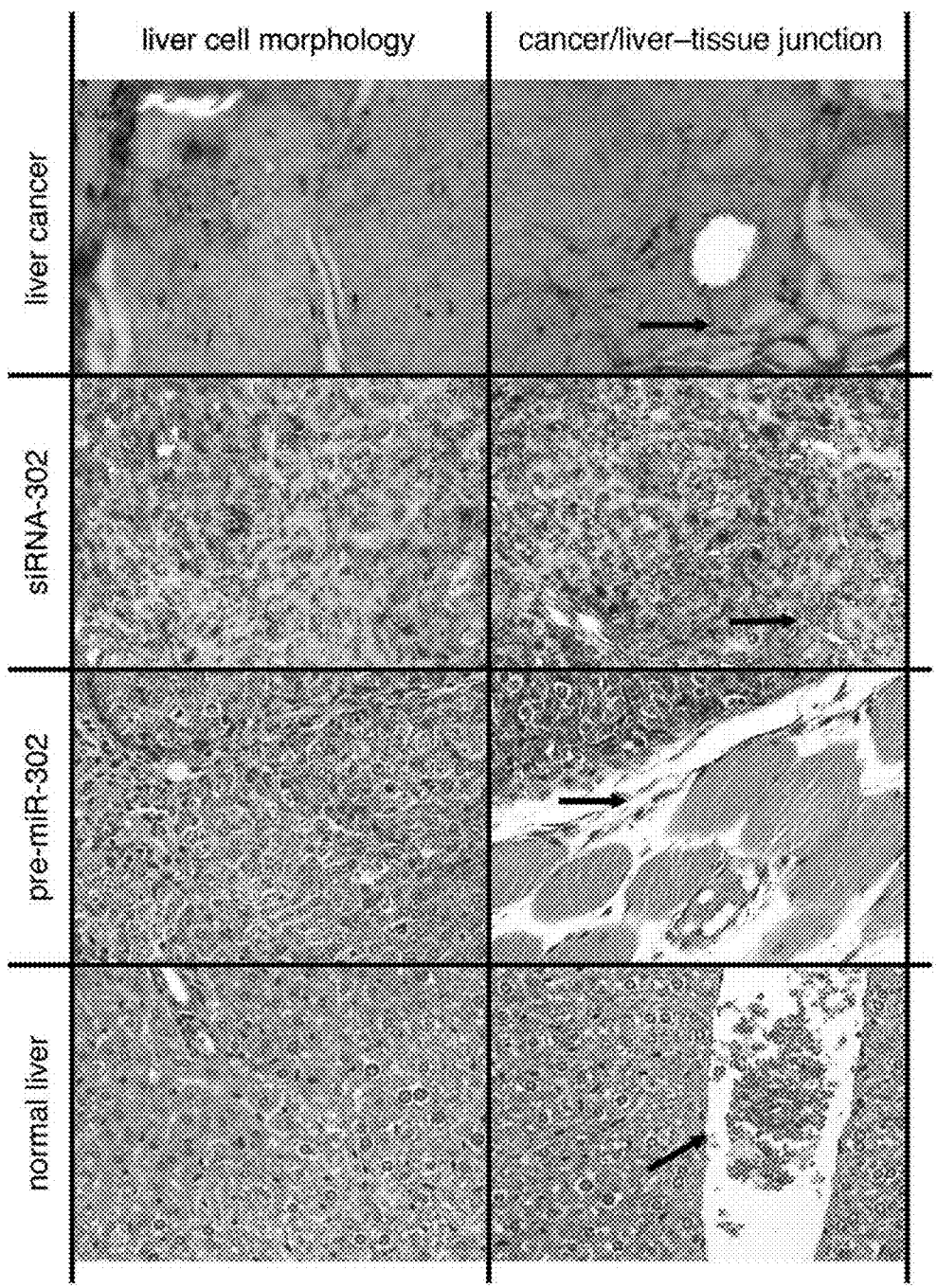
FIG. 17 shows the patho-histological comparison among untreated, siRNA-treated, pro-mir-302-treated human liver cancer grafts and normal liver tissues in SCID-beige nude mice. Without treatment (top), the engrafted human liver cancer aggressively invaded into normal tissues, such as muscles and blood vessels, and formed massive cell-cell and cancer-tissue fusion structures, indicating its high malignancy and metastasis. Treatment of siRNA mimics (siRNA-302) did not significantly reduce the malignancy of the engrafted liver cancer (upper middle), probably due to the short half-life of siRNA molecules in vivo. On the contrary, treatment of pro-mir-302 (=pre-miR-302) not only reprogrammed the engrafted cancer cells to a normal liver cell-like morphology (no fusion) but also successfully inhibited cancer invasion into the surrounding normal tissues (lower middle). Compared to normal liver tissues (bottom), pro-mir-302-treated cancers clearly displayed similar lobule structures, normal gland cell-like arrangements, and very clear boundaries between cell-cell and cancer-tissue junctions (black arrows), indicating that these treated cancers have been downgraded to a very benign state.

More detailed histological examination further revealed that the pro-mir-302 drug successfully reprogrammed high-grade (grade IV) human liver cancer grafts to a more benign low-grade (less than grade II) state. As shown in FIG. 16, the treated cancer grafts could form classical liver lobules containing central vein (CV)-like and portal triad (PT)-like structures (indicated by black arrows), highly similar to normal liver tissue structures (top). Comparison among untreated, siRNA-treated, pro-mir-302-treated human liver cancer grafts and normal liver tissues in SCID-beige nude mice (FIG. 17) showed that the engrafted human liver cancer without treatment (top) aggressively invaded into surrounding normal tissues, such as muscles and blood vessels, and formed massive cell-cell and cancer-tissue fusion structures, demonstrating its high malignancy and metastasis. Treatment of siRNA mimics (siRNA-302) did not significantly reduce the malignancy of the engrafted liver cancer (upper middle), probably due to the short half-life of siRNA molecules in vivo. On the contrary, treatment of pro-mir-302 (pre-miR-302) not only reprogrammed the engrafted cancer cells to a normal liver cell-like morphology (no fusion) but also successfully inhibited any cancer invasion into the surrounding normal tissues (lower middle). Compared to normal liver tissues (bottom), pro-mir-302-treated cancers clearly displayed similar lobule structures, normal gland cell-like arrangements, and very clear boundaries between cell-cell and cancer-tissue junctions (black arrows), suggesting that these treated cancers have been downgraded to a very benign state. Further continuous treatments of pro-mir-302 drug over six times could completely eliminate the cancer xenografts in all six samples.

Figure 9A:
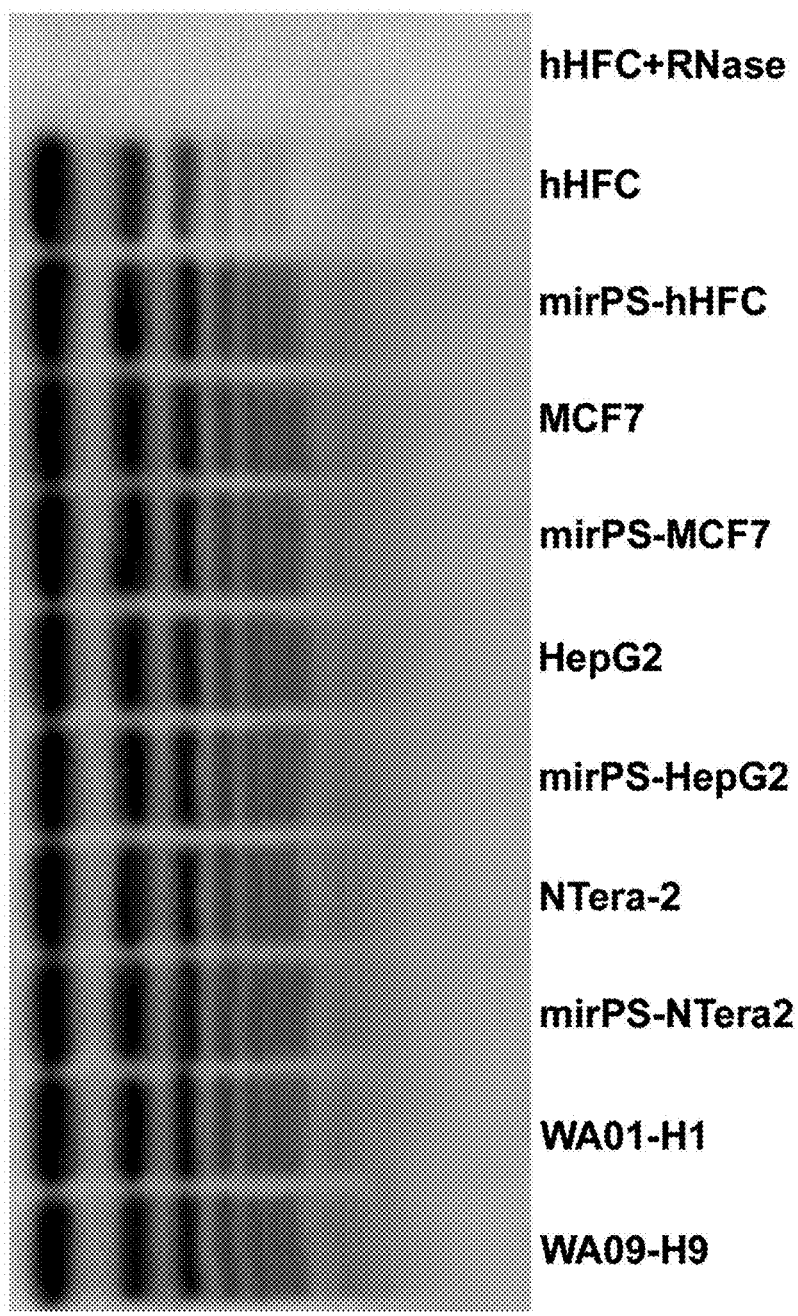
FIGS. 9A-C show analyses of telomerase activity in mirPS-hHFC and various tumor/cancer-derived mirPS cell lines in response to the mir-302 expression induced by 10 μM Dox. (A) Telomerase activities shown by TRAP assays (n=5, $p<0.01$). Telomerase activity was sensitive to RNase treatment (hHFC+RNase). (B) Western blotting confirming the consistent increase of hTERT and decrease of AOF2 and HDAC2 expression in various mirPS cell lines (n=5, $p<0.01$). (C) Telomerase activities measured by telomerase PCR ELISA assays (OD470-OD680; n=3, $p<0.01$).
Figure 9B:
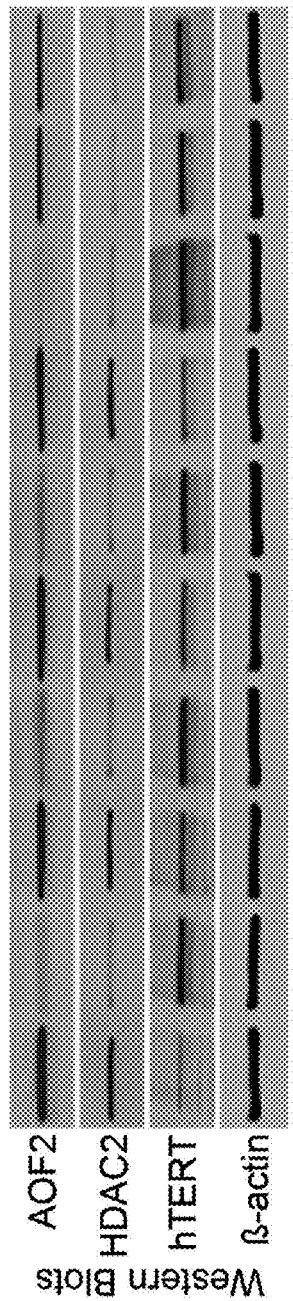
Figure 9C:
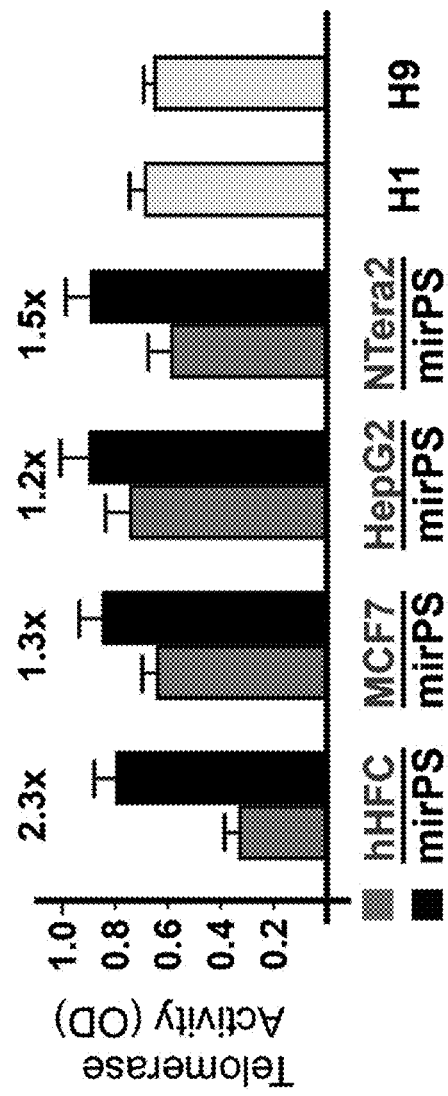
Figure 10A:
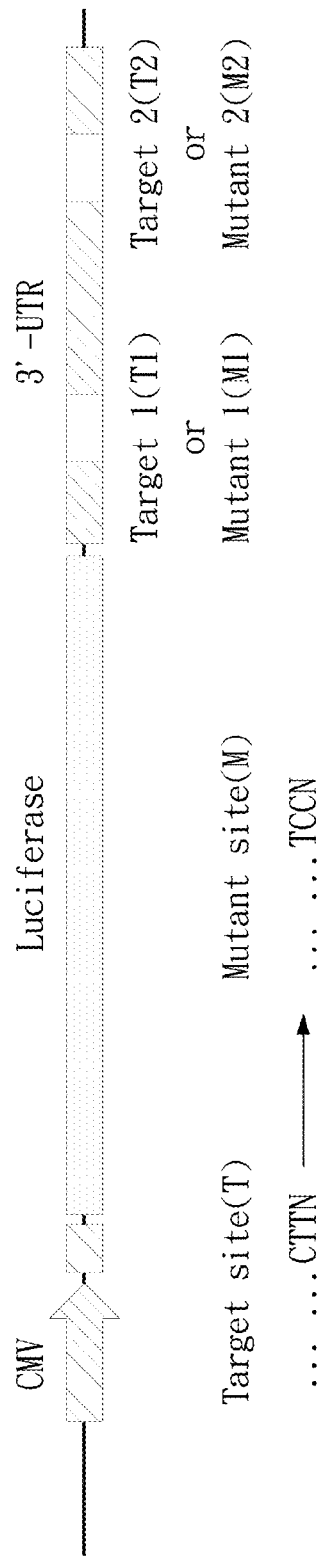
FIGS. 10A-D show analyses of mir-302-induced silencing effects on its targeted epigenetic genes. (A) Constructs of the luciferase 3'-UTR reporter genes, which carry either two normal (T1+T2) or two mutant (M1+M2), or a mixture of both (T1+M2 or M1+T2), mir-302 target sites in the 3'-UTR. The mutant sites contained a mismatched TCC motif in place of the uniform 3'-CTT end of the normal target sites. (B) Effects of Dox-induced mir-302 on the luciferase expression (n=5, p<0.01). (C) and (D) Western blot analyses showing the changes of major mir-302-targeted epigenetic gene expression induced by high (10 µM Dox) and low (5 µM Dox) mir-302 concentrations in mirPS cells compared to those found in hES H1 and H9 cells (n=4, p<0.01).
Figure 10B:
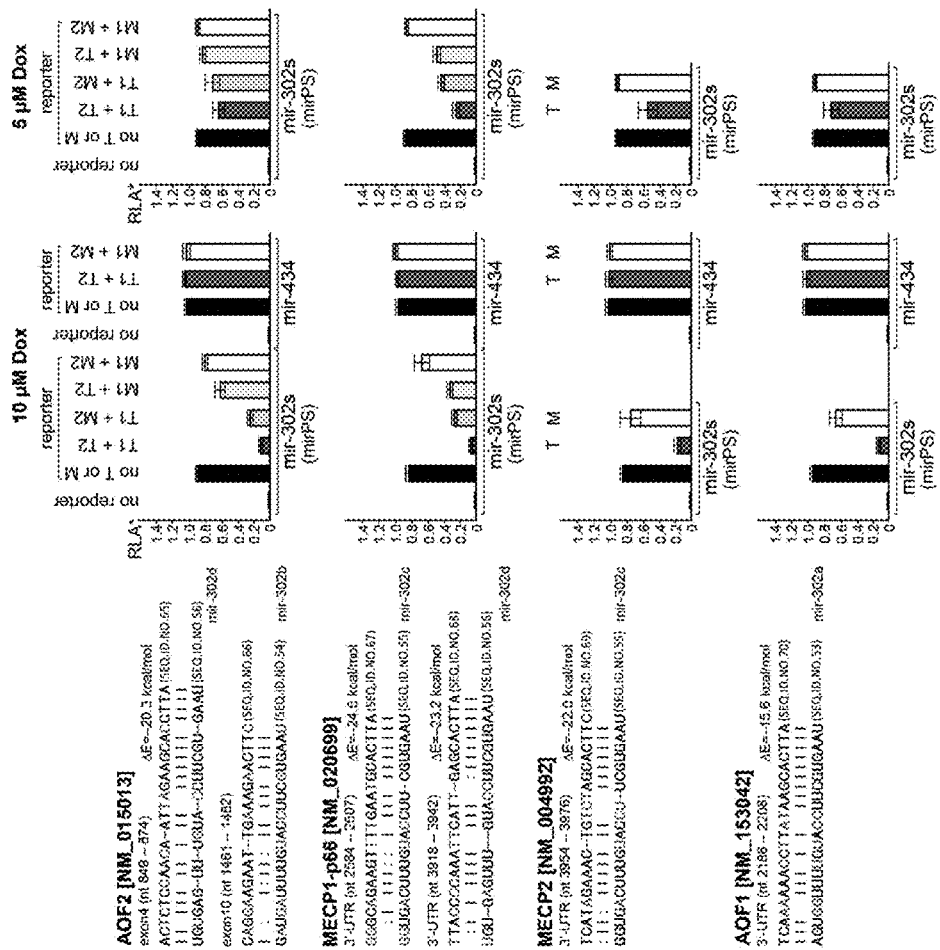
Figures 10C, 10D:
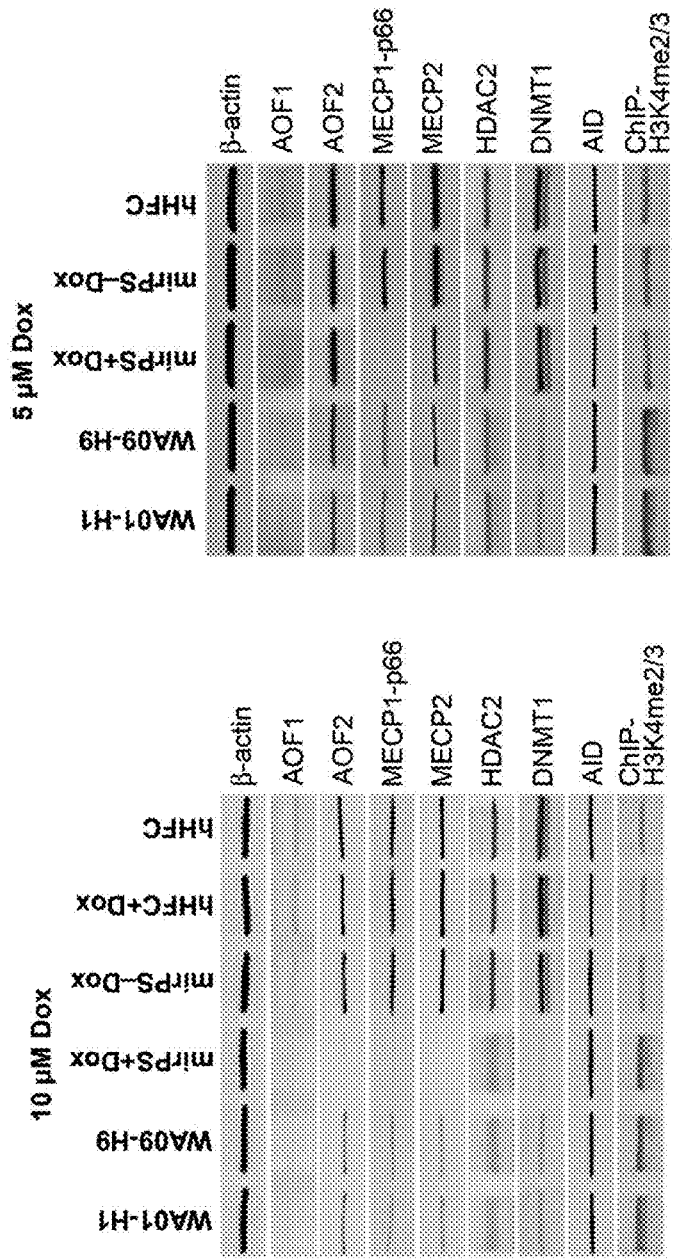

Mir-302 May Cause Cell Senescence through p16Ink4a/p14ARF Activation rather than Telomere Shortening Human iPS cells have been reported to exhibit problems of early senescence and limited expansion (Banito et al., 2009; Feng et al., 2010). Normal adult cells also undergo a limited number of divisions and finally reach a quiescence state called replicative senescence. Cells that escape from replicative senescence often become immortal cells such as tumor/cancer cells; thus, replicative senescence is a normal defense mechanism against tumor/cancer cell formation. In this study, we have found that mir-302 can directly silence BMI-1 to induce p16Ink4a/p14ARF-associated cell cycle regulation. Other studies have further implicated that BMI-1 can also activate human telomerase reverse transcriptase (hTERT) transcription and increase telomerase activity to bypass replicative senescence and increase the cell life span (Dimri et al., 2002). Thus, it is conceivable that mir-302 overexpression may cause hTERT-associated senescence in mirPS cells. To clarify this point, we performed telomeric repeat amplification protocol (TRAP) assay (Example 16) to measure the telomerase activity. Surprisingly, as shown in FIG. 9A, all mirPS cells treated with 10 µM Dox exhibit a strong telomerase activity similar to that of their original tumor/cancer cells and hES H1/H9 cells. Moreover, western blotting also showed that hTERT expression was increased rather than decreased in these mirPS cells (FIG. 9B). The increase of relative telomerase activity was also confirmed by telomerase PCR ELISA assay (FIG. 9C). In addition, we further detected the silencing of lysine-specific histone demethylase AOF2 (also known as KDM1/LSD1) and histone deacetylase HDAC2 in these mirPS cells (FIG. 9B). Previous studies have reported that AOF2 is required for the transcriptional suppression of hTERT and deficiency of both AOF2 and HDAC2 induces hTERT overexpression (Won et al., 2002; Zhu et al., 2008). Our recent study has also found that both AOF2 and HDAC2 are strong targets of mir-302 and are both silenced in the mirPS cells (FIG. 10). Therefore, mir-302 actually increases telomerase activity rather than causes hTERT-associated senescence in mirPS cells. However, the effect of this increased hTERT activity may be counteracted by the mir-302-induced BMI-1 suppression and p16Ink4a/p14ARF activation, resulting in a balance for preventing tumor/cancer cell formation in mirPS cells.

Figure 11:
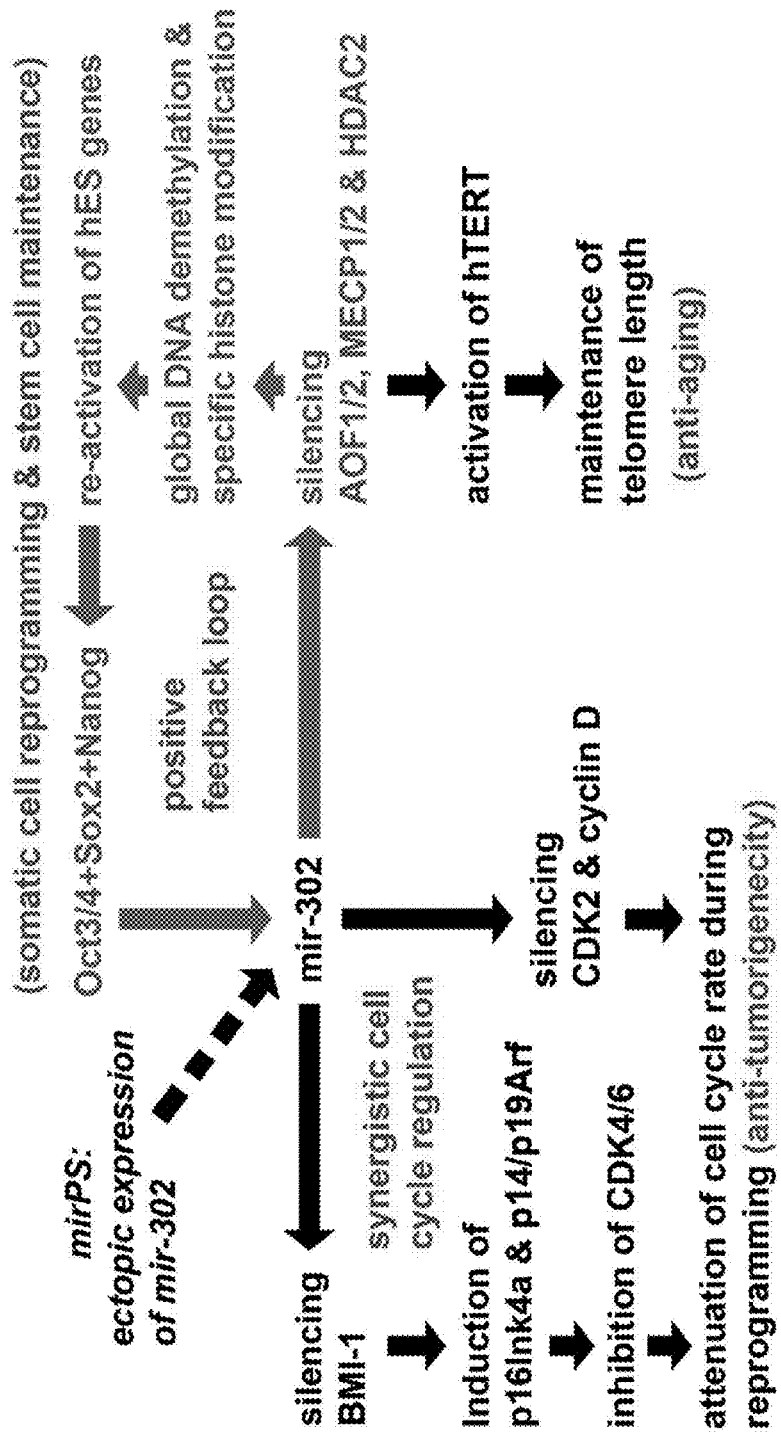
FIG. 11 depicts the proposed mechanism of mir-302-mediated SCR and cell cycle regulation. Based on our previous and current studies, two collateral events were discovered. First, reprogramming is initiated by strong silencing of multiple epigenetic regulators AOF1/2, MECP1/2 and HDAC2, leading to global genomic DNA demethylation, whereby re-activating hES cell marker genes essential for SCR induction (marked in gray). Second, cell cycle attenuation is caused by co-suppression of G1-checkpoint regulators CDK2, cyclins D1/D2 and BMI-1 as well as activation of p16Ink4a and p14/p19Arf to quench all cellular activities ready for SCR (marked in black). Quiescence at this dormant G0/G1 state also prevents the possible random growth and/or tumor-like transformation of the reprogrammed pluripotent stem cells. Collectively, the synergistic effect of these two events results in a more accurate and safe reprogramming process, by which pre-mature cell differentiation and tumorigenecity are both inhibited.

In sum, our present invention utilizes a novel tumor suppressor function of mir-302 for cancer therapy. We found that mir-302-mediated cell cycle regulation involves a highly coordinate mechanism between co-suppression of G1-checkpoint regulators and activation of CDK inhibitors. All these genetic events must occur simultaneously to prevent any loophole for G1-S progression. Quiescence at G0/G1 phase cell cycle is important for SCR initiation. In this dormant state, somatic cell genomes can be largely demethylated and over 91% of the cellular transcriptome are reprogrammed to a hES-like gene expression pattern. Through deciphering the interactions between mir-302 and its target genes, we learned the intricate mechanism for mir-302-associated cell cycle regulation during SCR as shown in FIG. 11. Our previous studies have demonstrated that mir-302 silences its targeted epigenetic regulators to activate Oct3/4-Sox2-Nanog co-expression, and in turn these reprogramming factors function to induce SCR (Lin et al., 2008). In advance, this invention further reveals that mir-302 concurrently silences CDK2, cyclins D1/D2 and BMI-1 to attenuate cell division during SCR. Proper control of the cell cycle rate is of critical biological importance in preventing the tumorigenecity of oncogenes that are often activated during SCR. To this, mir-302 silences CDK2 and cyclins D1/D2 to hinder the G1-S transition at this critical moment. Meanwhile, inhibition of BMI-1 further enhances the tumor suppressor activities of p16Ink4a and p19Arf. Through these synergistic cell cycle regulation pathways, mir-302 is able to initiate SCR while not aggravating cell tumorigenecity.

Advantageously, there are at least five breakthroughs in the present invention. First, one mir-302-like gene effector can replace all four reprogramming transcription factors Oct4-Sox2-Klf4-c-Myc and Oct4-Sox2-Nanog-Lin28 for reprogramming human cells to hES-like stem cells. These reprogrammed cells are useful for stem cell therapy. Second, because of the small size (about 23 ribonucleotides) of a mir-302-like gene silencing effector, the vector expressing such a small sized RNA can be designed to be very compact and highly efficient for in vivo transfection. Third, the RNA-related cytotoxicity is prevented by intracellular NMD system and inducible expression. Fourth, mir-302-induced apoptosis only occurs in tumor/cancer cells rather than normal human cells. Last, the present invention has used polysomal, liposomal and electroporation-based transfection in place of retroviral/lentiviral infection to deliver the mir-302-expressing nucleic acid composition into tumor/cancer cells, confirming the safety and therapeutic use of the mir-302-like gene silencing effectors in vitro and in vivo. Taken together, these advantages have shown the feasibility of using the mir-302-like gene silencing effector and its expression composition for tumor/cancer therapy, providing a completely novel design for the development of universal cancer drugs and/or vaccines.

A. DEFINITIONS

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more deoxyribonucleotides (DNAs) and/or ribonucleotides (RNAs), preferably more than three, and usually more than ten. An oligonucleotide longer than 13 nucleotide monomers is also called polynucleotide. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose nucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification, which may be selected from the group consisting of mRNA, hnRNA, rRNA, tRNA, snoRNA, snRNA, pre-microRNA, viral RNA and their RNA precursors as well as derivatives.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Also in RNA, uracil (U) may form base pairing with guanine (G). Generally the partnership is achieved through hydrogen bonding. For example, a sense nucleotide sequence "5'-A-T-C-G-U-3" can form complete base pairing with its antisense sequence "5'-A-C-G-A-T-3" or "5'-G-C-G-A-T-3".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3'" is complementary to the sequence "5'-A-C-T-3'", and also to "5'-A-C-U-3'". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (snRNA) and small interfering RNA (siRNA). These small RNA molecules usually function as gene silencers, interfering with expression of intracellular genes containing either completely or partially complementarity to the small RNAs.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNA capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA(s), depending on the complementarity between the miRNA and its target mRNA(s). Natural miRNAs are found in almost all eukaryotes, functioning as a defense against viral infections and allowing regulation of gene expression during development of plants and animals. In principle, one miRNA often target multiple target mRNAs to fulfill its full functionality while on the other hand multiple miRNAs may target the same genes to enhance the full effect of gene silencing.

MicroRNA Precursor (Pre-miRNA): hairpin-like single-stranded RNA containing stem-arm and stem-loop regions for interacting with intracellular RNaseIII Dicer endoribonucleases to produce one or multiple mature microRNAs (miRNAs) capable of silencing a targeted gene or a specific group of targeted genes containing full or partial complementarity to the mature microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation required for being assembled into an RNA-induced silencing complex (RISC) with argonaute protein (AGO).

Prokaryote-produced MicroRNA Precursor (Pro-miRNA): small hairpin-like RNA similar to natural microRNA precursor (pre-miRNA) but transcribed from artificially introduced miRNA expression plasmids in prokaryotic competent cells. For example, pro-mir-302 is structurally as same as pre-mir-302 but transcribed from either a pLVX-Grn-miR302+367 or pLenti-EF1alpha-RGFP-miR302 vector in competent *E. coli* strain DH5alpha cells (Example 18). As prokaryotic cells normally do not express the high secondary structures of eukaryotic pre-miRNA, the production of pro-miRNA in prokaryotes usually requires additional chemical stimulation to stabilize the formation of RNA secondary structures (Lin's U.S. Ser. No. 13/572,263).

Small interfering RNA (siRNA): short double-stranded RNA sized about 18-27 perfectly base-paired ribonucleotide duplexes and capable of degrading target gene transcripts with almost perfect complementarity.

Small or short hairpin RNA (shRNA): single-stranded RNA that contains a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

Eukaryotic Promoter: a sequence of nucleic acid motifs which are required for gene transcription and can be recognized by eukaryotic type II RNA polymerases (pol-2), pol-2 equivalent, and/or pol-2 compatible viral polymerases Type-II RNA Polymerase (Pol-II or pol-2) Promoter: a RNA promoter that is recognized and bound by eukaryotic type-II RNA polymerases (Pol-II or pol-2) which transcribe eukaryotic messenger RNAs (mRNAs) and/or microRNAs (miRNAs). For example, but not limited, a pol-2 promoter can be a mammalian RNA promoter or a cytomegaloviral (CMV) promoter.

Type-II RNA Polymerase (Pol-II or pol-2) Equivalent: an eukaryotic transcription machinery selected from the group consisting of mammalian type-II RNA polymerases (Pol-II or pol-2) and Pol-II compatible viral RNA polymerases.

Pol-II Compatible Viral Promoter: a viral RNA promoter capable of using the eukaryotic poi-2 or equivalent transcription machinery for its gene expression. For example, but not limited, a pol-2 compatible viral promoter can be a cytomegaloviral (CMV) promoter or a retroviral long terminal repeat (LTR) promoter.

Cistron: a sequence of nucleotides in a DNA molecule coding for an amino acid residue sequence and including upstream and downstream DNA expression control elements.

Intron Excision: a cellular mechanism responsible for RNA processing, maturation and degradation, including RNA splicing, exosome digestion, nonsense-mediated decay (NMD) processing, and a combination thereof.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Donor Splice Site: a nucleic acid sequence either containing or homologous to the SEQ.ID.NO.4 sequence or 5'-GTAAG-3' (SEQ.ID.NO.47).

Acceptor Splice Site: a nucleic acid sequence either containing or homologous to the SEQ.ID.NO.5 sequence or 5'-CTGCAG-3' (SEQ.ID.NO.48).

Branch Point: an adenosine (A) nucleotide located within a nucleic acid sequence containing or homologous to the SEQ.ID.NO.6 sequence or 5'-TACTAAC-3' (SEQ.ID.NO.44).

Poly-Pyrimidine Tract: a high T or C content nucleic acid sequence containing or homologous to the SEQ.ID.NO.7 or SEQ.ID.NO.8 sequence.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate, cancer, breast cancer, liver cancer, lung cancer, brain tumor/cancer, lymphoma, leukemia and a combination thereof.

Expression-Competent Vector: a linear or circular form of single- or double-stranded DNA selected form the group consisting of plasmid, viral vector, transposon, retrotransposon, DNA transgene, jumping gene, and a combination thereof.

Antibiotic Resistance Gene: a gene capable of degrading antibiotics selected from the group consisted of penicillin G, streptomycin, ampicillin (Amp), neomycin, G418, kanamycin, erythromycin, paromycin, phophomycin, spectromycin, tetracycline (Tet), doxycycline (Dox), rifapicin, amphotericin B, gentamycin, chloramphenicol, cephalothin, tylosin, and a combination thereof.

Restriction/Cloning Site: a DNA motif for restriction enzyme cleavage including but not limited AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/UI/XI, ClaI, Csp6I, DpnI, DraI/II, EagI, Ecl136II, EcoRI/RII/47III/RV, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI, XmaI cleavage site.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Cell Cycle Regulator: a cellular gene involved in controlling cell division and proliferation rates, consisting but not limited of CDK2, CDK4, CDK6, cyclins, BMI-1, p14/p19Arf, p15Ink4b, p16Ink4a, p18Ink4c, p21Cip1/Waf1, and p27Kip1, and a combination thereof.

Tumor Suppression Effect: a cellular anti-tumor and/or anti-cancer mechanism and response consisting of, but not limited, cell cycle attenuation, cell cycle arrest, inhibition of tumor cell growth, inhibition of cell tumorigenecity, inhibition of tumor/cancer cell transformation, induction of tumor/ cancer cell apoptosis, induction of normal cell recovery, reprogramming high-grade malignant cancer cells to a more benign low-grade state (tumor regression), and a combination thereof.

Cancer Therapy Effect: a cell response and/or cellular mechanism resulted from a drug treatment, including, but not limited, inhibition of oncogene expression, inhibition of cancer cell proliferation, inhibition of cancer cell invasion and/or migration, inhibition of cancer metastasis, induction of cancer cell death, prevention of tumor/cancer formation, prevention of cancer relapse, suppression of cancer progression, repairing damaged tissue cells, reprogramming high-grade malignant cancers to a more benign low-grade state (cancer regression/remission), and a combination thereof.

Gene Silencing Effect: a cell response after a gene function is suppressed, consisting of, but not limited, inhibition of oncogene expression, inhibition of cell proliferation, cell cycle arrest, G0/G1-checkpoint arrest, cell cycle attenuation, tumor suppression, anti-tumorigenecity, cancer regression, cancer prevention, cancer cell apoptosis, cell repairing/rejuvenation, cell reprogramming, reprogramming diseased cells to a relatively normal state (spontaneous healing), and a combination thereof.

Transcription Inducer: a chemical agent that can induce and/or enhance eukaryotic gene transcription from a pol-2 or pol-2-like promoter in prokaryotic cells. For example, a transcription inducer contains, but not limited, a chemical structure similar to 3-(N-Morpholino)propanesulfonic acid (MOPS), ethanol, glycerin, or a mixture thereof.

Antibody: a peptide or protein molecule having a pre-selected conserved domain structure coding for a receptor capable of binding a pre-selected ligand.

Pharmaceutical and/or Therapeutic Application: a biomedical utilization, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, drug production, and a combination thereof.

B. COMPOSITIONS AND METHODS

A composition and method for inducing an universal tumor suppression and/or cancer therapy effect using a nucleic acid composition capable of being delivered and processed into mir-302-like gene silencing effectors in a human cell substrate and thus inhibiting mir-302-targeted cell cycle regulators and/or oncogenes to suppress and/or prevent tumor/cancer cell growth, wherein said mir-302-like gene silencing effectors contain a sequence of SEQ.ID.NO.3 and said human cell substrate may be normal or contain at least a tumor and/or cancer cell.

Preferably, the present invention has adopted a novel design and strategy for delivering either inducible or constitutive amount of mir-302-like gene silencing effectors into the treated cells. These mir-302-like gene silencing effectors include mir-302a, mir-302b, mir-302c, mir-302d, and their hairpin-like microRNA precursors (pre-miRNAs) as well as manually re-designed small hairpin RNA (shRNA), pro-miRNA and/or small interfering RNA (siRNA) mimics and their homologues/derivatives, and a combination thereof. The transfection of these mir-302-like gene silencing effectors can be achieved by a vector- or non-vector-based gene delivery method selected from the group consisting of polysomal transfection, liposomal transfection, chemical transfection, electroporation, viral infection, DNA recombination, transposon insertion, jumping gene insertion, microinjection, gene-gun penetration, and a combination thereof. In a vector-based delivery method, the expression of the mir-302-like gene silencing effectors can be driven either by a constitutive (i.e. CMV) or drug-inducible (i.e. TRE-CMV) promoter. Preferably, the drug-inducible recombinant nucleic acid composition is a Tet-On vector containing a recombinant transgene inserted with either a recombinant mir-302 family cluster (mir-302s; hybrid of SEQ.ID.NOs.9-16) or a manually re-designed mir-302 shRNA homologue (i.e. hybrid of SEQ.ID.NOs.17 and 18). The cell substrate may express the mir-302 target genes either in vitro, ex vivo or in vivo. By silencing the mir-302-targeted cell cycle regulators and oncogenes, the present invention is able to suppress cell tumorigenecity and reprogram the treated cells into non-tumor/cancer cells.

EXAMPLES

The following examples serve to illustrate certain preferred embodiments and aspects of the present invention and are not to be construed as limiting the scope thereof.

In the experimental disclosure which follows, the following abbreviations apply: M (molar); mM (millimolar); μm (micromolar); mol (moles); pmol (picomolar); gm (grams); mg (milligrams) μg (micrograms); ng (nanograms); L (liters); ml (milliliters); μl (microliters); ° C. (degrees Centigrade); cDNA (copy or complementary DNA); DNA (deoxyribonucleic acid); ssDNA (single stranded DNA); dsDNA (double-stranded DNA); dNTP (deoxyribonucleotide triphosphate); RNA (ribonucleic acid); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); ATCC (American Type Culture Collection, Rockville, Md.); hES (human embryonic stem cells); iPS (induced pluripotent stem cells); and SCR (somatic cell reprogramming).

Example 1

Cell Culture and Transfection

Human cancer NTera-2, HepG2, MCF7, PC3 and Colo829 cell lines were acquired from ATCC, while human hair follicle cells (hHFCs) were isolated and dissociated from a minimum of two hair dermal papillae by 4 mg/ml collagenase I digestion for 45 min in fresh RPMI 1640 medium supplemented with 20% FBS. For culturing melanocytes, the isolated cells were cultivated in Medium 254 with the addition of human melanocytes growth supplement-2 (HMGS-2, Invitrogen, Carlsbad, Calif.) in the absence of antibiotics at 37° C. under 5% $CO_2$. Cultures were passaged at 70%-80% confluency by exposing cells to trypsin/EDTA solution for 1 min and rinsing once with phenol red-free DMEM medium (Invitrogen), and the detached cells were replated at 1:10 dilution in fresh Medium 254 with HMGS-2 supplements. For electroporation, a mixture of pTet-On-tTS-mir302s (10 μg) and pTet-On-Adv-Neo(−) (50 μg) was added with the isolated cells (20,000-50,000) in a hypoosmolar buffer (200 μl; Eppendorf, Westbury, N.Y.) and electroporation was performed using Eppendorf Multiporator at 300-400 volts for 150 μsec. The electroporated cells were first grown in phenol red-free DMEM medium (Invitrogen) supplemented with 20% knockout serum, 1% MEM nonessential amino acids, 10 ng/ml bFGF, 1 mM GlutaMax, and 1 mM sodium pyruvate, for 24 hours at 37° C. under 5% $CO_2$. Then, 850 μg/ml G418 and >3.75 μg/ml doxycycline (Dox) were added and refreshed daily for 3-5 days till the cells expressed strong red fluorescent RGFP. Next, the individual red fluorescent cell (mirPS) was monitored under a TE2000 inverted microscopic system (Nikon, Melville, N.Y.) and separately collected into a 96-well, using MO-188NE 3D micromanipulators (Nikon). In the absence of Dox, the mirPS cells were grown and passaged in knockout DMEM/F-12 medium (Invitrogen) supplemented with 20% knockout serum, 1% MEM nonessential amino acids, 100 µM β-mercaptoethanol, 1 mM GlutaMax, 1 mM sodium pyruvate, 10 ng/ml bFGF, 100 IU/ml penicillin/ 100 µg/ml streptomycin/250 µg/ml G418, 0.1 µM A83-01, and 0.1 µM valproic acid (Stemgent, San Diego, Calif.), at 37° C. under 5% $CO_2$. Alternatively, in the presence of Dox (3.75-5 µg/ml; Sigma-Aldrich, St. Louis, Mo.), the mirPS cells were cultivated and passaged in the same feeder-free cultural condition with addition of 0.05 µM GSK inhibitor SB216763 (Stemgent). Addition of GSK inhibitor could facilitate mirPS cell proliferation but with a slight tendency to cause neural differentiation. For neural cell induction, the mirPS cells were grown in the above feeder-free cultural condition with 0.05 µM SB216763 but no Dox.

Example 2

Construction of Recombinant Vectors Expressing Mir-302s

The mir-302 familial cluster (mir-302s) was generated as reported (Lin et al., 2008). The mir-302s cluster consists of four parts, including precursor miRNAs (pre-miRNAs) of mir-302a, b, c, and d. Synthetic oligonucleotides (Sigma-Genosys, St. Louis, Mo.) used for constructing the mir-302s cluster were listed below. For expression, we mixed an equal amount (1:1) of the mir-302s cluster and a pre-made SpRNAi-RGFP recombinant gene (Lin et al., 2006 and 2008), and then digested the mixture with MluI/PvuI restriction enzymes at 37° C. for 4 hours. The digested mixture was collected with a gel extraction filter (Qiagen, CA) in 30 µl of dd$H_2O$ and ligated together using T4 DNA ligase at 8° C. for 16 hours. This formed a recombinant mir-302-expressing SpRNAi-RGFP gene, which was further cleaved with XhoI/HindIII restriction enzymes and inserted into a Dox-inducible pSingle-tTS-shRNA vector (Clontech, Palo Alto, Calif.). This formed an inducible pTet-On-tTS-mir302s expression vector. Then, we further modified the pTet-On-tTS-mir302s vector by replacing its U6 promoter with a TRE-CMV promoter isolated from a pTRE-Tight plasmid (Clontech). For generating a non-inducible, constitutive pCMV-miR302s expression vector, we cleaved the modified pTet-On-tTS-mir302s vector with EcoR1 restriction enzyme, removed the upstream tTS-TRE sequence (1.5 kb) by gel electrophoresis, and recovered the cleaved vector from the gel for further DNA ligation to complete the formation of the non-inducible pCMV-miR302s vector.

Synthetic oligonucleotides for DNA recombination of the mir-302 familial pre-miRNA cluster were listed as follows: mir-302a-sense, 5'-GTCACGCGTT CCCACCACTT AAACGTGGAT GTACTTGCTT TGAAACTAAA GAAGTAAGTG CTTCCATGTT TTGGTGATGG ATAGATCTCT C-3' (SEQ.ID.NO.9); mir-302a-antisense, 5'-GAGAGATCTA TCCATCACCA AAACATGGAA GCACTTACTT CTTTAGTTTC AAAGCAAGTA CATCCACGTT TAAGTGGTGG GAACGCGTGA C-3' (SEQ.ID.NO.10); mir-302b-sense, 5'-ATAGATCTCT CGCTCCCTTC AACTTTAACA TGGAAGTGCT TTCTGTGACT TTGAAAGTAA GTGCTTCCAT GTTTTAGTAG GAGTCGCTCA TATGA-3' (SEQ.ID.NO.11); mir-302b-antisense, 5'-TCATATGAGC GACTCCTACT AAAACATGGA AGCACTTACT TTCAAAGTCA CAGAAAGCAC TTCCATGTTA AAGTTGAAGG GAGCGAGAGA TCTAT-3' (SEQ.ID.NO.12); mir-302c-sense, 5'-CCATATGGCT ACCTTTGCTT TAACATGGAG GTACCTGCTG TGTGAAACAG AAGTAAGTGC TTCCATGTTT CAGTGGAGGC GTCTAGACAT-3' (SEQ.ID.NO.13); mir-302c-antisense, 5'-ATGTCTAGAC GCCTCCACTG AAACATGGAA GCACTTACTT CTGTTTCACA CAGCAGGTAC CTCCATGTTA AAGCAAAGGT AGCCATATGG-3' (SEQ.ID.NO.14); mir-302d-sense, 5'-CGTCTAGACA TAACACTCAA ACATGGAAGC ACTTAGCTAA GCCAGGCTAA GTGCTTCCAT GTTTGAGTGT TCGCGATCGC AT-3' (SEQ.ID.NO.15); and mir-302d-antisense, 5'-ATGCGATCGC GAACACTCAA ACATGGAAGC ACTTAGCCTG GCTTAGCTAA GTGCTTCCAT GTTTGAGTGT TATGTCTAGA CG-3' (SEQ.ID.NO.16). Alternatively, we used a manually re-designed shRNA formed by the hybrid of synthetic miR-302s-sense, 5'-GCAGATCTCG AGGTACCGAC GCGTCCTCTT TACTTTAACA TGGAAATTAA GTGCTTCCAT GTTTGAGTGG TGTGGCGCGA TCGATATCTC TAGAGGATCC ACATC-3' (SEQ.ID.NO.17) and mir-302s-antisense, 5'-GATGTGGATC CTCTAGAGAT ATCGATCGCG CCACACCACT CAAACATGGA AGCACTTAAT TTCCATGTTA AAGTAAAGAG GACGCGTCGG TACCTCGAGA TCTGC-3' (SEQ.ID.NO.18), in place of the mir-302 pre-miRNA cluster for easy intronic insertion. In design of mir-302 homologues, thymine (T) can be used in place of uracil (U) or vice versa. All these synthetic sequences were purified with PAGE gel extraction before ligation.

The recombinant mir-302 familial pre-miRNA cluster (mir-302s) was formed by linkage of four mir-302a-d hybrids, including mir-302a-sense and mir-302a-antisense, mir-302b-sense and mir-302b-antisense, mir-302c-sense and mir-302c-antisense, and mir-302d-sense and mir-302d-antisense. The hybrids of mir-302a, mir-302b, mir-302c, and mir-302d were digested by PvuI/XhoI, XhoI/NheI, NheI/XbaI, and XbaI/MluI restriction enzymes, respectively, and collected together by a gel extraction filter column in 35 µl autoclaved dd$H_2O$ (Qiagen, CA). Immediately after that, the mixed hybrids were ligated to form a cluster with T4 DNA ligase (Roche, 20U) and further inserted into the PvuI/MluI-linearized SpRNAi-RGFP recombinant gene. Alternatively, the mir-302 shRNA made by hybridizing SEQ.ID.NO.17 and SEQ.ID.NO.18 was cleaved with PvuI/MluI restriction enzymes and inserted into the PvuI/MluI-linearized SpRNAi-RGFP.

The pTet-On-tTS-mir302s and CMV-mir302s vectors were propagated in *E. coli* DH5α LB culture containing 100 µg/ml ampicillin (Sigma Chemical, St. Louis, Mo.). The propagated pTet-On-tTS-mir302s and CMV-mir302s vectors were isolated and purified using an Endo-Free Maxi-Prep Plasmid Extraction Kit (Qiagen, CA).

Example 3

MicroRNA (miRNA) Microarray Analysis

At 70% confluency, small RNAs from each cell culture were isolated, using the mirVana™ miRNA isolation kit (Ambion). The purity and quantity of the isolated small RNAs were assessed, using 1% formaldehyde-agarose gel electrophoresis and spectrophotometer measurement (Bio-Rad), and then immediately frozen in dry ice and submitted to LC Sciences (San Diego, Calif.) for miRNA microarray analysis. Each microarray chip was hybridized a single sample labeled with either Cy3 or Cy5 or a pair of samples labeled with Cy3 and Cy5, respectively. Background subtraction and normalization were performed. For a dual sample assay, a p-value calculation was performed and a list of differentially expressed transcripts more than 3-fold was produced. The result was shown in FIG. 1C.

Example 4

Northern Blot Analysis

Total RNAs (10 µg) were isolated with a mirVana™ miRNA Isolation Kit (Ambion, Austin, Tex.), fractionated by either 15% TBE-urea polyacrylamide gel or 3.5% low melting point agarose gel electrophoresis, and electroblotted onto a nylon membrane. Detection of mir-302 was performed with a [LNA]-DNA probe (5'-[TCACTGAAAC] ATGGAAGCAC TTA-3') (SEQ.ID.NO.19), while probes for other gene detection were synthesized and listed in Table 1. All probes were purified by high-performance liquid chromatography (HPLC) and tail-labeled with terminal transferase (20 units) for 20 min in the presence of [$^{32}$P]-dATP (>3000 Ci/mM, Amersham International, Arlington Heights, Ill.). Hybridization was carried out in the mixture of 50% freshly deionized formamide (pH 7.0), 5×Denhardt's solution, 0.5% SDS, 4×SSPE and 250 mg/mL denatured salmon sperm DNA fragments (18 hr, 42° C.). Membranes were sequentially washed twice in 2×SSC, 0.1% SDS (15 min, 25° C.), and once in 0.2×SSC, 0.1% SDS (45 min, 37° C.) before autoradiography. The results were shown in FIGS. 1D, 4A and 8B.

Example 5

Western Blot Analysis

Cells ($10^6$) were lysed with a CelLytic-M lysis/extraction reagent (Sigma) supplemented with protease inhibitors, Leupeptin, TLCK, TAME and PMSF, following the manufacturer's suggestion. Lysates were centrifuged at 12,000 rpm for 20 min at 4° C. and the supernatant was recovered. Protein concentrations were measured using an improved SOFTmax protein assay package on an E-max microplate reader (Molecular Devices, CA). Each 30 µg of cell lysate was added to SDS-PAGE sample buffer under reducing (+50 mM DTT) and non-reducing (no DTT) conditions, and boiled for 3 min before loading onto a 6 to 8% polyacylamide gel. Proteins were resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hours at room temperature. Then, a primary antibody was applied to the reagent and incubated the mixture at 4° C. Primary antibodies included Oct3/4 (Santa Cruz Biotechnology, Santa Cruz, Calif.), Sox2 (Santa Cruz), Nanog (Santa Cruz), Lin28 (Abcam Inc., Cambridge, Mass.), UTF1 (Abeam), Klf4 (Santa Cruz), TRP1 (Santa Cruz), keratin 16 (Abeam), CDK2 (Santa Cruz), cyclin D1 (Santa Cruz), cyclin D2 (Abeam), BMI-1 (Santa Cruz), AOF2 (Sigma), HDAC2 (Abcam), hTERT (Santa Cruz), β-actin (Chemicon, Temecula, Calif.), and RGFP (Clontech). After overnight, the membrane was rinsed three times with TBS-T and then exposed to goat anti-mouse IgG conjugated secondary antibody to Alexa Fluor 680 reactive dye (1:2,000; Invitrogen-Molecular Probes), for 1 hour at the room temperature. After three additional TBS-T rinses, fluorescent scanning of the immunoblot and image analysis were conducted using Li-Cor Odyssey Infrared Imager and Odyssey Software v.10 (Li-Cor). The results were shown in FIGS. 1D, 4B, 7C, 7D, 8B and 9B.

Example 6

Apoptotic DNA Laddering Assay

Genomic DNAs were isolated from about two million cells using an Apoptotic DNA Ladder Kit (Roche Biochemicals, Indianapolis, Iowa) and 2 µg of the isolated DNAs were further assessed by 2% agarose gel electrophoresis, according to the manufacturers' suggestion. The result was shown in FIG. 1F.

Example 7

DNA-Density Flow Cytometry

Cells were trypsinized, pelleted and fixed by re-suspension in 1 ml of pre-chilled 70% methanol in PBS for 1 hour at −20° C. The cells were pelleted and washed once with 1 ml of PBS. The cells were pelleted again and resuspended in 1 ml of 1 mg/ml propidium iodide, 0.5 µg/ml RNase in PBS for 30 min at 37° C. Approximately 15,000 cells were then analyzed on a BD FACSCalibur (San Jose, Calif.). Cell doublets were excluded by plotting pulse width versus pulse area and gating on the single cells. The collected data were analyzed using the software package Flowjo using the "Watson Pragmatic" algorithm. The result was shown in FIGS. 3A-3B, 6A-6C.

Example 8

Genome-Wide Microarray Analysis

Human genome GeneChip U133 plus 2.0 arrays (Affymetrix, Santa Clara, Calif.) were used to detect the alterations of over 47,000 human gene expression patterns in tested cells. Total RNAs from each tested sample were isolated using a mirVana™ miRNA Isolation Kit (Ambion), following the manufacturer's suggestion. The purity and quantity of isolated RNAs were assessed using 1% formaldehyde-agarose gel electrophoresis and spectrophotometer measurement (Bio-Rad). The sample signals were normalized using the total average difference between perfectly matched probes and mismatched probes. Alterations of genome-wide gene expression patterns were analyzed using Affymetrix Microarray Suite version 5.0, Expression Console™ version 1.1.1 (Affymetrix) and Genesprings (Silicon Genetics) softwares. Changes in gene expression rates more than 1-fold were considered as positive differential genes. For gene clustering, a plug-in program Genetrix (Epicenter Software) was used in conjunction with the Affymetrix softwares. Signals of the sample were normalized with the internal house-keeping control average in each microarray. The result of scatter plot analysis was shown in FIG. 5A.

Example 9

DNA Demethylation Assays

Figure 5B:
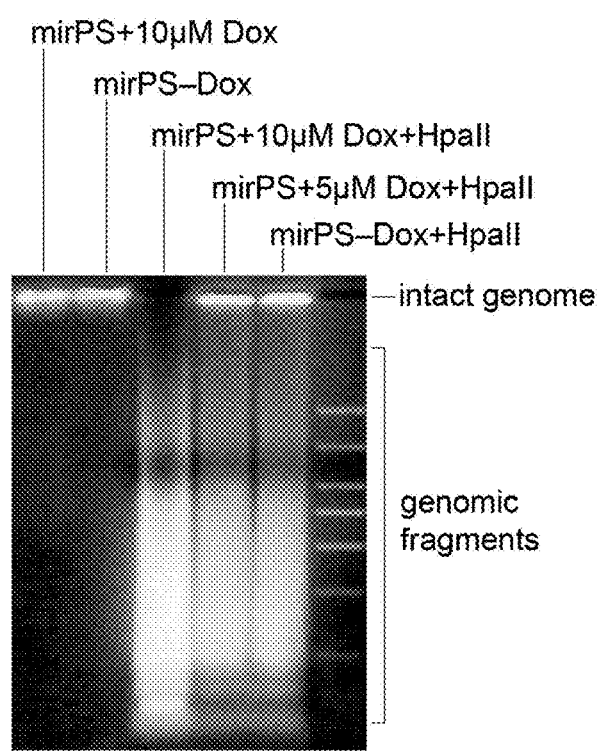
Figure 5C:
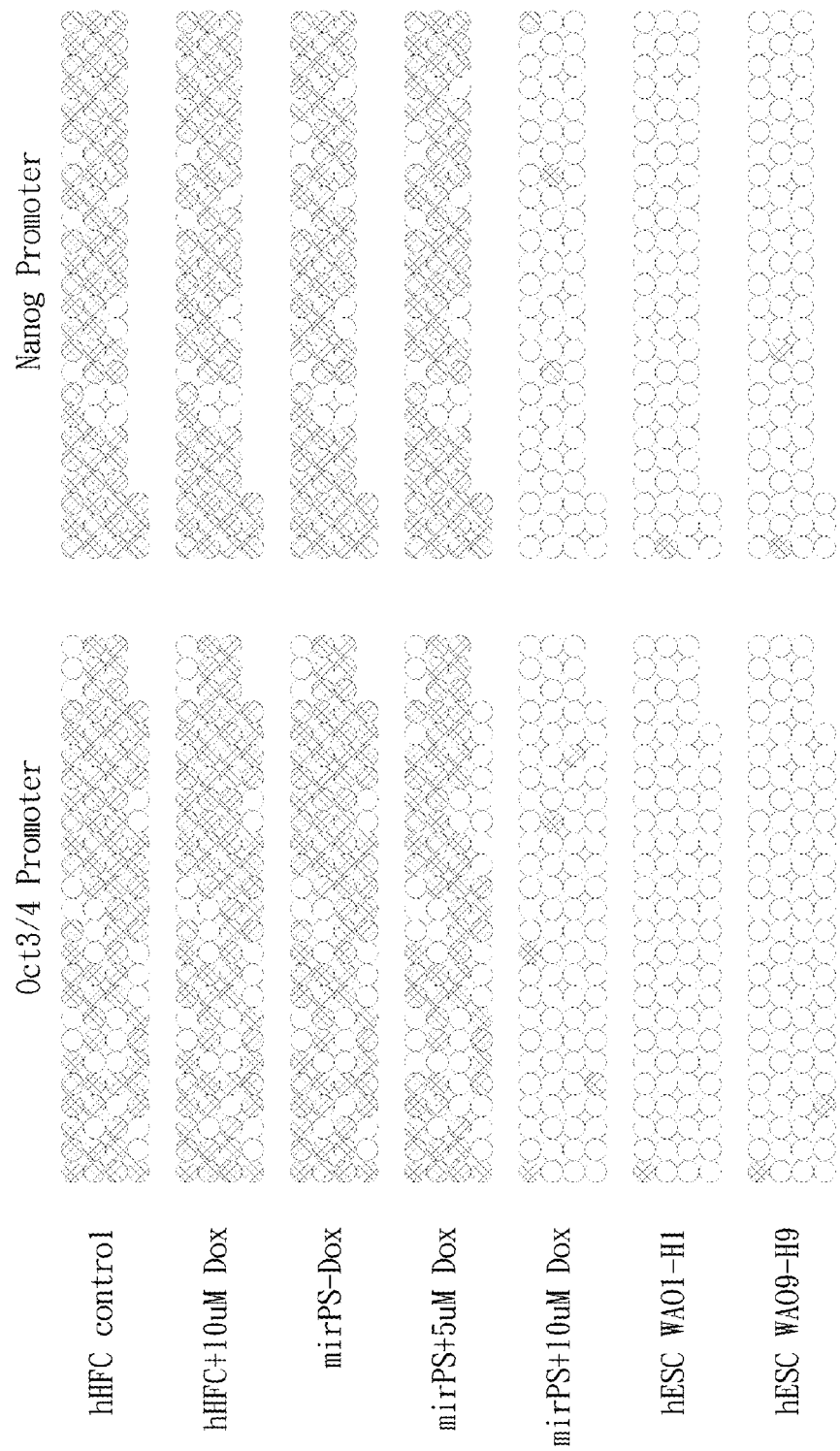
Figure 5D:
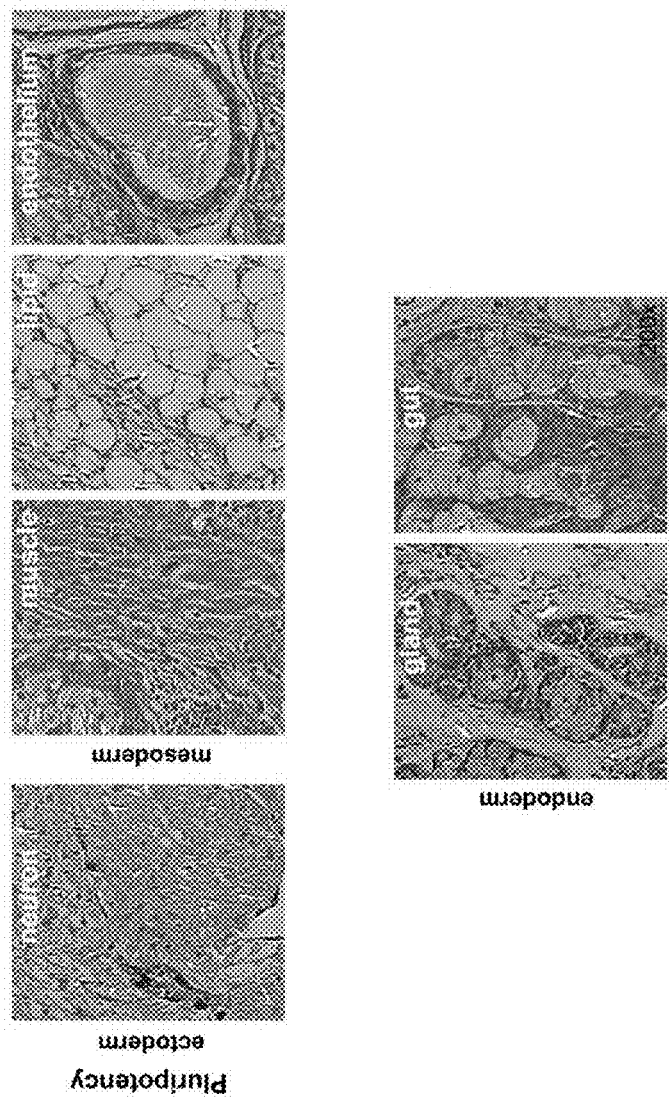

Genomic DNAs were isolated from about two million cells using a DNA Isolation Kit (Roche) and 1 µg of the isolated DNAs were further treated with bisulfite (CpGenome DNA modification kit, Chemicon, Temecula, Calif.), according to the manufacturers' suggestions. Meanwhile, 2 µg of untreated DNAs were digested with a CCGG-cutting restriction enzyme HpaII and then analyzed by 1% agarose gel electrophoresis to determine genome-wide demethylation (FIG. 5B). The treatment with bisulfite converted all unmethylated cytosine to uracil, while methylated cytosine remained as cytosine. For bisulfite DNA sequencing analyses, we amplified the promoter regions of Oct3/4 and Nanog with PCR. Primers included 5'-GAGGCTGGAG CAGAAG-GATT GCTTTGG-3' (SEQ.ID.NO.20) and 5'-CCCTCCT-GAC CCATCACCTC CACCACC-3' (SEQ.ID.NO.21) for Oct3/4, and 5'-TGGTTAGGTT GGTTTTAAAT TTTTG-3' (SEQ.ID.NO.22) and 5'-AACCCACCCT TATAAATTCT CAATTA-3' (SEQ.ID.NO.23) for Nanog. The bisulfite-modified DNAs (50 ng) were first mixed with the primers (total 100 pmole) in 1×PCR buffer, heated to 94° C. for 2 min, and immediately cooled on ice. Next, 25 cycles of PCR were performed as follows: 94° C. for 1 min and 70° C. for 3 min, using an Expand High Fidelity PCR kit (Roche). The amplified DNA product with a correct size was further fractionized by 3% agarose gel electrophoresis, purified with a gel extraction filter. (Qiagen), and then used in DNA sequencing. A detailed profile of the DNA methylation sites was generated by comparing the unchanged cytosine in the converted DNA sequence to the unconverted one. The result was shown in FIG. 5C.

Example 10

Implantation and Teratoma Formation

Approximately 5-10 mirPS cell-derived embryoid bodies (4- to 8-cell-stage) were suspended in 50 μl of a mixture of DMEM and Matrigel (2:1), followed by implantation into the uterus of a 6-week-old female pseudopregnant immunocompromised SCID-beige mouse. The pseudopregnant mice were prepared by intraperitoneal injection of 1 IU human menopausal gonadotrophin (HMG) for two days and then human chorionic gonadotrophin (hCG) for one more day. The cells and mice were not treated with Dox before or after implantation. The mice were anesthetized with 2.5% Avenin solution, 0.4 ml per mouse during implantation. Xenografted masses were monitored 3-4 weeks after the implantation or when the sizes were grown to over 100 mm$^3$. Cysts/teratomas were dissected and the volumes were calculated using the formula (length×width$^2$)/2. Cyst/teratoma lesions were counted, weighed and subjected to further histological analysis. Formation of teratoma-like tissue cysts was usually observed at approximately 2.5-week post-implantation. The result was shown in FIG. 5D.

Example 11

Cell Invasion Assay

Chamber inserts (12-μm pore size, Chemicon) were coated with 200 μg/ml of Matrigel alone or supplemented with 20% FBS in phenol red-free-DMEM with 1% L-glutamine and dried overnight under sterile conditions. Cells were harvested, washed, and resuspended in phenol red-free-DMEM to give a final cell density of 1×10$^5$ cells/ml. Five hundred microliters of the resulting cell suspension was then dispensed into the top chamber whereas DMEM conditioned medium (1.5 ml) was added to the bottom chamber to create a chemotactic gradient. Invasion was measured after overnight incubation at 37° C. for 16 hour. Top chambers were wiped with cotton wool, and invading cells on the underside of the membrane were fixed in 100% methanol for 10 min, air dried, stained in cresyl violet for 20 min, and gently rinsed in water. When dry, the cresyl violet stain on membranes was eluted using a 100% ethanol/0.2 M NaCltrate (1:1) wash for 20 min and absorbance read at 570 nm using a Precision Microplate Reader (Molecular Dynamics). The percentage of invading cells was calculated by comparison of absorbance in test samples against absorbance determined on membrane inserts that were not wiped (total cells). The result was shown in FIG. 6D.

Example 12

Cell Adhesion Assay

Cell Adhesion assay was performed as reported (Lin et al., 2007). Human bone marrow endothelial cells (hBMECs) were seeded at a density of 1×10$^5$ cells/ml in 96-well plates and washed with adhesion medium [RPMI 1640/0.1% BSA/20 mM HEPES (pH7.4)] before assays. Tested cells were trypsinized (tumor/cancer cells) or collagenase-digested (mirPS cells), washed in sterile saline, and resuspended at 1×10$^6$ cells/ml in PBS with 10 μM fura-4 acetoxymethyl ester (fluorescent probe, Sigma) for 1 hour at 37° C. in the dark. The cells were then pelleted, washed in serum-free medium containing 1% (v/v) of probenecid (100 mM) and incubated for 20 min in adhesion medium at 37° C. in the dark to activate the intracellular fluorescent probe. After that, 10$^5$ cells (in 300-μl cell suspension/well) were added to the confluent hBMEC endothelial monolayer and incubated for 50 min at 37° C. Non-adherent cells were removed using 2×250 μl washes of adhesion medium. Plates were read in a fluorescent plate reader (Molecular Dynamics) at 37° C. using an excitation wavelength of 485 nm and an emission wavelength of 530 nm. The result was shown in FIG. 6E.

Example 13

In Vivo Tumorigenecity Assay

The inventors xenografted NTera-2 cells (2×10$^6$ cells in a total volume of 100 μl Matrigel-PBS) into the flanks (e.g. right hind limb) of eight-week-old male mice (BALB/c nu/nu strain). Tumors were monitored weekly and in situ injection of pCMV-miR302s vector or pCMV-miR302d* was conducted one week after the NTera-2 xenograft. Five treatments (three-day intervals for each treatment) of 2 μg PEI-formulated pCMV-miR302s or pCMV-miR302d* vector (total 10 μg) per g mouse weight were performed. In vivo-jetPEI Delivery Reagent (Polyplus-transfection Inc., New York, N.Y.) was used as the manufacturer's suggestion. Samples were collected either three weeks post injection or when untreated tumors grew to an average size of approximately 100 mm$^3$. Major organs, such as the blood, brain, heart lung, liver, kidney and spleen, and the xenografts were removed for histological evaluation of tumor lesions and immunoreactive cytotoxicity. Tumor formation was monitored by palpation and tumor volume was calculated using the formula (length×width$^2$)/2. Tumor lesions were counted, dissected, weighed, and subjected to histological examination using H&E and immunostaining assays. Histological examination showed no detectable tissue lesions in brain, heart, lung, liver, kidney and spleen. The result was shown in FIGS. 8A-B.

Example 14

Immunostaining Assay

Tissue samples were fixed in 4% paraformaldehyde overnight at 4° C. The samples were washed sequentially with 1×PBS, methanol, isopropanol and tetrahydronaphthalene before embedded in paraffin wax. The embedded samples were then cut on a microtome at 7-10 μm thickness and mounted on clean TESPA-coated slides. Then, the slides were dewaxed with xylene and mounted under coverslips using mounting media (Richard Allan Scientific, Kalamazoo, Mich.) and stained by hematoxylin and eosin (H&E, Sigma) for morphological observation. Immunohistochemical (IHC) Staining Kits were purchased from Imgenex (San Diego, Calif.). Processes for antibody dilution and immunostaining were performed according to the manufacturers' suggestions. Primary antibodies included Oct3/4 (Santa Cruz), Sox2 (Santa Cruz), Nanog (Santa Cruz), CDK2 (Santa Cruz), cyclin D1 (Santa Cruz), cyclin D2 (Abcam), BMI-1 (Santa Cruz), and RGFP (Clontech). Secondary antibodies used were biotinylated goat anti-rabbit or biotinylated horse anti-mouse antibodies (Chemicon, Temecula, Calif.). Streptavidin-HRP was added as the tertiary antibody. After the slides were washed twice with PBT, the bound antibody was detected using DAB substrates. Positive results were observed under a 100× microscope with whole field scanning and measured at 200× magnification for quantitative analysis using a Metamorph Imaging program (Nikon 80i microscopic quantitation system). The result of scatter plot analysis was shown in FIG. 8C.

Example 15

Luciferase 3'-UTR Reporter Assay

Luciferase assays were performed using a modified pMir-Report miRNA Expression Reporter Vector System (Ambion). The mir-302 target sites (normal and/or mutant) were inserted in the 3'-UTR cloning site of the pMir-Report Luciferase Reporter vector. The two target sites were synthesized and separated by twelve-CAGT-repeats. Another pMir-Report β-gal Control vector was used as a no reporter control. We transfected 200 ng of the reporter vector into fifty thousand mirPS cells in the absence or presence of Dox treatment, using a FuGene HD reagent (Roche) following the manufacturer's suggestion. Cell lysates were harvested 48 hours after transfection, and the knockdown levels of luciferase were normalized and shown by ratios of relative luciferase activity (RFA), which was calculated by the level of luciferase activity in Dox-treated (Dox-on) mirPS cells divided by that of untreated (Dox-off) mirPS cells. Mir-434-expressing cells generated by electroporating hHFCs with pTet-On-tTS-miR434-5p were served as a negative control. The result was shown in FIG. 7B.

Example 16

TRAP Assay

Cells ($10^6$) were lysed with a CelLytic-M lysis/extraction reagent (Sigma) supplemented with protease inhibitors, Leupeptin, TLCK, TAME and PMSF, following the manufacturer's suggestion. Lysates were centrifuged at 12,000 rpm for 20 min at 4° C. and the supernatant was recovered. Protein concentrations were measured using an improved SOFTmax protein assay package on an E-max microplate reader (Molecular Devices, CA). Oligonucleotides 5'-AATCCGTC-GAGCAGAGTT-3' (SEQ.ID.NO.24) labeled with infrared Alexa Fluor 680 dye (TS Primer; Sigma-Genosys) and 5'-GT-GTAACCCTAACCCTAACCC-3' (CX primer; 30 μM) (SEQ.ID.NO.25) were used for detecting the PCR products. Telomerase inhibitors were directly added to the master mix. The optimal results for all tested cell lines were achieved using 50 ng proteins per reaction. After a 30-min incubation at 30° C., the samples were placed in a thermal cycler for 2 min at 94° C., followed by 35 PCR cycles of denaturation at 94° C. for 30 sec and synthesis at 57° C. for 30 sec as well as a single postsynthesis step at 57° C. for 30 sec. The PCR products were separated by electrophoresis on a 6% nondenaturing polyacrylamide gel and detected using Li-Cor Odyssey Infrared Imager and Odyssey Software v.10 (Li-Cor). The result was shown in FIG. 9A.

Example 17

Statistic Analysis

Any change over 75% of signal intensity in the analyses of immunostaining, western blotting and northern blotting was considered as a positive result, which in turn was analyzed and presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ was considered significant. All p values were determined from two-tailed tests.

Example 18

Cell Transformation and Induction of Pre-miRNA Expression

Competent *E. coli* DH5alpha cells are acquired from the z-competent *E. coli* transformation kit (Zymo Research, Irvine, Calif.) and transformed by mixing with 5 μg of a desired plasmid vector such as pLVX-Grn-miR302+367 or pLenti-EF1alpha-RGFP-miR302. Non-transformed bacterial cells are normally grown in Luria-Bertani (LB) broth supplemented with 10 mM $MgSO_4$ and 0.2 mM glucose at 37° C. with frequent agitation at 170 rpm, whereas the transformed bacterial cells are cultivated in the above LB broth further supplemented with additional 100 μg/ml ampicillin. For chemical induction of mir-302 expression, 0.5 to 2 ml of MOPS is added into 1 litter LB broth supplemented with 10 mM $MgSO_4$ and 0.2 mM glucose in the presence of 100 μg/mL ampicillin. For negative control, the transformed bacterial cells are cultivated in the above ampicillin-supplemented LB broth but without adding any chemical inducer.

Example 19

Human Cell Culture and Intracellular Mir-302 Delivery

Human primary epidermal skin cells (hpESCs) are isolated and dissociated from a minimum of 2 cubic mm by 4 mg/ml collagenase I digestion 37° C. for 35 min in fresh RPMI 1640 medium supplemented with 20% FBS. For culturing keratinocytes, the isolated cells are cultivated in EpiLife serum-free cell culture medium supplemented with human keratinocyte growth supplements (HKGS, Invitrogen, Carlsbad, Calif.) in the absence of antibiotics at 37° C. under 5% $CO_2$. Culture cells are passaged at 50%-60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer/tumor cell lines Colo-829, PC3, MCF7, HepG2 and Tera-2 were obtained from the American Type Culture Collection (ATCC, Rockville, Md.) and maintained according to manufacturer's suggestion's. For microRNA transfection, 15 μg of isolated miR-302 (and/or precursor thereof) is dissolved in 1 ml of fresh EpiLife medium and mixed with 50 μl of a liposomal/polysomal X-tremeGENE HP DNA transfection reagent. After 10 min incubation, the mixture is added into a 100-mm cell culture dish containing 50%-60% confluency of hpESCs or the cancer/tumor cells, respectively. The medium is replaced by fresh EpiLife medium with HKGS supplements or the conditioned medium suggested by ATCC 12 to 18 hours later. This transfection procedure may be repeated 3 to 4 times every three-four days to increase transfection efficiency. After cell morphology become sphere-like, the cells (mirPSCs) are grown and passaged in knockout DMEM/F-12 medium (Invitrogen) supplemented with 20% knockout serum, 1% MEM nonessential amino acids, 100 μM β-mercaptoethanol, 1 mM GlutaMax, 1 mM sodium pyruvate, 10 ng/ml bFGF, 10 ng/ml FGF-4, 5 ng/ml LIF, 100 IU/ml penicillin/100 μg/ml streptomycin, 0.1 μM A83-01, and 0.1 μM valproic acid (Stemgent, San Diego, Calif.), at 37° C. under 5% $CO_2$.

Example 20

Plasmid DNA/Total RNA/microRNA Extraction

Competent *E. coli* DH5alpha cells treated with plasmid transformation (from Example 18) are cultivated overnight in LB broth supplemented with 10 mM MgSO4 and 0.2 mM glucose at 37° C. with frequent agitation at 170 rpm. For inducing eukaryotic promoter-driven RNA and/or protein production, 0.5 to 2 ml of MOPS is added into every 1 litter of LB broth for the above bacterial cultivation and amplification. All amplified plasmid DNAs and expressed mRNAs/microRNA precursors (pre-miRNAs) are isolated together using a HiSpeed plasmid purification kit (Qiagen, Valencia, Calif.), following the manufacturer's protocol but with a minor modification that RNase A is not added into the P1 buffer. The final extracted products containing both plasmids and mRNAs/pre-miRNAs are dissolved in DEPC-treated ddH2O and stored at −80° C. before use. For purifying only the amplified plasmid vectors, RNase A is added into the P1 buffer and the extraction procedure is performed following the manufacturer's protocol.

Example 21

Purification of Mir-302 and its Precursors

Total RNAs isolated from the above Example 20 are further purified using a mirVana™ miRNA isolation kit (Ambion, Austin, Tex.), following the manufacturer's protocol. The final products are dissolved in DEPC-treated ddH2O and stored at −80° C. before use. Because bacterial RNAs are degraded very fast (a few hours) in nature while eukaryotic poly-A RNAs (mRNAs) and hairpin-like microRNA precursors (pre-miRNAs/pro-miRNAs) remain relatively stable at 4° C. (half-life up to 3-4 days), we can use this difference to acquire pure mRNAs and/or pre-miRNAs/pro-miRNAs for further applications. For example, RGFP mRNA can be used to identify the transfected cells, while pre-mir-302s/pro-mir-302s are useful for reprogramming somatic cells to hES-like iPS cells or treating human tumor/cancer cells. The purified pre-mir-302s/pro-mir-302s are also useful for reprogramming high-grade malignant cancer cells to a relatively benign low grade state, a very beneficial result for cancer therapy.

Example 22

In Vivo Wound Healing and Tissue Repair/Regeneration Test

The pro-mir-302 and its related plasmid vector were amplified and extracted as described in Examples 18 and 20 and further purified as described in Examples 20 and 21. Then, the isolated pro-mir-302 was formulated with a pre-prepared ointment containing cocoa butter, cottonseed oil, olive oil, sodium pyruvate, and white petrolatum. The concentration of pro-mir-302 in the prepared ointment base is about 10 μg/mL. Skin open wounds in mice were generated by scalpel dissection; approximately 0.5×0.5 square cm. Ointment (about 0.3 mL) was directly applied to cover the whole wounded area and further sealed by liquid bandage.

Example 23

In Vivo Liver Cancer Therapy Trials

Xenografting human liver cancers into immunocompromised SCID-beige mice is a valid animal model for studying liver cancer metastasis and therapy. To establish this model, we mixed 5 million human hepatocarcinoma (HepG2) cells with 100 μL of matrix gel and subcutaneously engrafted the mixture into each flank of the mouse hind limbs, respectively. As a result, both sides of the mouse hind limbs were subjected to approximately the same amount of cancer cell engraftment. Cancers were observed about two weeks post-engraftment and sized about 15.6±8 $mm^3$ in average (starting cancer size before treatment). For each mouse, we selected the side with a larger cancer as the treatment group and the other smaller one as the control group. Since the same mouse was treated with a blank formulation reagent (negative control) in one side and the formulated drug (pro-mir-302) in the other side, the results so obtained can minimize any possible variation due to individual differences.

To deliver pro-mir-302 into the targeted cancer regions in vivo, we contracted a professional formulation company, Latitude (San Diego, Calif.), to liposomally encapsulate pro-mir-302 into 160 to 200 nm-diameter particles. These pro-mir-302-containing nanoparticles have been tested to be almost 100% stable at room temperature for over two weeks and at 4° C. for over one month, whereas other synthetic siRNA mimics (siRNA-302) were all quickly degraded over 50% within 3 to 5 days under the same conditions, indicating that pro-miRNA rather than siRNA is stable enough to be used as a drug for therapy. For toxicity assay, we have further injected maximally 300 μL of the formulated pro-mir-302 (1 mg/mL) into the mouse tail vein (n=8), respectively, and observed no detectable side effect in all tested mice over six months. In general, non-modified ribonucleic acids are relatively not immunogenic and can be easily metabolized by tissue cells, rendering a safe tool for in vivo therapy.

For testing drug potency, we subcutaneously injected 200 μL of the formulated pro-mir-302 in one side and 200 μL of the blank formulation reagent in the other side of the mice, respectively, and continued the same injection pattern for three times (one injection per week). The drug and reagent were applied to the surrounding region of the cancer site and absorbed by the cancer and its surrounding tissues within 18 hours. Samples were collected one week after the third injection. Hearts, livers, kidneys and the engrafted cancers were removed for further histological examination. Tumor formation was monitored by palpation and tumor volume was calculated using the formula (length×width$^2$)/2. Tumor lesions were counted, dissected, weighed, and subjected to histological examination using H&E and immunostaining assays. Histological examination showed no detectable tissue lesions in heart, liver, and kidney. The results were shown in FIGS. 15, 16 and 17.

REFERENCES

The following references are hereby incorporated by reference as if fully set forth herein:
1. Lin et al. (2008). Mir-302 reprograms human skin cancer cells into a pluripotent ES-cell-like state. RNA 14, 2115-2124.
2. Lin et al. (2010). MicroRNA miR-302 inhibits the tumorigenecity of human pluripotent stem cells by coordinate suppression of CDK2 and CDK4/6 cell cycle pathways. Cancer Res. 70, 9473-9482.
3. Lin et al. (2011). Regulation of somatic cell reprogramming through inducible mir-302 expression. Nucleic Acids Res. 39, 1054-1065.
4. Takahashi et al. (2006). Induction of pluripotent stem cells from mouse embryonic and adult fibroblast cultures by defined factors. Cell 126, 663-676.
5. Yu et al. (2007). Induced pluripotent stem cell lines derived from human somatic cells. Science 318, 1917-1920.
6. Wernig et al. (2007). In vitro reprogramming of fibroblasts into a pluripotent ES-cell-like state. Nature 448, 318-324.
7. Wang et al. (2008). Embryonic stem cell-specific microRNAs regulate the G1-S transition and promote rapid proliferation. Nat. Genet. 40, 1478-1483.
8. Deng et al. (1995). Mice lacking p21Cip1/Waf undergo normal development, but are defective in G1 checkpoint control. Cell 82, 675-684.
9. Yabuta et al. (2007). Lats2 is an essential mitotic regulator required for the coordination of cell division. J Biol Chem. 282, 19259-19271.
10. Judson et al. (2009). Embryonic stem cell-specific microRNAs promote induced pluripotency. Nat Biotechnol. 27, 459-461.
11. Barroso-deUesus et al. (2008) Embryonic stem cell-specific miR302-367 cluster: human gene structure and functional characterization of its core promoter. Mol Cell Biol. 28, 6609-6619.
12. Ying S Y and Lin S L. (2004). Intron-derived microRNAs—Fine tuning of gene functions. Gene 342, 25-28.
13. Suh et al. (2004). Human embryonic stem cells express a unique set of microRNAs. Dev. Biol. 270, 488-498.
14. Tang et al. (2007). Maternal microRNAs are essential for mouse zygotic development. Genes Dev. 21, 644-648.
15. Lin et al. (2003). A novel RNA splicing-mediated gene silencing mechanism potential for genome evolution. Biochem Biophys Res Commun. 310, 754-760.
16. Lin et al. (2006) Gene silencing in vitro and in vivo using intronic microRNAs. Methods Mol Biol. 342, 295-312.
17. Grimm et al. (2006). Fatality in mice due to oversaturation of cellular microRNA/short hairpin RNA pathways. Nature 441, 537-541.
18. Lin et al. (2005). Asymmetry of intronic pre-microRNA structures in functional RISC assembly. Gene 356, 32-38.
19. Marson et al. (2008). Connecting microRNA genes to the core transcriptional regulatory circuitry of embryonic stem cells. Cell 134, 521-533.
20. Card et al. (2008). Oct4/Sox2-regulated miR-302 targets cyclin D1 in human embryonic stem cells. Mol. Cell Biol. 28, 6426-6438.
21. Jacobs et al. (1999). The oncogene and Polycomb-group gene bmi-1 regulates cell proliferation and senescence through the ink4a locus. Nature 397, 164-168.
22. Parry et al. (1995). Lack of cyclin D-Cdk complexes in Rb-negative cells correlated with high levels of p16INK4/MTS1 tumor suppressor gene product. EMBO J. 14, 503-511.
23. Quelle et al. (1995). Alternative reading frames of the NK4a tumor suppressor gene encode two unrelated proteins capable of inducing cell cycle arrest. Cell 83, 993-1000.
24. Kamijo et al. (1997). Tumor suppression at the mouse INK4a locus mediated by the alternative reading frame product p19ARF. Cell 91, 649-659.
25. Burdon et al. (2002). Signaling, cell cycle and pluripotency in embryonic stem cells. Trends Cell Biol. 12, 432-438.
26. Jirmanova et al. (2002). Differential contributions of ERK and PI3-kinase to the regulation of cyclin D1 expression and to the control of the G1/S transition in mouse embryonic stem cells. Oncogene 21, 5515-5528.
27. Stead et al. (2002). Pluripotent cell division cycles are driven by ectopic Cdk2, cyclin A/E and E2F activities. Oncogene 21, 8320-8333.
28. Andrews et al. (1984). Pluripotent embryonal carcinoma clones derived from the human teratocarcinoma cell line Tera-2. Differentiation in vivo and in vitro. Lab Invest. 50, 147-162.
29. Banito et al. (2009). Senescence impairs successful reprogramming to pluripotent stem cells. Gene Dev. 23, 2134-2139.
30. Feng et al. (2010). Hemangioblastic derivatives from human induced pluripotent stem cells exhibit limited expansion and early senescence. Stem Cell in press.
31. Dimri et al. (2002). The Bmi-1 oncogene induces telomerase activity and immortalizes human mammary epithelial cells. Cancer Res. 62, 4736-4745.
32. Won et al. (2002). Sp1 and Sp3 recruit histone deacetylase to repress transcription of human telomerase reverse transcriptase (hTERT) promoter in normal human somstic cells. J Biol Chem. 277, 38230-38238.
33. Zhu et al. (2008). Lysine-specific demethylase 1 (LSD1) is required for the transcriptional repression of the telomerase reverse transcriptase (hTERT) gene. PloS One 3, e1446.
34. EU Pat. No. EP2198025 to Lin.
35. U.S. Pat. Nos. 5,843,780, 6,200,806, 7,029,913, and 7,220,584 to Thomson.
36. U.S. Pat. Nos. 6,090,622, 6,245,566, and 6,331,406 to Gearhart.
37. U.S. Pat. No. 6,875,607 to Reubinoff.
38. U.S. Pat. No. 7,250,255 to Shinya Yamanaka.

It is understood that the examples and embodiments described herein are for illustrative purposes only and that various modifications or changes in light thereof will be suggested to persons skilled in the art, and are to be included within the spirit and purview of the invention as set forth in the appended claims. All publications and patents cited herein are incorporated herein by reference in their entirety for all purposes.

TABLE 1 related to Example 4.

| Probe | Sequence |
|---|---|
| Oct3/4 | 5'-GCAGTGTGGG TTTCGGGCAC TGCAGGAACA AATTCTCCAG GTTGCCTCTC ACTCGGTTCT CGATACTGGT TCGCTTTCTC TTTCGGGCCT GCACGAGGGT TTCTGCTTTG-3' (SEQ.ID.NO. 26) |
| Sox2 | 5'-TGCTGTAGGT GGGCGAGCCG TTCATGTAGG TCTGCGAGCT GGTCATGGAG TTGTACTGCA GGGCGCTCAC GTCGTAGCGG TGCATGGGCT GCATCTGCGC TGCGCCGTGC-3' (SEQ.ID.NO. 27) |
| Nanog | 5'-CGTGTGAGGC ATCTCAGCAG AAGACATTTG CAAGGATGGA TAGTTTTCTT CAGGCCCACA AATCACAGGC ATAGGTGAAG ATTCTTTACA GTCGGATGCT TCAAAGCAAG-3' (SEQ.ID.NO. 28) |
| Lin28 | 5'-AGGTCCGGTG ACACGGATGG ATTCCAGACC CTTGGCTGAC TTCTTAAAGG TGAACTCCAC TGCCTCACCC TCCTTCAAGC TCCGGAACCC TTCCATGTGC AGCTTACTCT-3' (SEQ.ID.NO. 29) |
| UTF1 | 5'-CTGCTGGGCC AGCGCGGCCG ACACGCGGCG GTAGGTGGGC AGGGCCTGGC GGCGGTCCAG GAGCAGCGCG CGCCACACGG CCGGTTGCAG CAGCGTCCCC AGCAGCAGCT-3' (SEQ.ID.NO. 30) |
| Klf4 | 5'-CTGCTCGACG GCGACGACGA AGAGGAGGCT GACGCTGACG AGGACACGGT GGCGGCCACT GACTCCGGAG GATGGGTCAG CGAATTGGAG AGAATAAAGT CCAGGTCCAG-3' (SEQ.ID.NO. 31) |
| FUT3 | 5'-GAGCCCTAGG GGATCCAGTG GCATCGTCTC GGGACACACG CAGGTAGGAG AAGAAACACA CAGCCACCAG CAGCTGAAAT AGCAGTGCGG CCAGACAGCG GCGCCATGGC-3' (SEQ.ID.NO. 32) |
| RGFP | 5'-CGAAGGGGTT GCCGTCGCCC TCGCCCTCGC ACTTGAAGTA GTGGCCGTTC ACGGTGCCCT CCATGTACAT CTTGATGCGC ATACTCTCCT TCAGCAGGCC GCTCACCATA-3' (SEQ.ID.NO. 33) |
| β-actin | 5'-AATGTCACGC ACGATTTCCC GCTCGGCCGT GGTGGTGAAG CTGTAGCCGC GCTCGGTGAG GATCTTCATG AGGTAGTCAG TCAGGTCCCG GCCAGCCAGG TCCAGAGCGA-3' (SEQ.ID.NO. 34) |

The invention claimed is:

1. A method for inducing a gene silencing effect on BMI-1 and then leading to an increase of p16Ink4a or p14Arf tumor suppressor expression in vivo, comprising:

delivering a pro-mir-302 capable of being processed into at least one hairpin-like microRNA precursor in a human cell substrate to an amount, wherein said at least one hairpin-like microRNA precursor contains a seed sequence SEQ ID NO: 3 and said human cell substrate contains at least a cancerous cell type of human liver cancer, and wherein the amount of said hairpin-like microRNA precursor is higher than 200 micrograms per delivery in vivo.

2. The method of claim 1, wherein said step of delivering said pro-mir-302 further comprises providing said pro-mir-302 from prokaryotic competent cells.

3. The method of claim 2, wherein said pro-mir-302 is produced by said prokaryotic competent cells and is a precursor of mir-302.

4. The method of claim 2, wherein said step of providing said pro-mir-302 further comprises isolating said pro-mir-302 from an extract or a lysate of said prokaryotic competent cells.

5. The method of claim 1, wherein said step of delivering said pro-mir-302 capable of being processed into at least one hairpin-like microRNA precursor further comprises letting said pro-mir-302 be processed into mir-302a, mir-302b, mir-302c, and/or mir-302d in said human cell substrate.

6. The method of claim 1, wherein said gene silencing effect further comprises an effect leading to reprogram high-grade malignant cancers to a relatively benign low-grade state.

7. The method of claim 1, wherein said pro-mir-302 is delivered into said human cell substrate by a gene delivery method.

8. The method of claim 1, wherein said pro-mir-302 is used as a drug for treating human liver cancer.

9. The method of claim 1, wherein said pro-mir-302 is useful for pharmaceutical and/or therapeutic applications.

* * * * *

SEQUENCE LISTING

<160> NUMBER OF SEQ ID NOS: 75

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotides

<400> SEQUENCE: 1
gctaagccag gc                                                        12

<210> SEQ ID NO 2
<211> LENGTH: 12
<212> TYPE: DNA
<213> ORGANISM: Artificial Sequence
<220> FEATURE:
<223> OTHER INFORMATION: Synthetic Oligonucleotides

<400> SEQUENCE: 2
gcctggctta gc                                                        12

<210> SEQ ID NO 3
<211> LENGTH: 17
<212> TYPE: RNA
<213> ORGANISM: Artificial Sequence
<220> FEATURE:
<223> OTHER INFORMATION: Synthetic Oligonucleotides

```
<400> SEQUENCE: 3
uaagugcuuc cauguuu                                                    17

<210> SEQ ID NO 4
<211> LENGTH: 8
<212> TYPE: DNA
<213> ORGANISM: Artificial Sequence
<220> FEATURE:
<223> OTHER INFORMATION: Synthetic Oligonucleotides

<400> SEQUENCE: 4 gtaagagk                                                               8

<210> SEQ ID NO 5
<211> LENGTH: 10
<212> TYPE: DNA
<213> ORGANISM: Artificial Sequence
<220> FEATURE:
<223> OTHER INFORMATION: Synthetic Oligonucleotides

<400> SEQUENCE: 5 gwkscyrcag                                                            10

<210> SEQ ID NO 6
<211> LENGTH: 7
<212> TYPE: DNA
<213> ORGANISM: Artificial Sequence
<220> FEATURE:
<223> OTHER INFORMATION: Synthetic Oligonucleotides

<400> SEQUENCE: 6 tactway                                                                7

<210> SEQ ID NO 7
<211> LENGTH: 17
<212> TYPE: DNA
<213> ORGANISM: Artificial Sequence
<220> FEATURE:
<223> OTHER INFORMATION: Synthetic Oligonucleotides

<400> SEQUENCE: 7 tytyctttttt tttttts                                                   17

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (15)..(15)
<223> OTHER INFORMATION: n is a, c, g, or t

<400> SEQUENCE: 8
tctctctctc tctcnctag                                                  19

<210> SEQ ID NO 9
<211> LENGTH: 91
<212> TYPE: DNA
<213> ORGANISM: Artificial Sequence
<220> FEATURE:
<223> OTHER INFORMATION: Synthetic Oligonucleotides

<400> SEQUENCE: 9
gtcacgcgtt cccaccactt aaacgtggat gtacttgctt tgaaactaaa gaagtaagtg     60
```
cttccatgtt ttggtgatgg atagatctct c    91

<210> SEQ ID NO 10
<211> LENGTH: 91
<212> TYPE: DNA
<213> ORGANISM: Artificial Sequence
<220> FEATURE:
<223> OTHER INFORMATION: Synthetic Oligonucleotides

<400> SEQUENCE: 10
gagagatcta tccatcacca aaacatggaa gcacttactt ctttagtttc aaagcaagta    60
catccacgtt taagtggtgg aacgcgtga c    91

<210> SEQ ID NO 11
<211> LENGTH: 95
<212> TYPE: DNA
<213> ORGANISM: Artificial Sequence
<220> FEATURE:
<223> OTHER INFORMATION: Synthetic Oligonucleotides

<400> SEQUENCE: 11
atagatctct cgctcccttc aactttaaca tggaagtgct ttctgtgact ttgaaagtaa    60
gtgcttccat gttttagtag gagtcgctca tatga    95

<210> SEQ ID NO 12
<211> LENGTH: 95
<212> TYPE: DNA
<213> ORGANISM: Artificial Sequence
<220> FEATURE:
<223> OTHER INFORMATION: Synthetic Oligonucleotides

<400> SEQUENCE: 12
tcatatgagc gactccctact aaaacatgga agcacttact ttcaaagtca cagaaagcac    60
ttccatgtta aagttgaagg gagcgagaga tctat    95

<210> SEQ ID NO 13
<211> LENGTH: 90
<212> TYPE: DNA
<213> ORGANISM: Artificial Sequence
<220> FEATURE:
<223> OTHER INFORMATION: Synthetic Oligonucleotides

<400> SEQUENCE: 13
ccatatggct acctttgctt taacatggag gtacctgctg tgtgaaacag aagtaagtgc    60
ttccatgttt cagtggaggc gtctagacat    90

<210> SEQ ID NO 14
<211> LENGTH: 90
<212> TYPE: DNA
<213> ORGANISM: Artificial Sequence
<220> FEATURE:
<223> OTHER INFORMATION: Synthetic Oligonucleotides

<400> SEQUENCE: 14
atgtctagac gcctccactg aaacatggaa gcacttactt ctgtttcaca cagcaggtac    60
ctccatgtta aagcaaaggt agccatatgg    90

<210> SEQ ID NO 15
<211> LENGTH: 82
<212> TYPE: DNA
<213> ORGANISM: Artificial Sequence
<220> FEATURE:

```
<223> OTHER INFORMATION: Synthetic Oligonucleotides

<400> SEQUENCE: 15
cgtctagaca taacactcaa acatggaagc acttagctaa gccaggctaa gtgcttccat      60
gtttgagtgt tcgcgatcgc at                                              82

<210> SEQ ID NO 16
<211> LENGTH: 82
<212> TYPE: DNA
<213> ORGANISM: Artificial Sequence
<220> FEATURE:
<223> OTHER INFORMATION: Synthetic Oligonucleotides

<400> SEQUENCE: 16
atgcgatcgc gaacactcaa acatggaagc acttagcctg gcttagctaa gtgcttccat      60
gtttgagtgt tatgtctaga cg                                              82

<210> SEQ ID NO 17
<211> LENGTH: 105
<212> TYPE: DNA
<213> ORGANISM: Artificial Sequence
<220> FEATURE:
<223> OTHER INFORMATION: Synthetic Oligonucleotides

<400> SEQUENCE: 17
gcagatctcg aggtaccgac gcgtcctctt tactttaaca tggaaattaa gtgcttccat      60
gtttgagtgg tgtggcgcga tcgatatctc tagaggatcc acatc                    105

<210> SEQ ID NO 18
<211> LENGTH: 105
<212> TYPE: DNA
<213> ORGANISM: Artificial Sequence
<220> FEATURE:
<223> OTHER INFORMATION: Synthetic Oligonucleotides

<400> SEQUENCE: 18
gatgtggatc ctctagagat atcgatcgcg ccacaccact caaacatgga agcacttaat      60
ttccatgtta aagtaaagag gacgcgtcgg tacctcgaga tctgc                    105

<210> SEQ ID NO 19
<211> LENGTH: 23
<212> TYPE: DNA
<213> ORGANISM: Artificial Sequence
<220> FEATURE:
<223> OTHER INFORMATION: Synthetic Oligonucleotides

<400> SEQUENCE: 19
tcactgaaac atggaagcac tta                                             23

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
gaggctggag cagaaggatt gctttgg                                         27

<210> SEQ ID NO 21
<211> LENGTH: 27
<212> TYPE: DNA
<213> ORGANISM: Artificial Sequence
```

```
<220> FEATURE:
<223> OTHER INFORMATION: Primer

<400> SEQUENCE: 21
ccctcctgac ccatcacctc caccacc                                            27

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
tggttaggtt ggttttaaat ttttg                                              25

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
aacccaccct tataaattct caatta                                             26

<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotides

<400> SEQUENCE: 24
aatccgtcga gcagagtt                                                      18

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotides

<400> SEQUENCE: 25
gtgtaaccct aaccctaacc c                                                  21

<210> SEQ ID NO 26
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 26
gcagtgtggg tttcgggcac tgcaggaaca aattctccag gttgcctctc actcggttct        60
cgatactggt tcgctttctc tttcgggcct gcacgagggt ttctgctttg                  110

<210> SEQ ID NO 27
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 27
```
tgctgtaggt gggcgagccg ttcatgtagg tctgcgagct ggtcatggag ttgtactgca    60
gggcgctcac gtcgtagcgg tgcatgggct gcatctgcgc tgcgccgtgc             110

<210> SEQ ID NO 28
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 28
cgtgtgaggc atctcagcag aagacatttg caaggatgga tagttttctt caggcccaca    60
aatcacaggc ataggtgaag attctttaca gtcggatgct tcaaagcaag             110

<210> SEQ ID NO 29
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 29
aggtccggtg acacggatgg attccagacc cttggctgac ttcttaaagg tgaactccac    60
tgcctcaccc tccttcaagc tccggaaccc ttccatgtgc agcttactct             110

<210> SEQ ID NO 30
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 30
ctgctgggcc agcgcggccg acacgcggcg gtaggtgggc agggcctggc ggcggtccag    60
gagcagcgcg cgccacacgg ccggttgcag cagcgtcccc agcagcagct             110

<210> SEQ ID NO 31
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 31
ctgctcgacg gcgacgacga agaggaggct gacgctgacg aggacacggt ggcggccact    60
gactccggag gatgggtcag cgaattggag agaataaagt ccaggtccag             110

<210> SEQ ID NO 32
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 32
gagccctagg ggatccagtg gcatcgtctc gggacacacg caggtaggag aagaaacaca    60
cagccaccag cagctgaaat agcagtgcgg ccagacagcg gcgccatggc             110

<210> SEQ ID NO 33
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 33
cgaaggggtt gccgtcgccc tcgccctcgc acttgaagta gtggccgttc acggtgccct    60
ccatgtacat cttgatgcgc atactctcct tcagcaggcc gctcaccata              110

<210> SEQ ID NO 34
<211> LENGTH: 110
<212> TYPE: DNA
<213> ORGANISM: Artificial Sequence
<220> FEATURE:
<223> OTHER INFORMATION: Synthetic Oligonucleotides

<400> SEQUENCE: 34
aatgtcacgc acgatttccc gctcggccgt ggtggtgaag ctgtagccgc gctcggtgag    60
gatcttcatg aggtagtcag tcaggtcccg gccagccagg tccagagcga              110

<210> SEQ ID NO 35
<211> LENGTH: 6
<212> TYPE: RNA
<213> ORGANISM: Artificial Sequence
<220> FEATURE:
<223> OTHER INFORMATION: Synthetic oligonucleotides

<400> SEQUENCE: 35 guragu                                                                6

<210> SEQ ID NO 36
<211> LENGTH: 10
<212> TYPE: DNA
<213> ORGANISM: Artificial Sequence
<220> FEATURE:
<223> OTHER INFORMATION: Synthetic oligonucleotides

<400> SEQUENCE: 36
gtaagaggat                                                           10

<210> SEQ ID NO 37
<211> LENGTH: 8
<212> TYPE: DNA
<213> ORGANISM: Artificial Sequence
<220> FEATURE:
<223> OTHER INFORMATION: Synthetic oligonucleotides

<400> SEQUENCE: 37 gtaagagt                                                              8

<210> SEQ ID NO 38
<211> LENGTH: 7
<212> TYPE: DNA
<213> ORGANISM: Artificial Sequence
<220> FEATURE:
<223> OTHER INFORMATION: Synthetic oligonucleotides

<400> SEQUENCE: 38 gtagagt                                                               7

<210> SEQ ID NO 39
<211> LENGTH: 6
<212> TYPE: DNA
<213> ORGANISM: Artificial Sequence
<220> FEATURE:
<223> OTHER INFORMATION: Synthetic oligonucleotides

```
<400> SEQUENCE: 39 gtaagt                                                                    6

<210> SEQ ID NO 40
<211> LENGTH: 7
<212> TYPE: DNA
<213> ORGANISM: Artificial Sequence
<220> FEATURE:
<223> OTHER INFORMATION: Synthetic oligonucleotides
<220> FEATURE:
<221> NAME/KEY: misc_feature
<222> LOCATION: (6)..(6)
<223> OTHER INFORMATION: n is a, c, g, t or u

<400> SEQUENCE: 40 ctrayng                                                                   7

<210> SEQ ID NO 41
<211> LENGTH: 12
<212> TYPE: DNA
<213> ORGANISM: Artificial Sequence
<220> FEATURE:
<223> OTHER INFORMATION: Synthetic oligonucleotides

<400> SEQUENCE: 41
gatatcctgc ag                                                            12

<210> SEQ ID NO 42
<211> LENGTH: 8
<212> TYPE: DNA
<213> ORGANISM: Artificial Sequence
<220> FEATURE:
<223> OTHER INFORMATION: Synthetic oligonucleotides

<400> SEQUENCE: 42 ggctgcag                                                                  8

<210> SEQ ID NO 43
<211> LENGTH: 6
<212> TYPE: DNA
<213> ORGANISM: Artificial Sequence
<220> FEATURE:
<223> OTHER INFORMATION: Synthetic oligonucleotides

<400> SEQUENCE: 43 ccacag                                                                    6

<210> SEQ ID NO 44
<211> LENGTH: 7
<212> TYPE: DNA
<213> ORGANISM: Artificial Sequence
<220> FEATURE:
<223> OTHER INFORMATION: Synthetic oligonucleotides

<400> SEQUENCE: 44 tactaac                                                                   7

<210> SEQ ID NO 45
<211> LENGTH: 7
<212> TYPE: DNA
<213> ORGANISM: Artificial Sequence
<220> FEATURE:
<223> OTHER INFORMATION: Synthetic oligonucleotides

<400> SEQUENCE: 45 tacttat                                                                   7
```

-continued

```
<210> SEQ ID NO 46
<211> LENGTH: 11
<212> TYPE: RNA
<213> ORGANISM: Artificial Sequence
<220> FEATURE:
<223> OTHER INFORMATION: Synthetic oligonucleotides

<400> SEQUENCE: 46
wuccaagggg g                                                             11

<210> SEQ ID NO 47
<211> LENGTH: 5
<212> TYPE: DNA
<213> ORGANISM: Artificial Sequence
<220> FEATURE:
<223> OTHER INFORMATION: Synthetic oligonucleotides

<400> SEQUENCE: 47 gtaag                                                                     5

<210> SEQ ID NO 48
<211> LENGTH: 6
<212> TYPE: DNA
<213> ORGANISM: Artificial Sequence
<220> FEATURE:
<223> OTHER INFORMATION: Synthetic oligonucleotides

<400> SEQUENCE: 48 ctgcag                                                                    6

<210> SEQ ID NO 49
<211> LENGTH: 69
<212> TYPE: RNA
<213> ORGANISM: Artificial Sequence
<220> FEATURE:
<223> OTHER INFORMATION: Synthetic oligonucleotides

<400> SEQUENCE: 49
ccaccacuua aacguggaug uacuugcuuu gaaacuaaag aaguaagugc uuccauguuu         60
uggugaugg                                                                69

<210> SEQ ID NO 50
<211> LENGTH: 73
<212> TYPE: RNA
<213> ORGANISM: Artificial Sequence
<220> FEATURE:
<223> OTHER INFORMATION: Synthetic oligonucleotides

<400> SEQUENCE: 50
gcucccuuca acuuuaacau ggaagugcuu ucgugacuu ugaaaguaag ugcuuccaug          60
uuuuaguagg agu                                                           73

<210> SEQ ID NO 51
<211> LENGTH: 68
<212> TYPE: RNA
<213> ORGANISM: Artificial Sequence
<220> FEATURE:
<223> OTHER INFORMATION: Synthetic oligonucleotides

<400> SEQUENCE: 51
ccuuugcuuu aacauggagg uaccugcugu gugaaacaga aguaagugcu uccauguuuc        60
aguggagg                                                                 68
```

```
<210> SEQ ID NO 52
<211> LENGTH: 62
<212> TYPE: RNA
<213> ORGANISM: Artificial Sequence
<220> FEATURE:
<223> OTHER INFORMATION: Synthetic oligonucleotides

<400> SEQUENCE: 52
uaacacucaa acauggaagc acuuagcuaa gccaggcuaa gugcuuccau guuugagugu    60
uc                                                                  62

<210> SEQ ID NO 53
<211> LENGTH: 23
<212> TYPE: RNA
<213> ORGANISM: Artificial Sequence
<220> FEATURE:
<223> OTHER INFORMATION: Synthetic oligonucleotides

<400> SEQUENCE: 53
uaagugcuuc caguuuugg uga                                            23

<210> SEQ ID NO 54
<211> LENGTH: 23
<212> TYPE: RNA
<213> ORGANISM: Artificial Sequence
<220> FEATURE:
<223> OTHER INFORMATION: Synthetic oligonucleotides

<400> SEQUENCE: 54
uaagugcuuc caguuuuag uag                                            23

<210> SEQ ID NO 55
<211> LENGTH: 23
<212> TYPE: RNA
<213> ORGANISM: Artificial Sequence
<220> FEATURE:
<223> OTHER INFORMATION: Synthetic oligonucleotides

<400> SEQUENCE: 55
uaagugcuuc caguuucag ugg                                            23

<210> SEQ ID NO 56
<211> LENGTH: 23
<212> TYPE: RNA
<213> ORGANISM: Artificial Sequence
<220> FEATURE:
<223> OTHER INFORMATION: Synthetic oligonucleotides

<400> SEQUENCE: 56
uaagugcuuc caguuugag ugu                                            23

<210> SEQ ID NO 57
<211> LENGTH: 22
<212> TYPE: DNA
<213> ORGANISM: Homo sapiens

<400> SEQUENCE: 57
gtttcagtat tagatgcact ta                                            22

<210> SEQ ID NO 58
<211> LENGTH: 22
<212> TYPE: DNA
<213> ORGANISM: Homo sapiens

<400> SEQUENCE: 58
```

-continued

| | |
|---|---|
| attttgagaa tgctgacact tt | 22 |

<210> SEQ ID NO 59
<211> LENGTH: 22
<212> TYPE: DNA
<213> ORGANISM: Homo sapiens

<400> SEQUENCE: 59

| | |
|---|---|
| gcacgatttc attgaacact tc | 22 |

<210> SEQ ID NO 60
<211> LENGTH: 20
<212> TYPE: DNA
<213> ORGANISM: Homo sapiens

<400> SEQUENCE: 60

| | |
|---|---|
| cctgtgatgc tgggcacttc | 20 |

<210> SEQ ID NO 61
<211> LENGTH: 23
<212> TYPE: DNA
<213> ORGANISM: Homo sapiens

<400> SEQUENCE: 61

| | |
|---|---|
| ccattccatt cgaaaagcac ttt | 23 |

<210> SEQ ID NO 62
<211> LENGTH: 27
<212> TYPE: DNA
<213> ORGANISM: Homo sapiens

<400> SEQUENCE: 62

| | |
|---|---|
| aggctcagat gtcgtaattt gcactta | 27 |

<210> SEQ ID NO 63
<211> LENGTH: 23
<212> TYPE: DNA
<213> ORGANISM: Homo sapiens

<400> SEQUENCE: 63

| | |
|---|---|
| cagcaatgac tgtgatgcac tta | 23 |

<210> SEQ ID NO 64
<211> LENGTH: 21
<212> TYPE: DNA
<213> ORGANISM: Homo sapiens

<400> SEQUENCE: 64

| | |
|---|---|
| ttggaaagca ggcaagactt t | 21 |

<210> SEQ ID NO 65
<211> LENGTH: 26
<212> TYPE: DNA
<213> ORGANISM: Homo sapiens

<400> SEQUENCE: 65

| | |
|---|---|
| actctccaac aattagaagc acctta | 26 |

<210> SEQ ID NO 66
<211> LENGTH: 22
<212> TYPE: DNA
<213> ORGANISM: Homo sapiens

```
<400> SEQUENCE: 66
caggaagaat tgaaagaact tc                                              22

<210> SEQ ID NO 67
<211> LENGTH: 24
<212> TYPE: DNA
<213> ORGANISM: Homo sapiens

<400> SEQUENCE: 67
gggcagaagt tttgaatgca ctta                                            24

<210> SEQ ID NO 68
<211> LENGTH: 25
<212> TYPE: DNA
<213> ORGANISM: Homo sapiens

<400> SEQUENCE: 68
ttaccccaaa ttcattgagc actta                                           25

<210> SEQ ID NO 69
<211> LENGTH: 23
<212> TYPE: DNA
<213> ORGANISM: Homo sapiens

<400> SEQUENCE: 69
tcatagaaac tgtctagcac ttc                                             23

<210> SEQ ID NO 70
<211> LENGTH: 23
<212> TYPE: DNA
<213> ORGANISM: Homo sapiens

<400> SEQUENCE: 70
tcaaaaaacc ttataagcac tta                                             23

<210> SEQ ID NO 71
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 71
uaagugcuuc cauguuuugg uga                                             23

<210> SEQ ID NO 72
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 72
uaagugcuuc cauguuuag uag                                              23

<210> SEQ ID NO 73
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 73
uaagugcuuc cauguuucag ugg                                             23
```

```
<210> SEQ ID NO 74
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 74
uaagugcuuc cauguuugag ugu                                              23

<210> SEQ ID NO 75
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 75
uaagugcuuc cauguuuuag ugu                                              23
```